(12) United States Patent
Messersmith et al.

(10) Patent No.: US 8,227,628 B2
(45) Date of Patent: Jul. 24, 2012

(54) METHOD OF SYNTHESIZING ACETONIDE-PROTECTED CATECHOL-CONTAINING COMPOUNDS AND INTERMEDIATES PRODUCED THEREIN

(75) Inventors: Phillip B. Messersmith, Clarendon Hills, IL (US); Bi-huang Hu, Watertown, MA (US); Zhongqiang Liu, Evanston, IL (US)

(73) Assignee: Northwestern University, Evanston, IL (US)

( * ) Notice: Subject to any disclaimer, the term of this patent is extended or adjusted under 35 U.S.C. 154(b) by 373 days.

(21) Appl. No.: 12/500,398

(22) Filed: Jul. 9, 2009

(65) Prior Publication Data

US 2010/0087622 A1    Apr. 8, 2010

Related U.S. Application Data

(60) Provisional application No. 61/079,331, filed on Jul. 9, 2008.

(51) Int. Cl.
*C07D 317/50*    (2006.01)

(52) U.S. Cl. ...................................... 549/444
(58) Field of Classification Search ................... 549/444
See application file for complete search history.

(56) References Cited

U.S. PATENT DOCUMENTS 3,846,573 A    11/1974   Okumura et al.

FOREIGN PATENT DOCUMENTS

| DE | 2342474    | 3/1974 |
| JP | 48022473   | 7/1973 |
| WO | 02059107   | 8/2002 |
| WO | 03061660   | 7/2003 |
| WO | 2008043911 | 4/2008 |

OTHER PUBLICATIONS

Babu et al., Synth. Commun. 2005, 35, (13), 1795-1802.
Benes, Trends Pharmacol. Sci. 2001, 22, (1), 46-47.
Berthod et al., J. Chromatogr. A 1996, 731, 123-137.
Bojarski et al., Bioorg. Med. Chem. 2001, 10, (1), 87-95.
Cai et al., J. Am. Chem. Soc. 2004, 126, (46), 15030-15031.
Cluzeau et al., Org. Biomol. Chem. 2007, 5, 1915-1923.
Cole et al., Aust. J. Chem. 1980, 33, (3), 675-80.
Fan, J. Am. Chem. Soc. 2005, 127, (45), 15843-15847.
Fant, et al., Biomacromolecules 2002, 3, 732-741.
Garcia-Alvarez et al., ChemMedChem 2007, 2, (4), 496-504.
Godsay et al., J. Polym. Mater. 1991, 8, (3), 207-211.
Griesbeck et al., Tetrahedron 1994, 50, 701-714.
Harwood et al., Biopolymers 1978, 17, (12), 2939-2943.
Hasegawa et al., Kagaku to Kyoiku 1991, 39, 686-687.
Henz et al., J. Inf. Rec. 1994, 21, 567-569.
Hu et al., Tetrahedron Lett. 2000, 41, 5795-5798.
Ikeuchi et al., Heterocycles 2005, 65, (12), 2925-2935.
Ishihara et al., Org. Lett. 2006, 8, 1921-1924.
Kolasa et al., J. Org. Chem. 1990, 55, 1711-1721.
Kondejewski et al., J. Biol. Chem. 1999, 274, 13181-13192.
LaVoie et al., J. Neurosci. 1999, 19, (4), 1484-1491.
Lee et al., Adv. Mater. 2008, 20, 4154-4157.
Lee et al., Adv. Mater. 2008, 20, 1916-1923.
Lee et al., Proc. Natl. Acad. Sci. U. S. A. 2006, 103, 12999-13003.
Lee et al., Synthesis 2001, 2247-2254.
Li et al., Biomaterials 2008, 29, (35), 4592-4597.
Liu et al., Tetrahedron Lett. 2008, 49, (38), 5519-5521.
Maryanoff, Chem. Rev. 2004, 104, (3), 1431-1628.
Meltzer et al., Bioorg. Med. Chem. Lett. 2003, 13, (22), 4133-4137.
Mendis et al., Can. J. Neurol. Sci. 1999, 26, 89-103.
Messersmith, Science 2008, 319, 1767-1768.
Miserez et al., Science 2008, 319, 1816-1819.
Morita et al., Agric. Biol. Chem. 1975, 39, (2), 547-549.
Nichols et al., J. Med. Chem. 1979, 22, (10), 1264-1267.
Niederstein et al., Ann. Chem. 1989, (12), 1189-1193.
Ogura et al., Tetrahedron Lett. 1971, 3151-3154.
Okano et al., J. Am. Chem. Soc. 2006, 128, (22), 7136-7137.
Papov et al., J. Biol. Chem. 1995, 270, 20183-20192.
Rice-Ficht et al., Mol. Biochem. Parasitol. 1992, 54, 129-141.
Sever et al., Tetrahedron 2001, 57, 6139-6146.
Shashoua et al., W. Life Sci. 1996, 58, (16), 1347-1357.
Shen et al., J. Biol. Chem. 1982, 257, (13), 7294-7297.
Shi et al., Bioorg. Med. Chem. Lett.2006, 16, 2341-2346.
Soloshonok et al., Synthesis 2008, 693-695.
Statz et al., J. Am. Chem. Soc. 2005, 127, 7972-7973.
Waite et al., Mol. Biochem. Parasitol. 1992, 54, 143-151.
Wen et al., Org. Lett. 2004, 6, 2721-2724.
Xu et al., J. Am. Chem. Soc. 2004, 126, (32), 9938-9939.
Yoshino, Bull. Chem. Soc. Jpn. 1979, 52, 3005-3009.
Yu et al., Macromolecules 1998, 31, 4739-4745.
Yu et al., Macromolecules 2007, 40, (11), 3960-3964.
Zhao et al., J. Biol. Chem. 2005, 280, 42938-42944.

*Primary Examiner* — Taofiq A Solola
(74) *Attorney, Agent, or Firm* — Quarles & Brady LLP

(57) ABSTRACT

The inventors disclose here a novel, facile approach to the synthesis of acetonide-protected catechol-containing compounds having at least one amine group. In specific embodiments, the invention provides novel methods of synthesizing 3,4-dihydroxyphenylalanine (H-DOPA(acetonide)-OH (6)), Fmoc-protected H-DOPA(acetonide)-OH (Fmoc-DOPA(acetonide)-OH (7)), Fmoc-protected dopamine (Fmoc-dopamine(acetonide) (10)), TFA-protected dopamine (TFA-dopamine(acetonide) (13)) and acetonide-protected 4-(2-aminoethyl)benzene-1,2-diol (acetonide-protected dopamine (14)).

17 Claims, 101 Drawing Sheets

A)
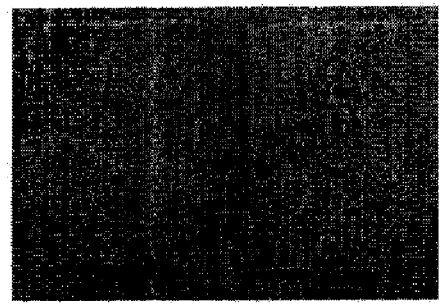
B)
C)
Figure 12

RP-HPLC of Fmoc-DOPA(acetonide)-Gly-Gly-Lys(Boc)-Lys(Boc)-OH

RP-HPLC of Fmoc-DOPA(acetonide)-Gly-Gly-Lys(Boc)-Lys(Boc)-OH

RP-HPLC of Fmoc-DOPA-Gly-Gly-Lys-Lys-OH

RP-HPLC of Fmoc-DOPA-Gly-Gly-Lys-Lys-OH

Chiral-HPLC Analysis: D/L-DOPA(Reference)

Chiral-HPLC Analysis: Fmoc-DOPA(acetonide)-OH (7)

Phth-DOPA(acetonide)-OMe
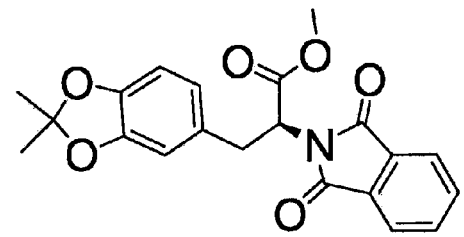
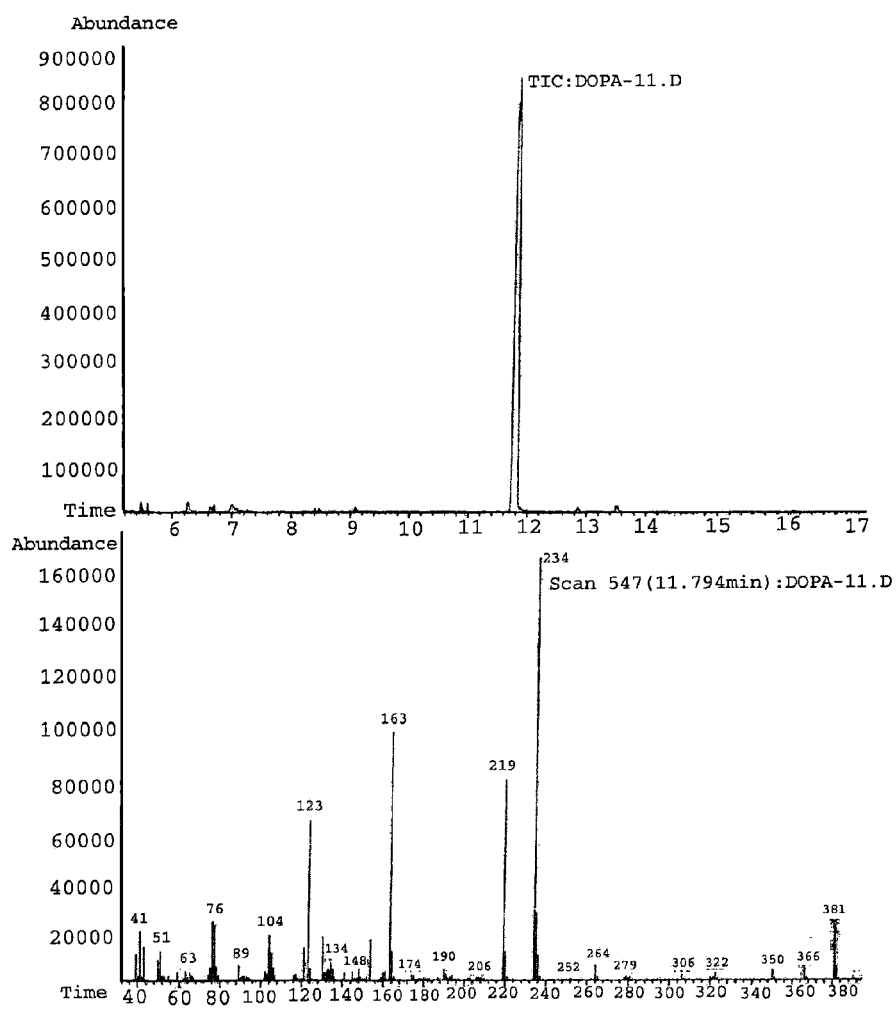
Figure 21

Phth-DOPA(acetonide)-OMe (4). $^1$H NMR (500 MHz, CDCl$_3$)
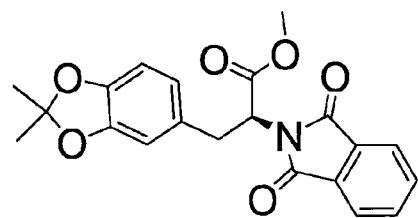
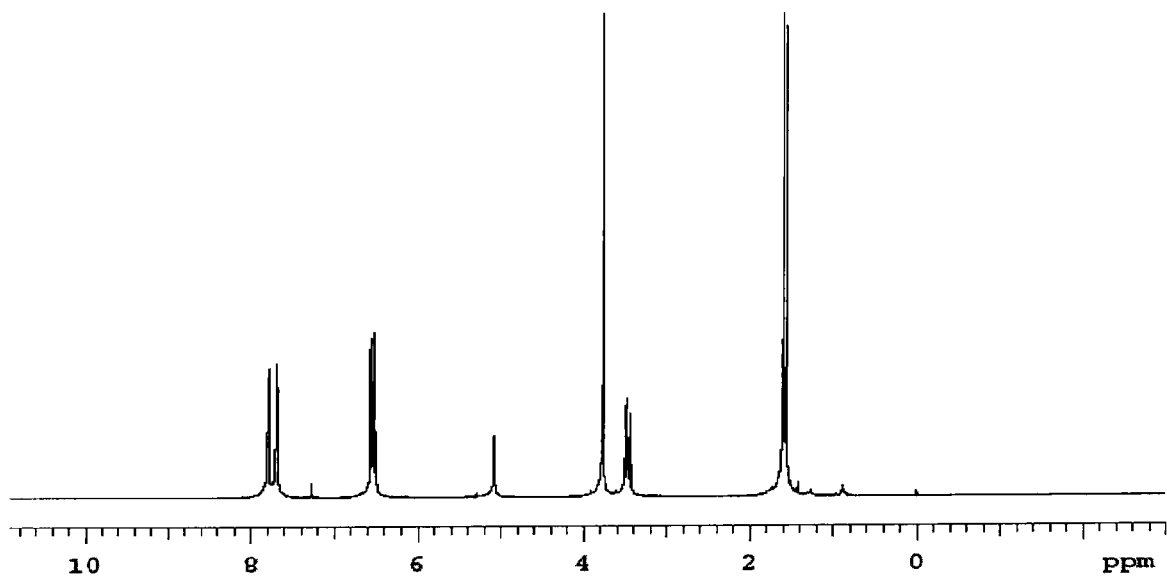
Figure 22

Phth-DOPA(acetonide)-OMe (4). $^{13}$C NMR (125 MHz, CDCl$_3$)

H-DOPA(acetonide)-OMe (5a). $^1$H NMR (500 MHz, CDCl$_3$)
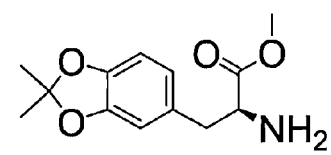
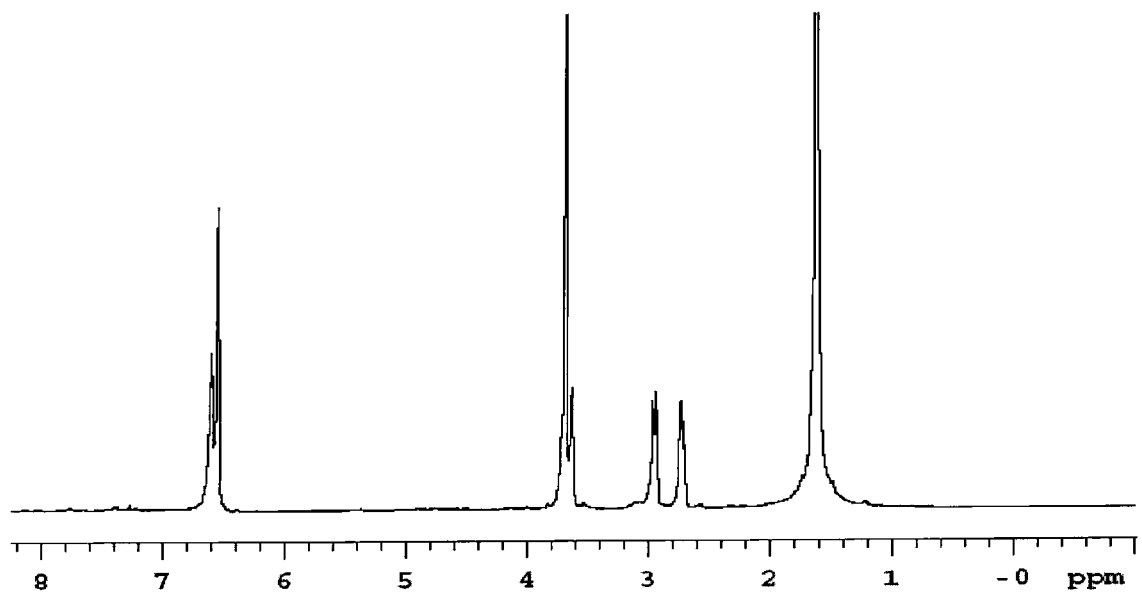
Figure 24

H-DOPA(acetonide)-OMe (5a). $^{13}$C NMR (125 MHz, CDCl$_3$)

Hydrochloride Salt of H-DOPA(acetonide)-OH (5b). $^1$H NMR (500 MHz, CD$_3$OD)

Hydrochloride Salt of H-DOPA(acetonide)-OH (5b). $^{13}$C NMR (125 MHz, CD$_3$OD)

Hydrochloride Salt of H-DOPA(acetonide)-OH (5b). HMQC (500 MHz, CD₃OD)

Hydrochloride Salt of H-DOPA(acetonide)-OH (5b). HMBC (500 MHz, CD₃OD)

Fmoc-DOPA(acetonide)-OH (7). $^1$H NMR (500 MHz, CDCl$_3$)

Fmoc-DOPA(acetonide)-OH (7). $^{13}$C NMR (125 MHz, CDCl$_3$)

A)  TFA-DOPA(acetonide)-OMe
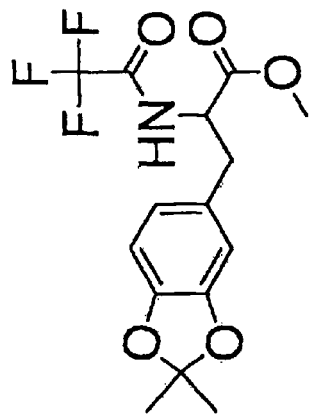
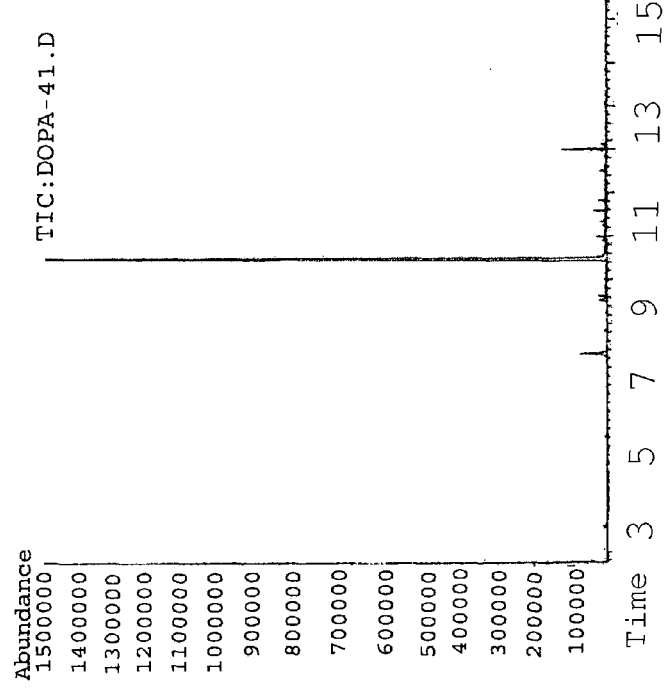
Figure 32

TFA-DOPA(acetonide)-OMe $^1$H NMR (500 MHz, CDCl$_3$)
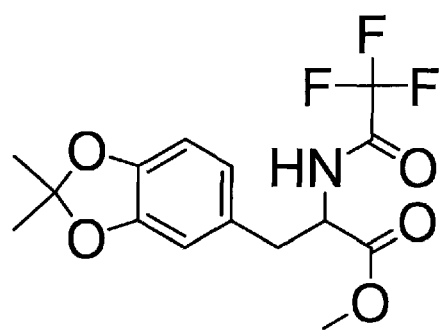
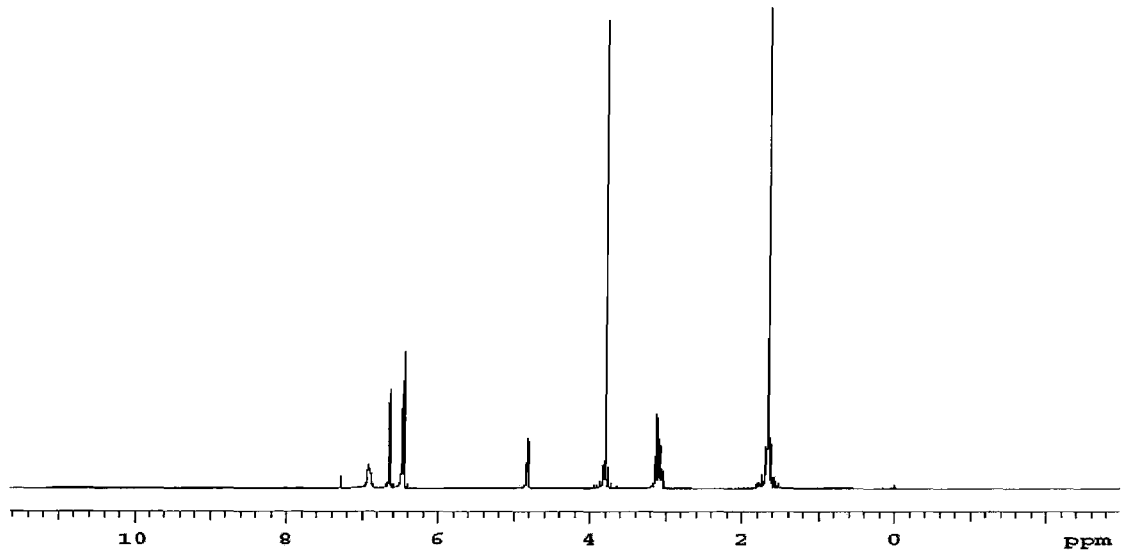
Figure 33

TFA-DOPA(acetonide)-OMe $^{13}$C NMR (125 MHz, CDCl$_3$)

A) TFA-DOPA(Chex)-OMe
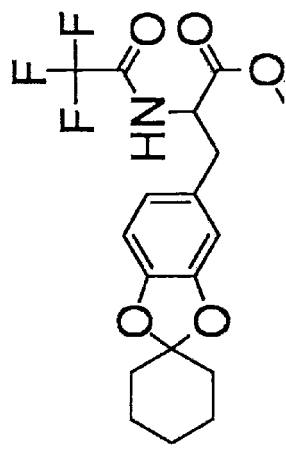
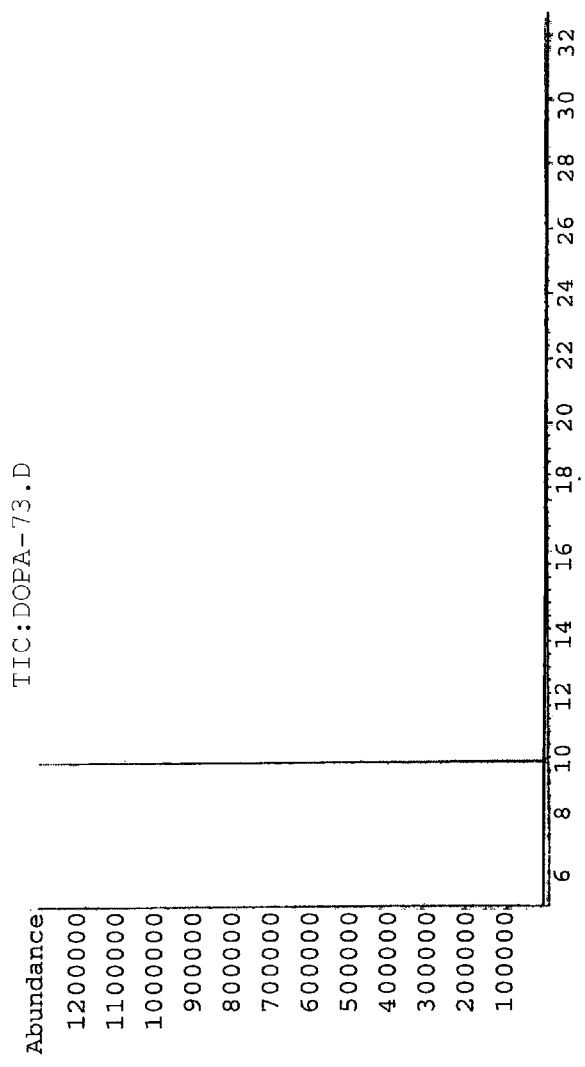
Figure 35

TFA-DOPA(Chex)-OMe $^1$H NMR (500 MHz, CDCl$_3$)

TFA-DOPA(BA)-OMe $^1$H NMR (500 MHz, CDCl$_3$)
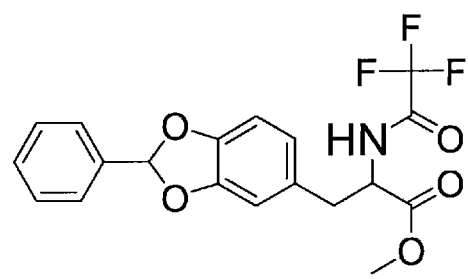
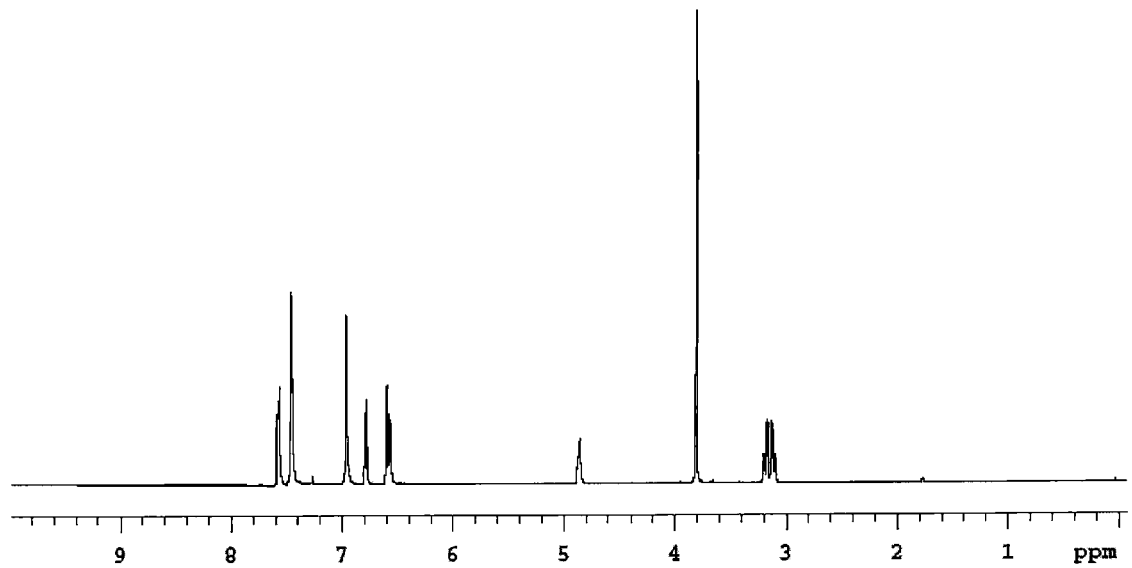
Figure 38

Fmoc-DOPA(Chex)-OH $^1$H NMR (500 MHz, CDCl$_3$)
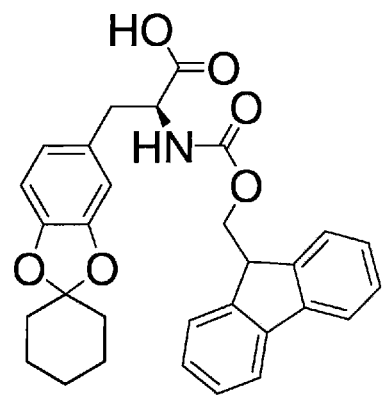
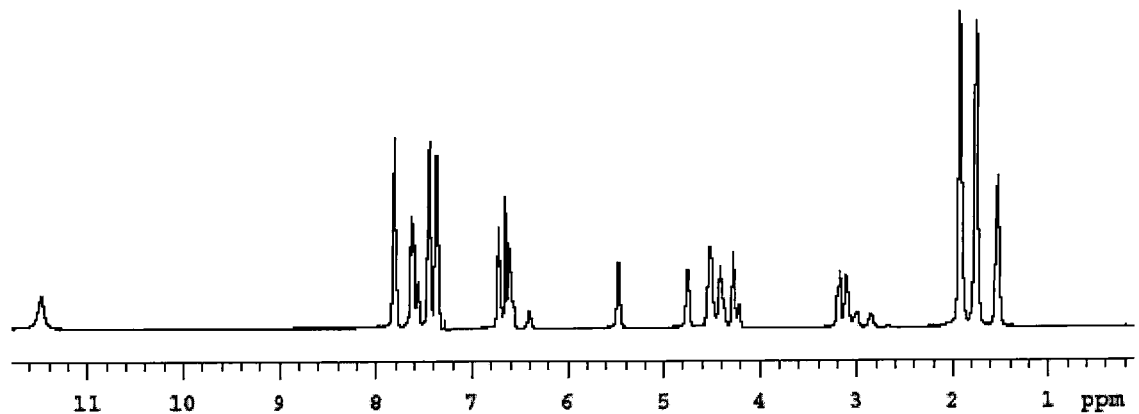
Figure 40

Boc-DOPA(acetonide)-OH $^1$H NMR (500 MHz, CDCl$_3$)
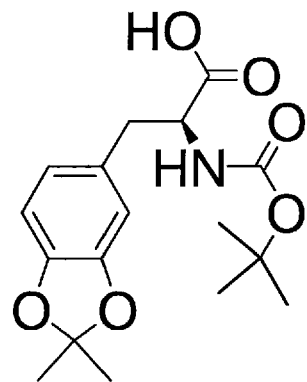
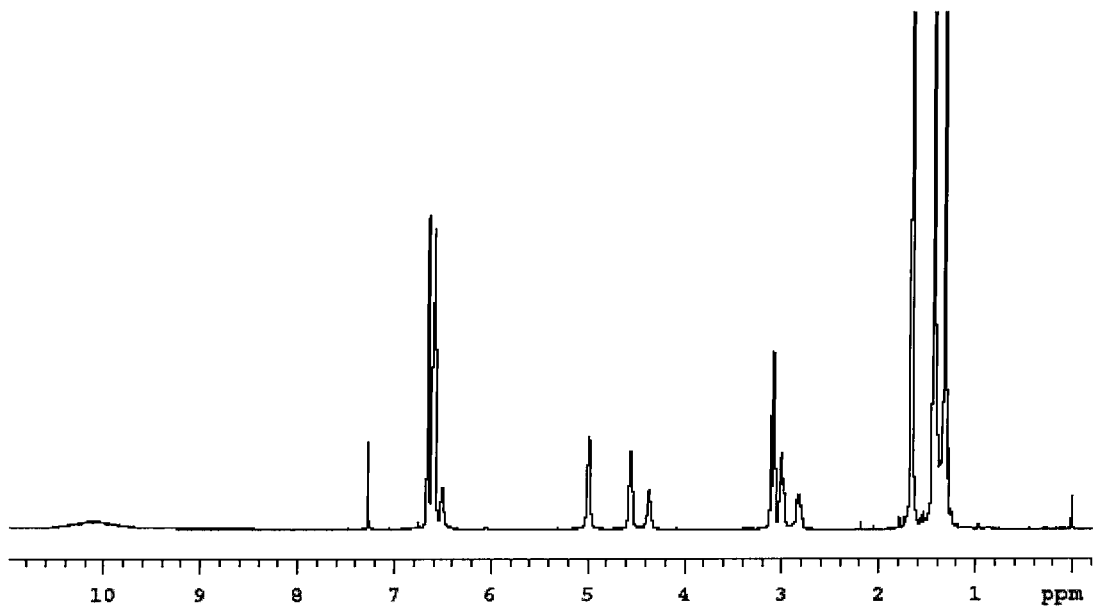
Figure 42

Boc-DOPA(acetonide)-OH $^1$H NMR (500 MHz, CDCl$_3$)
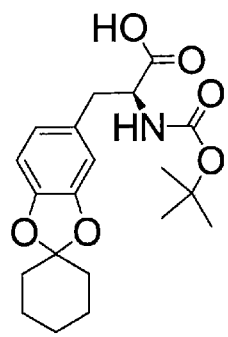
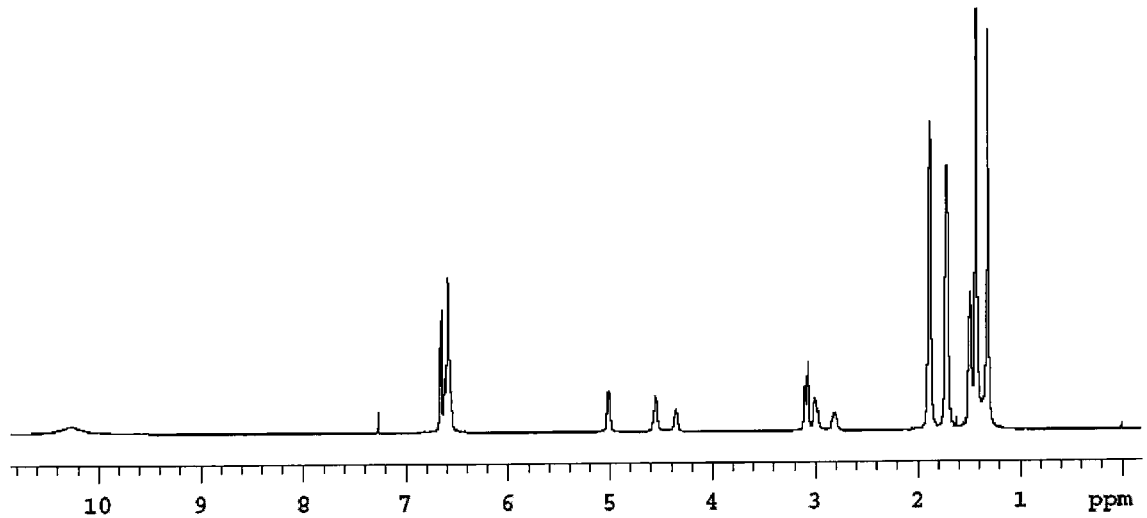
Figure 44

A) MALDI-TOF Spectra of Fmoc-DOPA(acetonide)-Gly-Gly-Lys(Boc)-Lys(Boc)-OH

MALDI-TOF Spectra of Fmoc-DOPA(acetonide)-Gly-Gly-Lys(Boc)-Lys(Boc)-OH

A)

A) MALDI-TOF Spectra of Boc-DOPA(Chex)-Gly-Gly-Lys(Boc)-Lys(Boc)-OH

Phth-dopamine $^1$H NMR (500 MHz, DMSO-$d_6$)
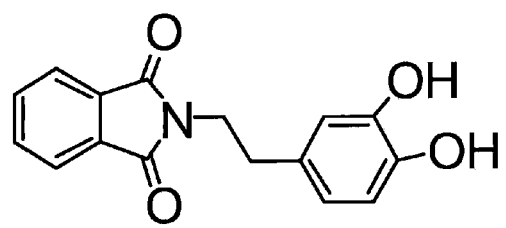
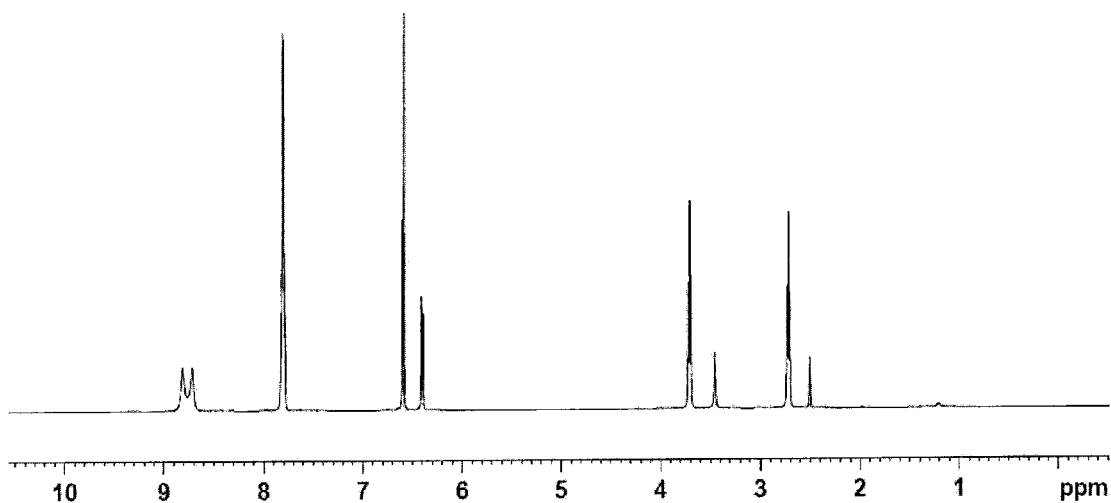
Figure 49

GC-MS Spectrum of Phth-dopamine(acetonide)
A) 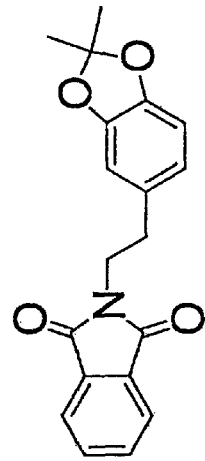
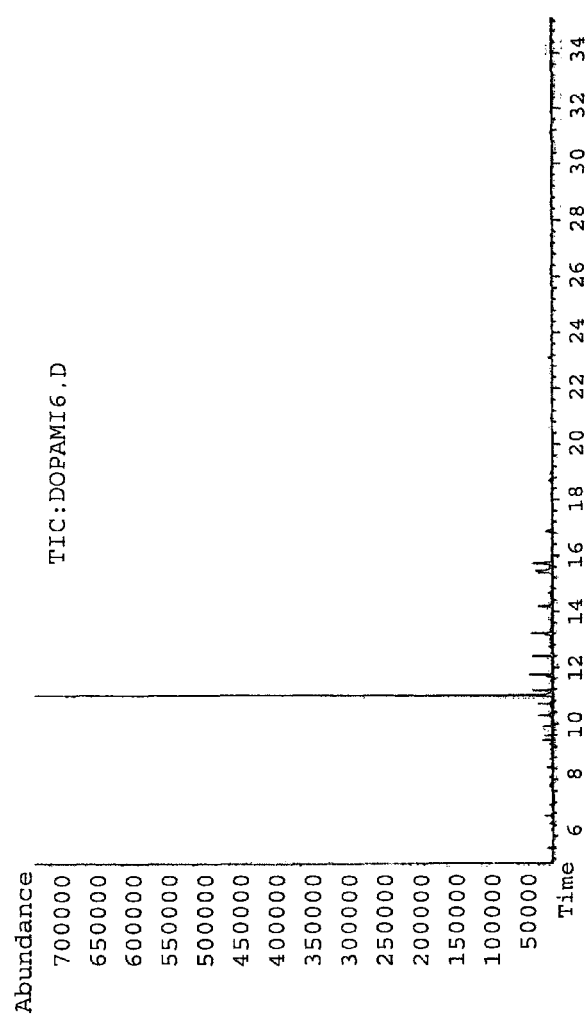
Figure 51

Phth-dopamine(acetonide). $^1$H NMR (500 MHz, CDCl$_3$)
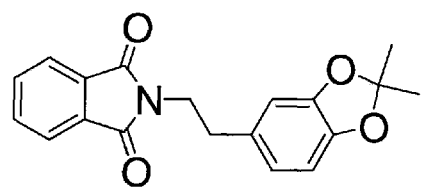
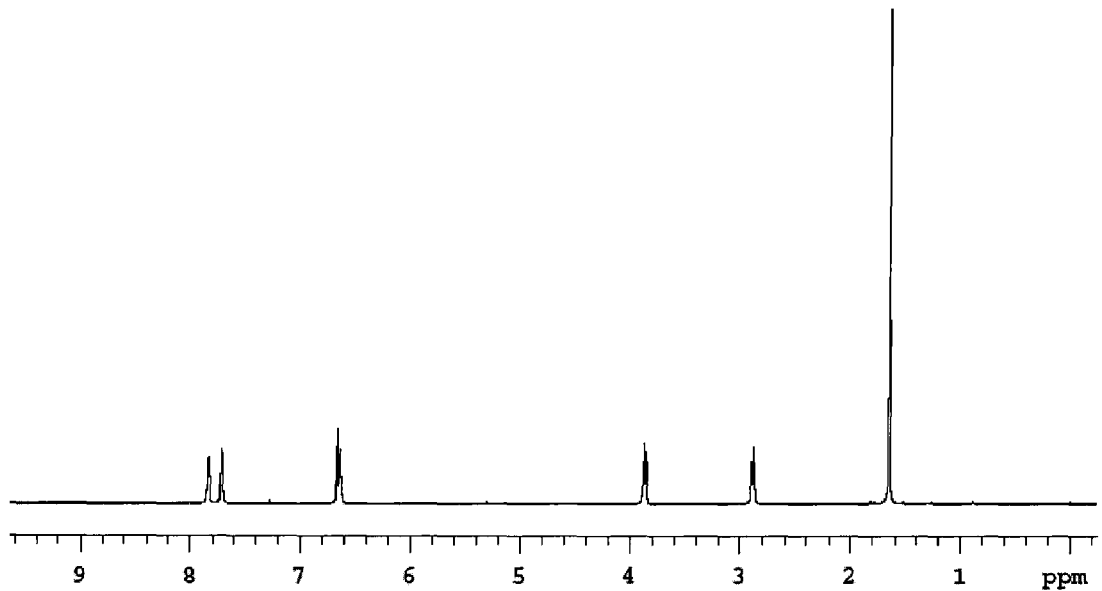
Figure 52

LC-MS Data of TsOH-DDTQ (Positive Mode)
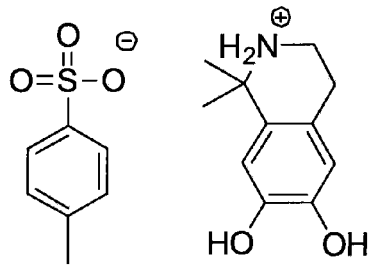
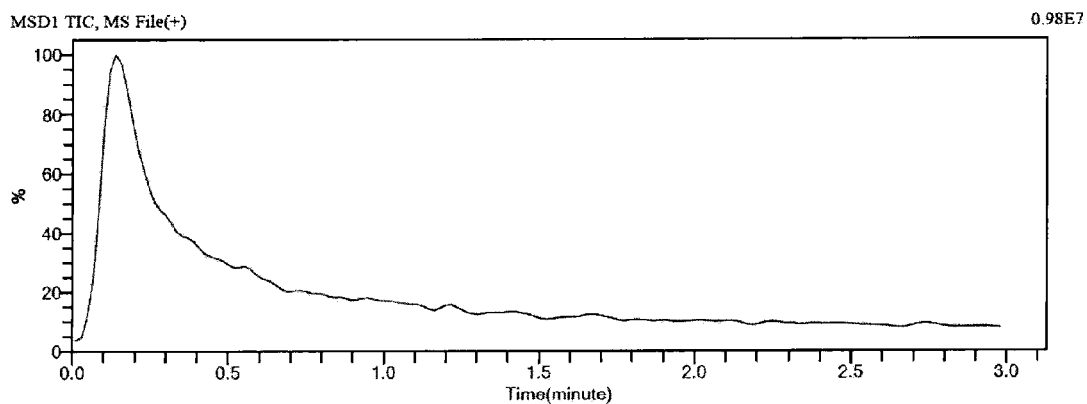
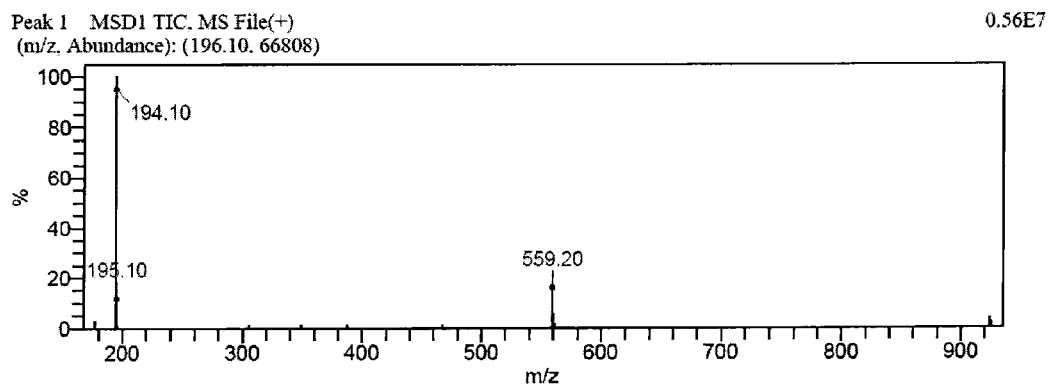
Figure 56

LC-MS Data of TsOH-DDTQ (Negative Mode)
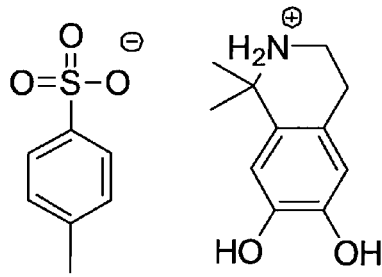
Agilent LC/MS Data Browser Report -1-
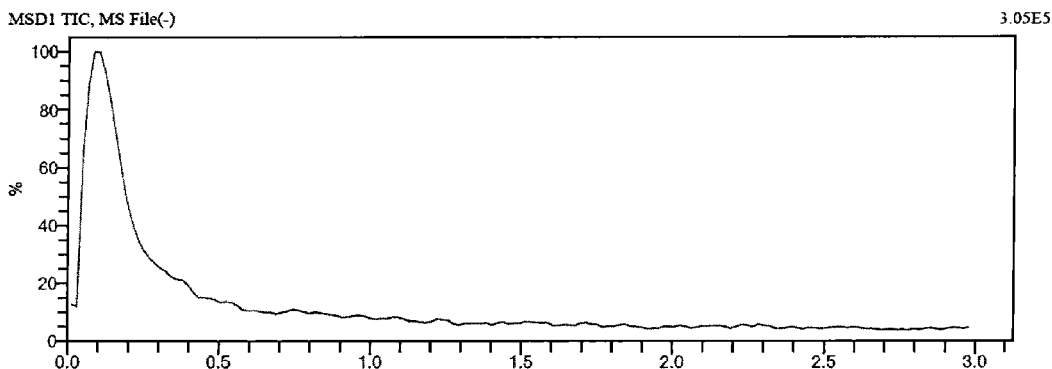
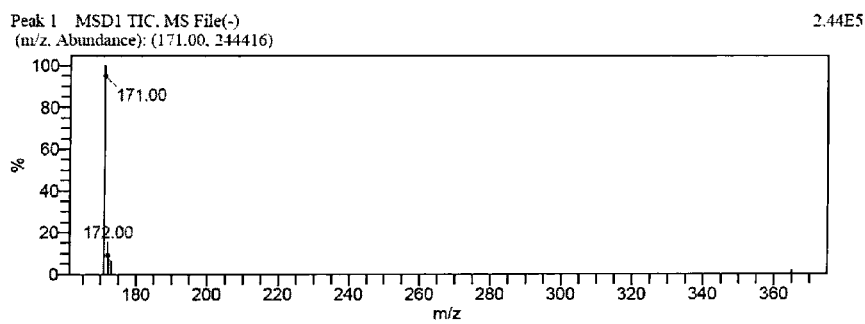
Figure 57

TsOH-DDTQ $^1$H NMR (500 MHz, DMSO-$d_6$)
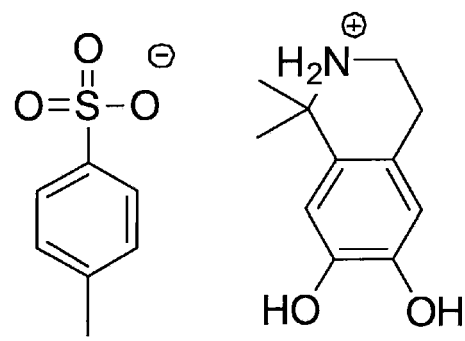
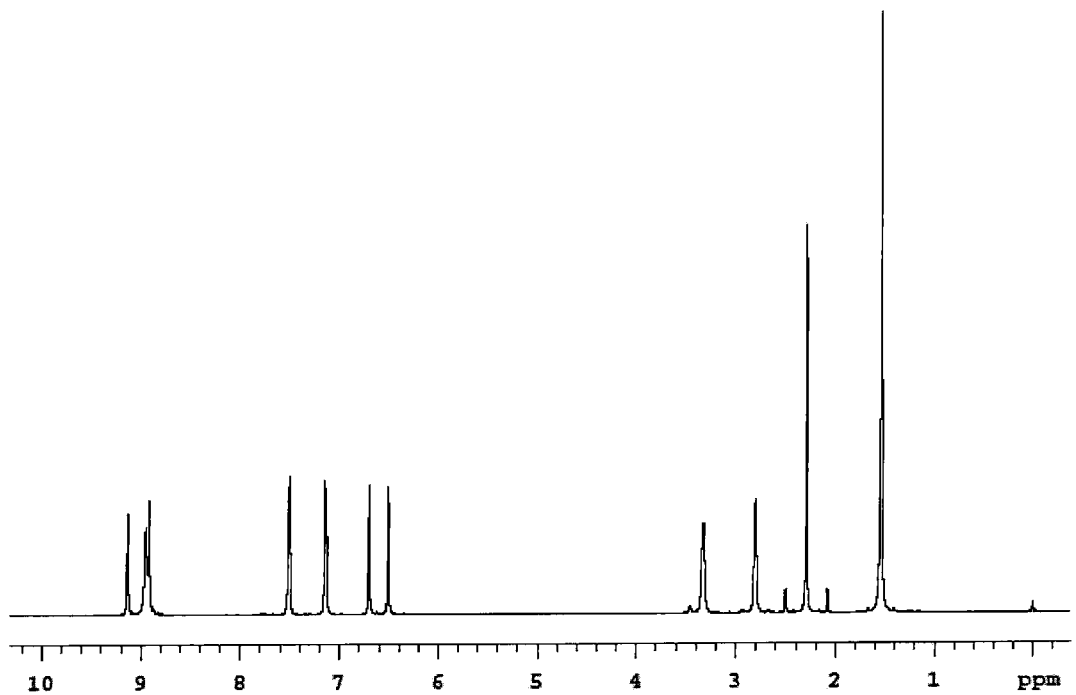
Figure 58

TsOH-DDTQ $^{13}$C NMR (125 MHz, DMSO-$d_6$)

TsOH-DDTQ $^{13}$C NMR (125 MHz, DMSO-$d_6$)
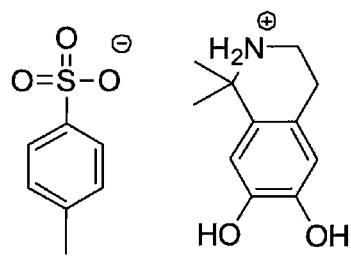
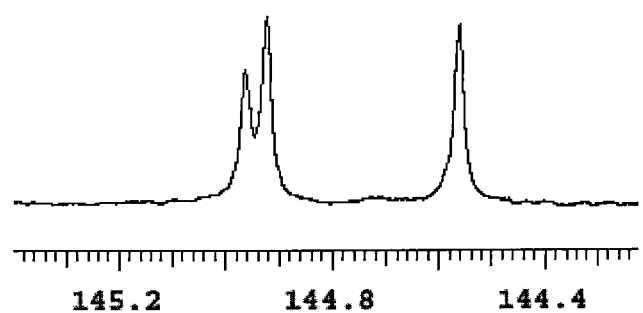
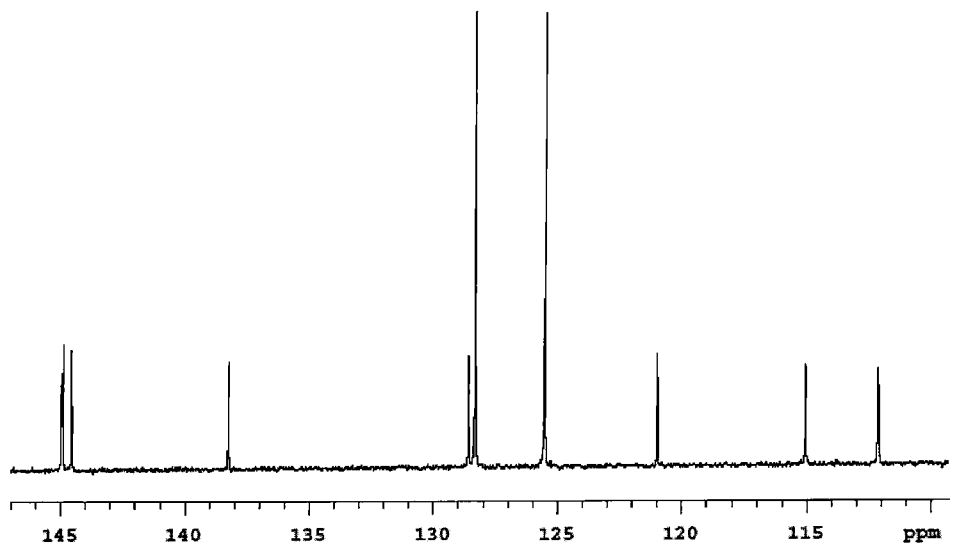
Figure 60

TsOH-DDTQ $^{13}$C NMR-DEPT (125 MHz, DMSO-$d_6$)

TsOH-DDTQ $^1$H NMR-COSY (500 MHz, DMSO-$d_6$)
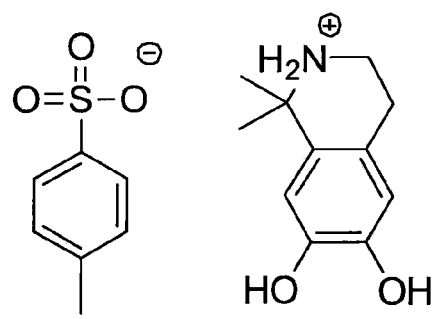
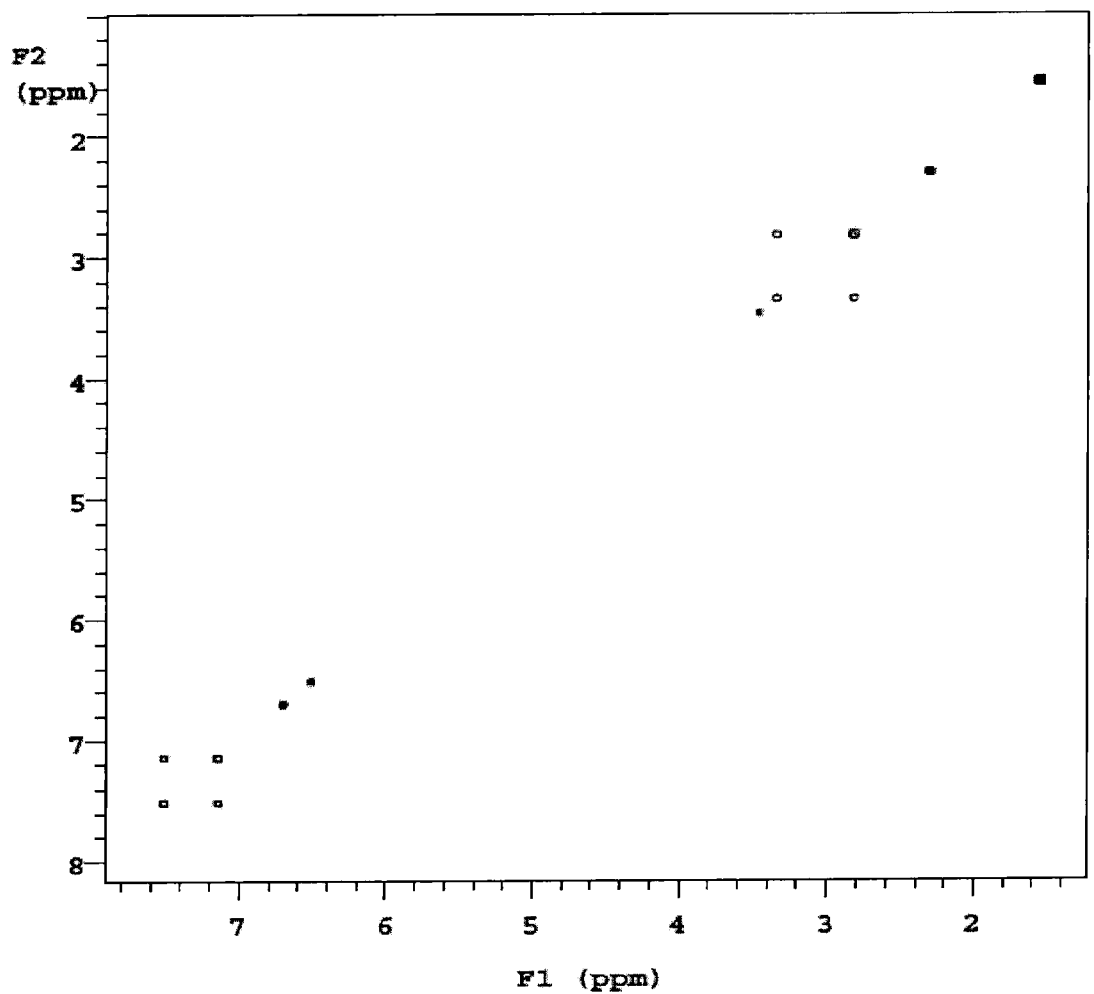
Figure 62

Hydrochloride Salt of (S)-methyl 6,7-dihydroxy-1,1-dimethyl-1,2,3,4-tetrahydroisoquinoline-3-carboxylate (1). $^1$H NMR (500 MHz, CD$_3$OD)
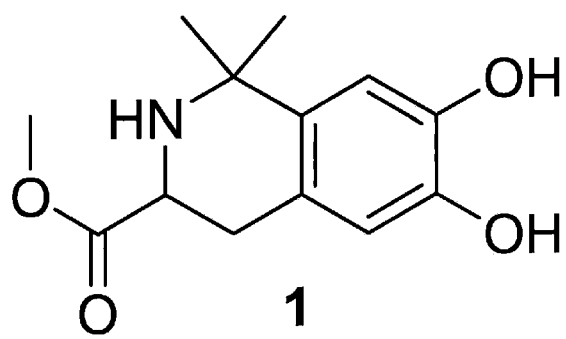
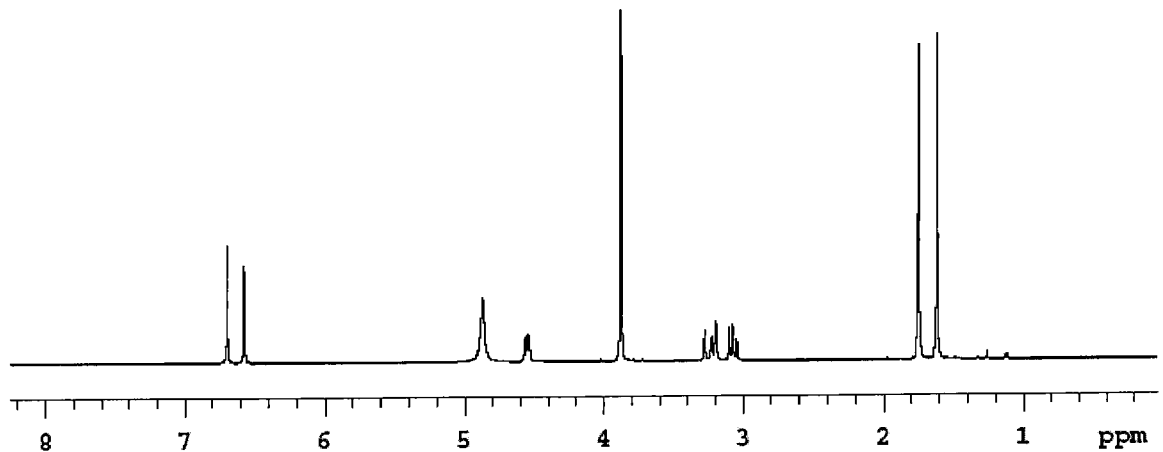
Figure 63

Hydrochloride Salt of (S)-methyl 6,7-dihydroxy-1,1-dimethyl-1,2,3,4-tetrahydroisoquinoline-3-carboxylate. $^{13}$C NMR (125 MHz, CD$_3$OD)

Hydrochloride Salt of (S)-methyl 6,7-dihydroxy-1,1-dimethyl-1,2,3,4-tetrahydroisoquinoline-3-carboxylate. HMQC (500 MHz, $CD_3OD$)

Hydrochloride Salt of (S)-methyl 6,7-dihydroxy-1,1-dimethyl-1,2,3,4-tetrahydroisoquinoline-3-carboxylate. HMBC (500 MHz, CD₃OD)

TFA-dopamine $^1$H NMR (500 MHz, DMSO-$d_6$)
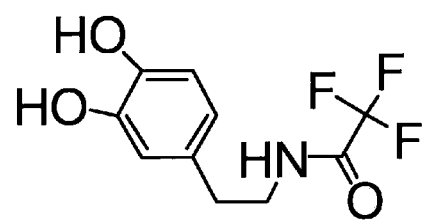
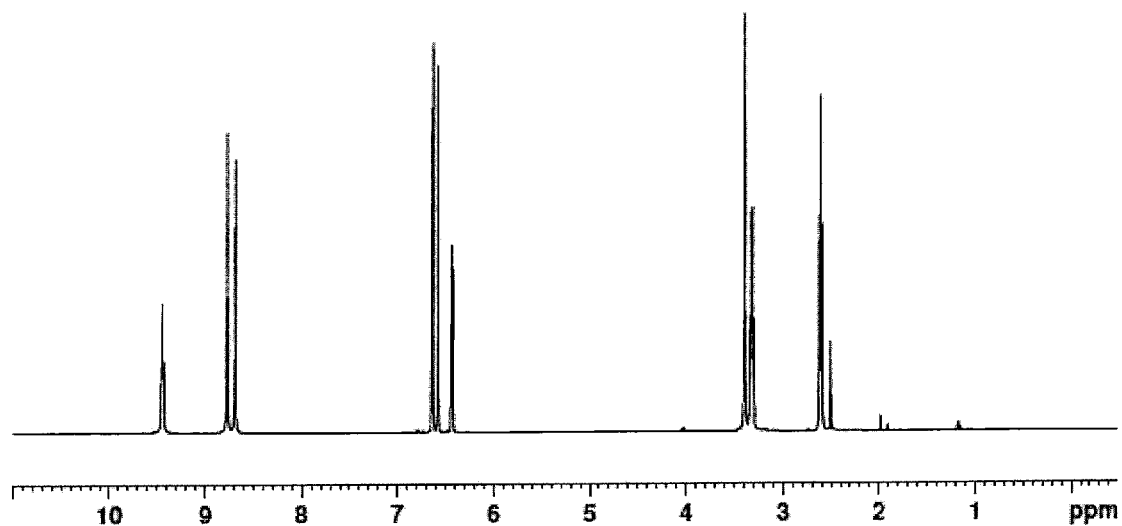
Figure 67

TFA-dopamine $^{13}$C NMR (125 MHz, DMSO-$d_6$)

TFA-dopamine(acetonide) $^1$H NMR (500 MHz, CDCl$_3$)
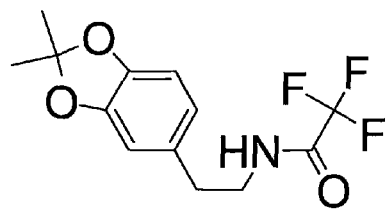
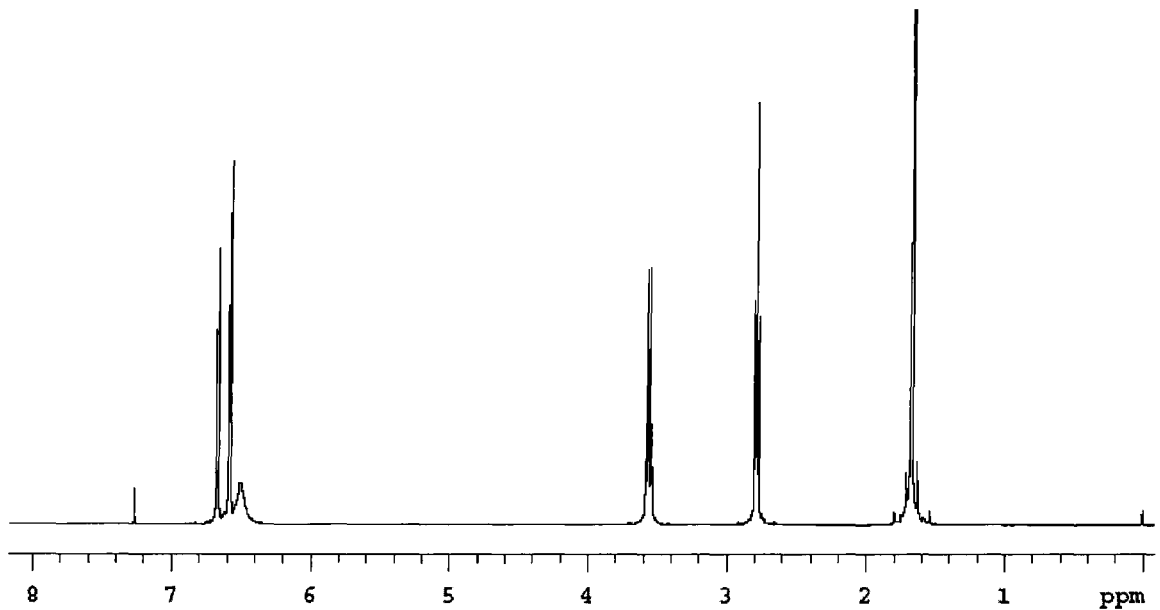
Figure 69

TFA-dopamine(acetonide) $^{13}$C NMR (125 MHz, CDCl$_3$)

GC-MS Spectrum of Dopamine(acetonide)
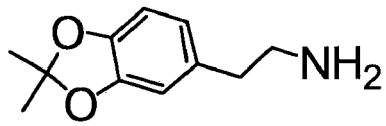
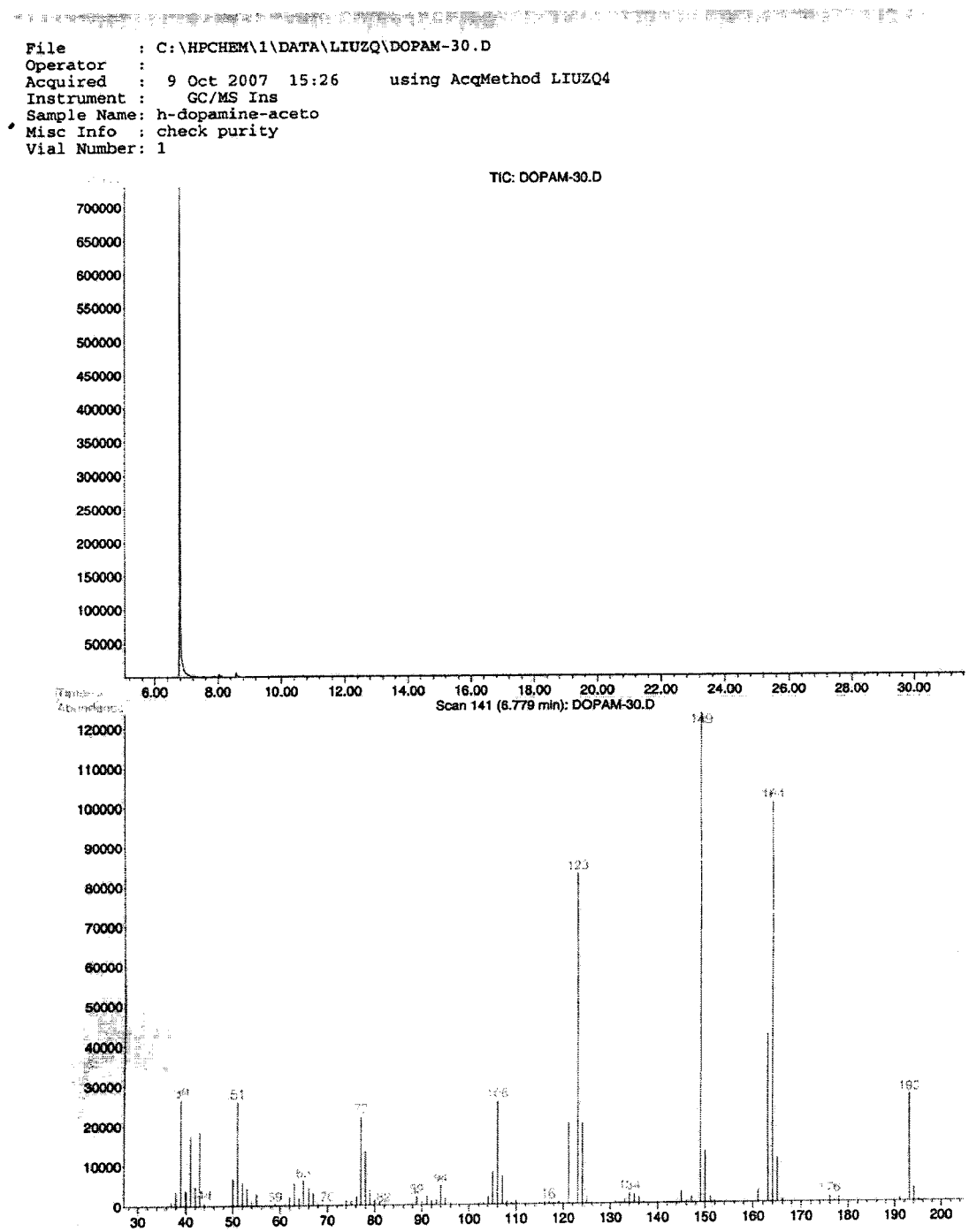
Figure 72

Dopamine(acetonide). $^1$H NMR (500 MHz, CDCl$_3$)
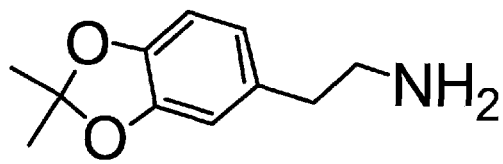
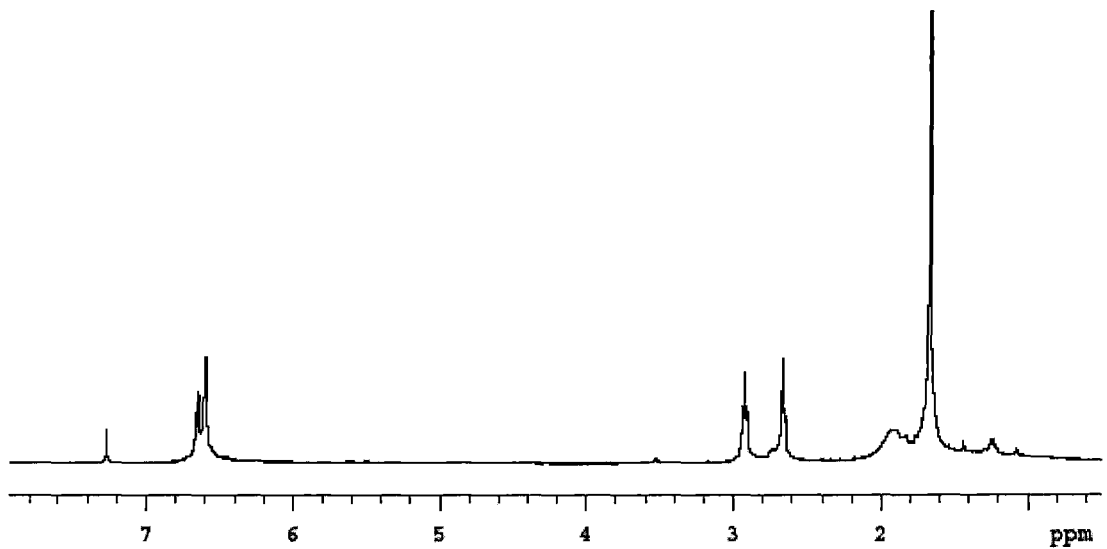
Figure 73

Dopamine(acetonide). $^{13}$C NMR (125 MHz, CDCl$_3$)

Dopamine(acetonide). $^{13}$C NMR-DEPT (125 MHz, CDCl$_3$)

MS Spectra of DHA-dopamine(acetonide)

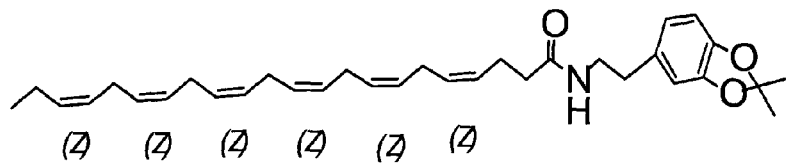

Sample#: 2    Sample Location: Vial 38    Sample Name: dha-da-a    Operator: Zhongqiang Liu
Sample Description: * No target masses specified *
Date: 10/3/2008    Time: 9:46:42 PM    Instrument: MSD1100    Software: Easy-Access
Acq. Method: POS MEOH DIRECT.M
DA Method: POS MEOH DIRECT.M
Data File: C:\MSERCMSD1100\MESSERSMITH\10-08\031008-DHA-DA-A2-00554.D
DataBrowser File: C:\Users\zq\Desktop\Original-data\agilent-LCMS\10-08\dha-da-a.AEV

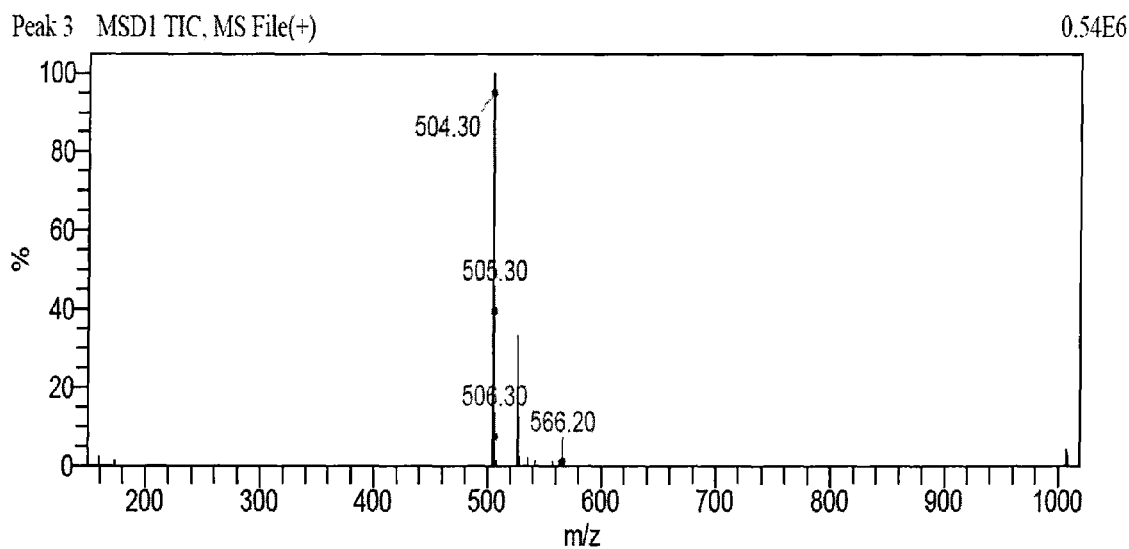

Figure 76

DHA-dopamine(acetonide). $^1$H NMR (500 MHz, CDCl$_3$)

DHA-dopamine(acetonide). $^{13}$C NMR (125 MHz, CDCl$_3$)

DHA-dopamine(acetonide). $^{13}$C NMR (125 ppm to 135 ppm).

MS Spectra of DHA-dopamine
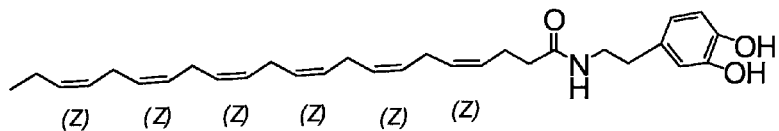
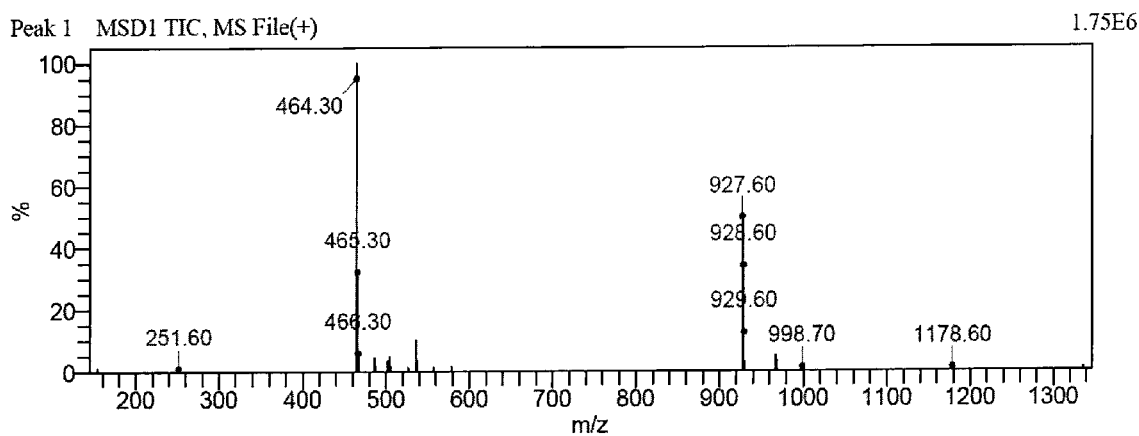
Figure 81

DHA-dopamine $^{13}$C NMR (115 ppm to 133 ppm)

A) MA-dopamine(acetonide)
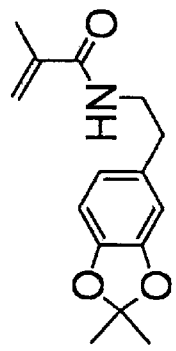
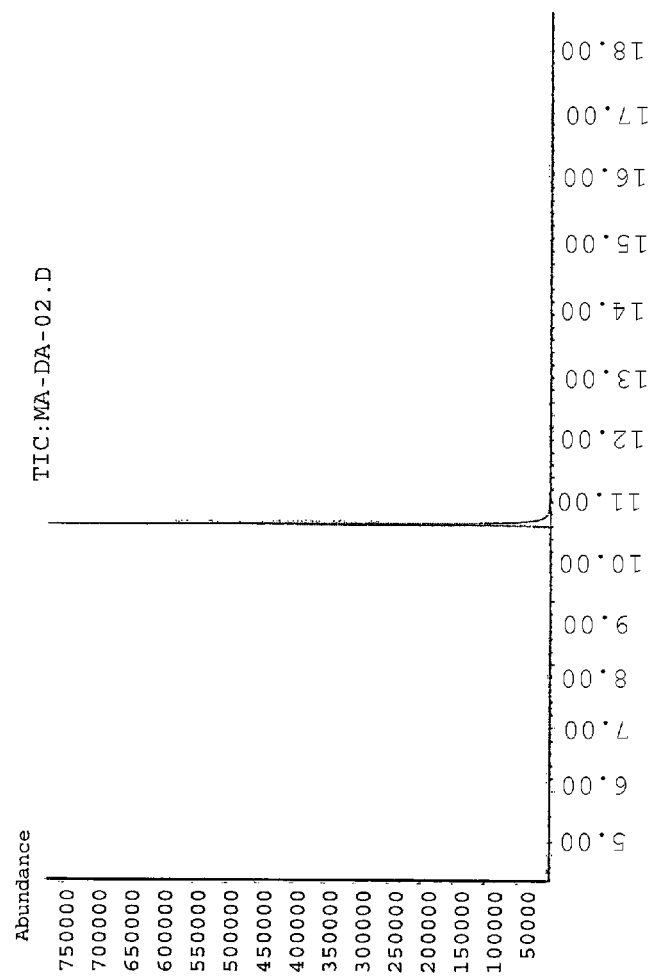
Figure 86

MA-dopamine(acetonide) $^{13}$C NMR (125 MHz, CDCl$_3$)

DHPA(Chex)-OMe $^1$H NMR (500 MHz, CDCl$_3$)
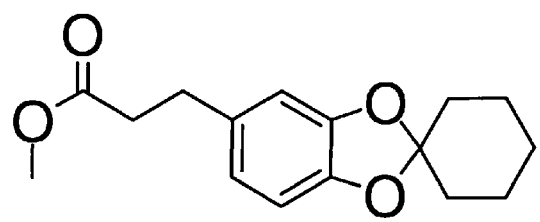
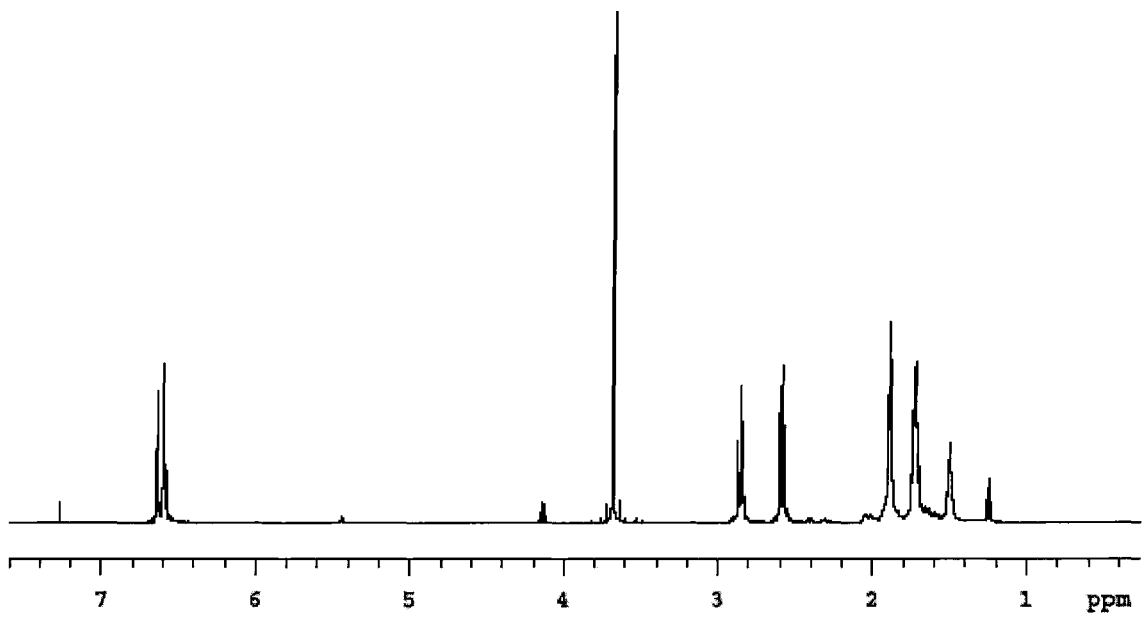
Figure 89

DHCA(Chex)-OH $^1$H NMR (500 MHz, CDCl$_3$)

DHPA(Chex)-OSu $^1$H NMR (500 MHz, CDCl$_3$)
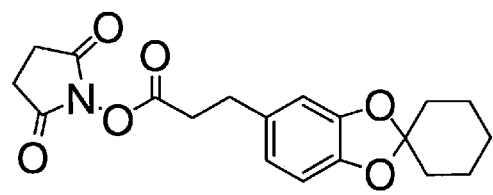
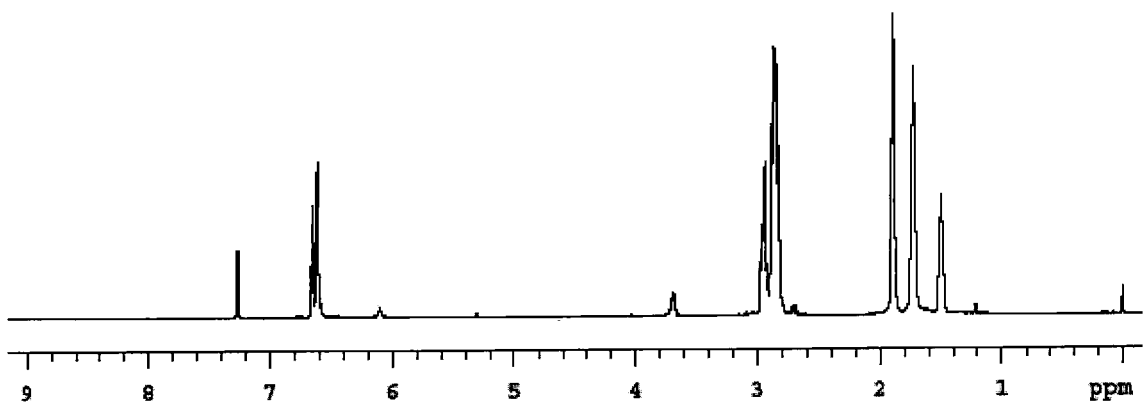
Figure 93

METHOD OF SYNTHESIZING ACETONIDE-PROTECTED CATECHOL-CONTAINING COMPOUNDS AND INTERMEDIATES PRODUCED THEREIN

CROSS-REFERENCE TO RELATED APPLICATIONS

This application claims priority to U.S. Provisional Application No. 61/079,331, filed Jul. 9, 2008, which is hereby incorporated by reference herein for all purposes.

STATEMENT REGARDING FEDERALLY SPONSORED RESEARCH OR DEVELOPMENT

The present invention was made with government support from National Institutes of Health Grant No. R37 DE 014193. The United States Government has certain rights in the invention.

FIELD OF THE INVENTION

The invention relates generally to an improved method of synthesizing acetonide-protected catechol-containing molecules such as DOPA and dopamine. In addition, the invention includes novel chemical compositions produced by the method thereof.

BACKGROUND OF THE INVENTION

Catechol-containing molecules such as DOPA and dopamine are important compounds with widely useful effects as therapeutic agents. Acetonide-protected catechol-containing compounds such as DOPA and dopamine are useful in many applications, including Fmoc peptide synthesis and conjugating DOPA and dopamine with other small molecules, polymers, or macromolecules of interest.

DOPA.

The amino acid 3,4-dihydroxyphenylalanine (DOPA) (FIG. 1, 1) is found in a number of biological tissues, including the adhesive plaques of the marine mussel *Mytilus edulis*,[1,2] the cement proteins of the sandcastle worm *Phragmatopoma californica*,[3] squid beaks,[4] and in the eggshell precursor proteins of *Fasciola hepatica*.[5,6] The DOPA residues are thought to contribute to the bioadhesive and structural properties of these tissues.[7-9] As a therapeutic, L-DOPA is commonly prescribed for the treatment of Parkinson's disease.[10]

To facilitate the synthesis of DOPA-containing therapeutic compounds and biomimetic materials, it is necessary to properly protect the catechol side-chain of DOPA during chemical reactions. In the case of the synthesis of DOPA-containing peptides, solid phase peptide synthesis (SPPS) by Fmoc strategy is a preferred approach due to its convenience and efficiency.

Various protecting groups have been reported to protect the side-chain catechol group of DOPA residues, including cyclic ethyl orthoformate,[11] TBDPS,[12] and acetonide.[13,14] The acetonide protecting group has proven to be compatible with the Fmoc SPPS method,[15] but a synthetic route to Fmoc-DOPA(acetonide)-OH (7) has not been reported. Easy protection/deprotection together with good stability to strong bases and weak acids makes the acetonide protecting group especially useful.

One reported method to make H-DOPA(acetonide)-OH (6), from which Fmoc-DOPA(acetonide)-OH (7) may be synthesized, constructed the amino acid derivative from acetonide-protected 4-methylbenzene-1,2-diol in several steps leading to a racemic mixture of Fmoc-DOPA(acetonide)-OH.[13] However, conventional methods of synthesis are complicated, multi-step processes that often require an additional step of chiral separation to obtain an optically pure product.

Dopamine.

As a member of the catecholamine family, 4-(2-aminoethyl)benzene-1,2-diol (dopamine) contains both amino and catechol moieties, each capable of a diversity of potential reactions and interactions. In both vertebrate and invertebrate animals, dopamine is the precursor of norepinephrine and epinephrine but also an important neurotransmitter itself, essential to the normal functioning of the central nervous system.[33] Parkinson's disease, affecting about 1% of the senior population, is characterized by a reduction of dopamine levels in the striatum.[10] At physiological pH dopamine is almost completely ionized, resulting in low permeation across the blood brain barrier and precluding it as a direct treatment for Parkinson's disease.

Conjugation to lipophilic molecules, such as docosahexaenoic acid (DHA), may assist dopamine's uptake by the brain. The prodrug DHA-dopamine[29] was demonstrated to have a brain penetration index of 30%, comparable with that of D-glucose (33%). Catechols exhibit other important chemical properties including chelation of various metal ions and remarkable interfacial chemical properties.[7] As a result, there is increasing interest in exploiting catechols and catechol derivatized polymers as surface coatings.[30] Several recent reports describe the conjugation of dopamine to small molecule initiators and polymers, obtained through reaction of the amino group of dopamine to form a peptide bond.[30,31.]

One of the challenges in conjugating dopamine is that it is readily oxidized, especially under basic conditions, to dopamine quinone, which undergoes self-polymerization or nucleophilic addition reactions with amino or sulfhydryl group.[32] Proper protection of the catechol group is required during chemical modification of dopamine.

Direct protection of a catecholamine by acetonide is not easily accomplished by refluxing with acetone or its ketal 2,2-dimethoxypropane (DMP) in the presence of a catalyst, e.g., p-toluenesulfonic acid (TsOH). Such acetonide compounds as 1-(2,2-dimethylbenzo[1,3]dioxol-5-yl)propan-2-amine are usually obtained by a complicated method involving construction of the target molecule from an acetonide-protected catechol subunit, introduction of a nitro group by a nitration reagent such as nitroethane, and reduction of the $-NO_2$ to $-NH_2$ group with lithium aluminum hydride.[36] One of the possible side reactions during direct acetonide protection of dopamine is that, as a beta phenylamine, dopamine readily undergoes Pictet-Spengler condensations with aldehydes and ketones to produce tetrahydroisoquinolines.[37] Further, the conventional methods of producing acetonide-protected DOPA result in a racemic mixture, requiring additional costly and complicated purification steps.

Thus there is a need in the art for a simpler, cost-effective method for synthesizing acetonide-protected, catechol-containing compounds such as DOPA and dopamine.

DMP, TsOH, benzene, reflux, 83%; (d) H2NNH2,DCM/ MeOH, 56%; (e) LiOH, THF/H2O; (f) Fmoc-Osu,74% (e and f).

Figure 2:
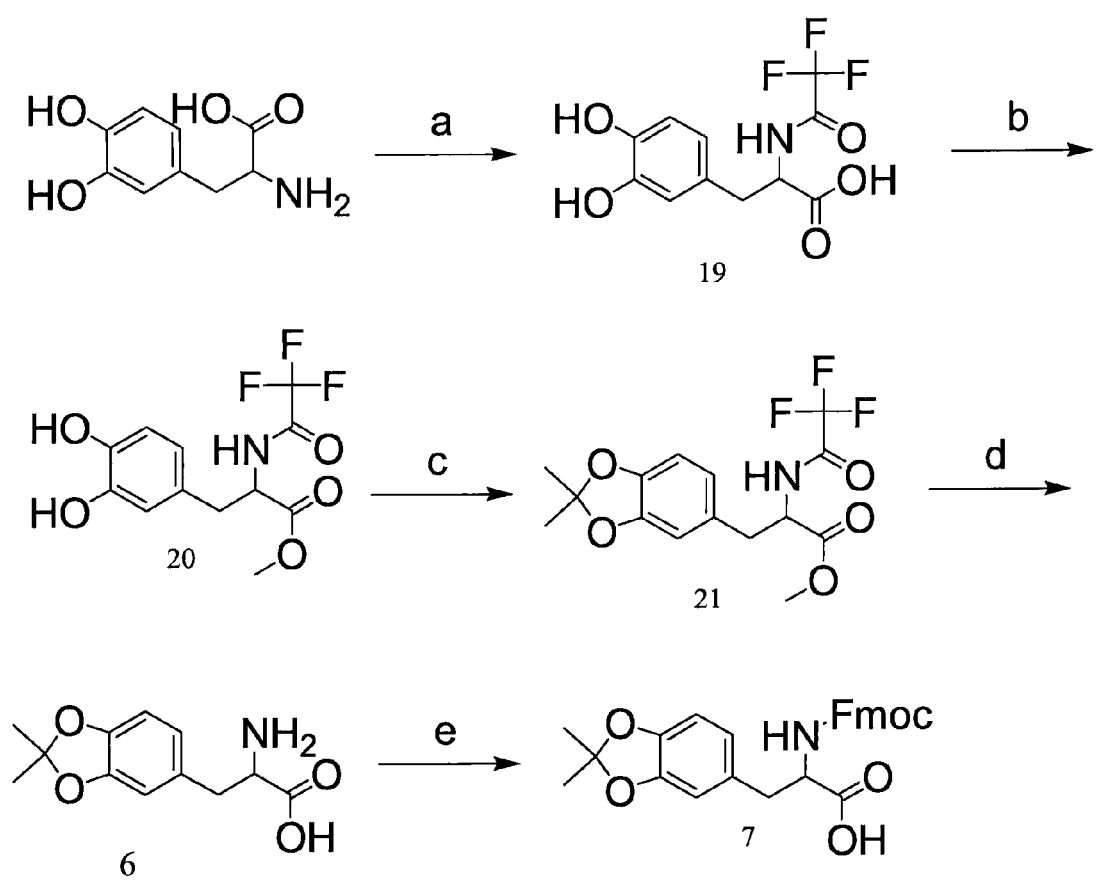

FIG. 2. Synthesis of Fmoc-DOPA(acetonide)-OH and intermediates.

Figure 3:
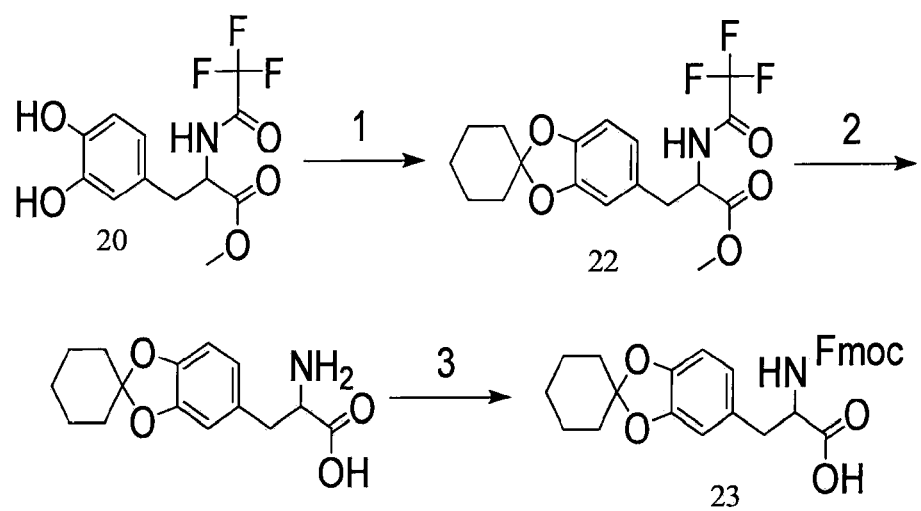

FIG. 3. Synthesis of Fmoc-DOPA(Chex)-OH (23)

Figure 4:
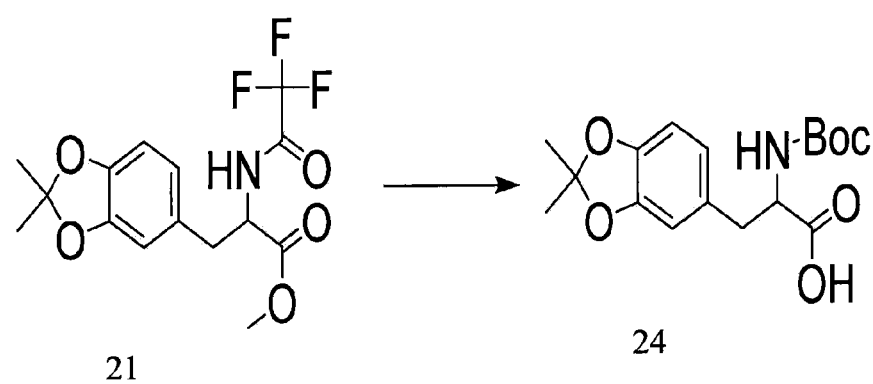

FIG. 4. Synthesis of Boc-DOPA(acetonide)-OH (24).

Figure 5:
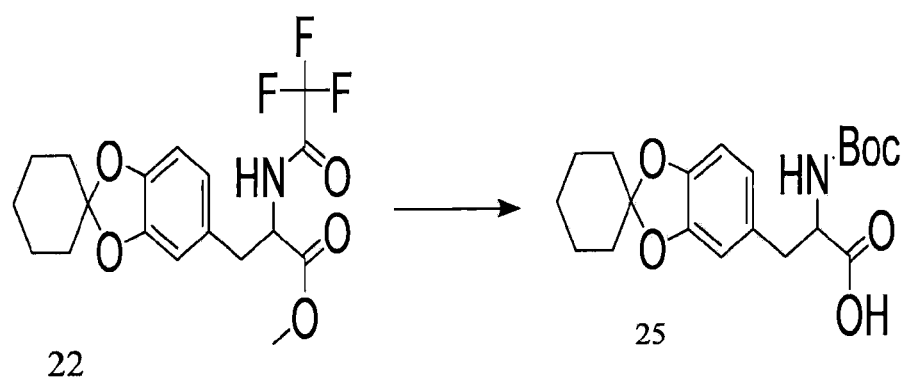

FIG. 5. Synthesis of Boc-DOPA(Chex)-OH (25).

Figure 6:
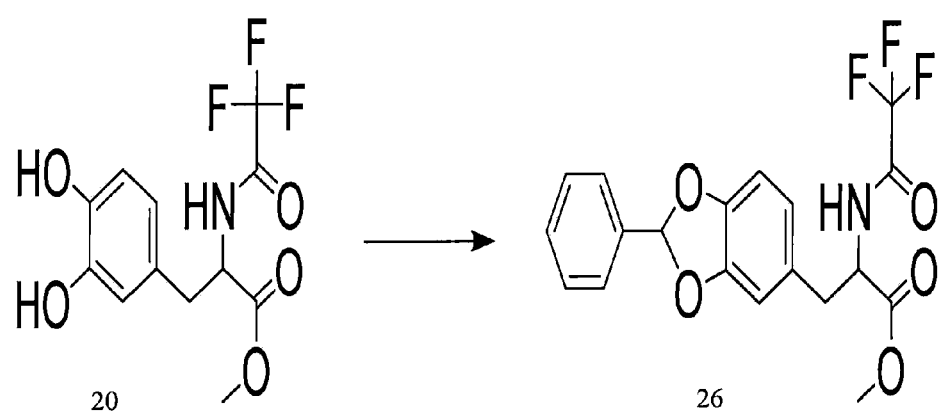

FIG. 6. Synthesis of TFA-DOPA(BA)-OMe (26).

Figure 7:
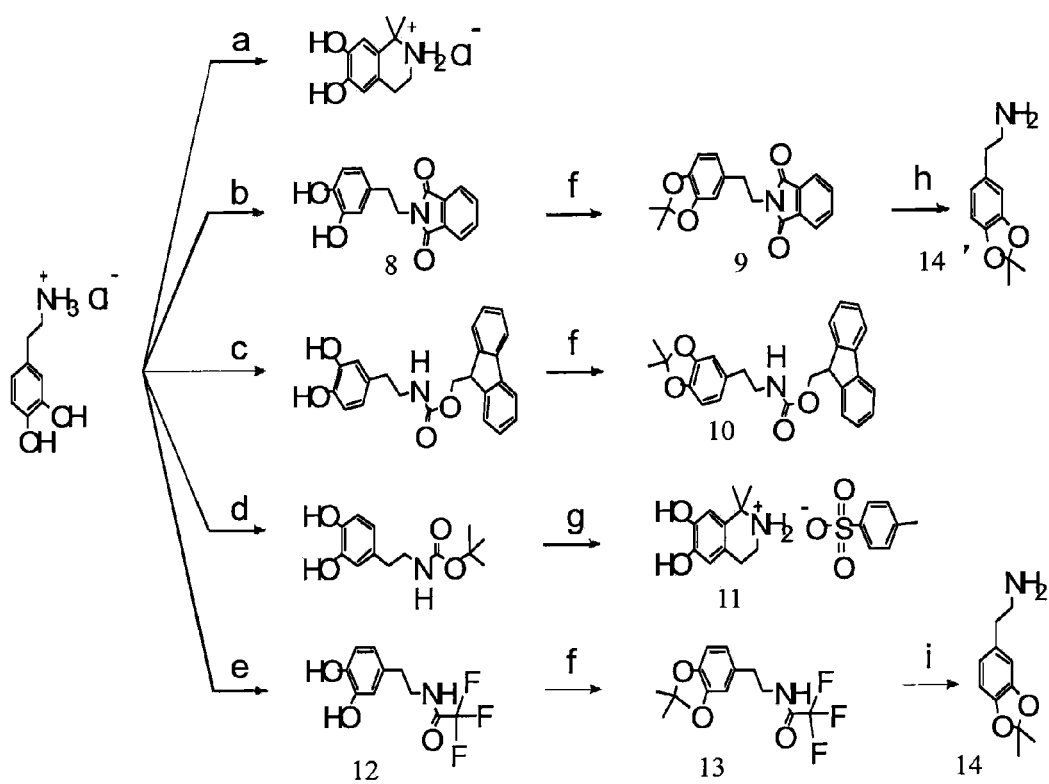

FIG. 7. Synthesis of acetonide-protected dopamine (14) and intermediates. Reagents and conditions: (a), reference[40]; (b), N-carbethoxyphthalimide, Et$_3$N, 74%; (c), reference[41]; (d), reference[42]; (e), CF$_3$COOMe, Et$_3$N in MeOH, 98%; (f), DMP, TsOH (4.5%), benzene, reflux, yield, 95% (8), 90% (9), 89% (12); (g), DMP, TsOH (1.05 equiv), benzene, reflux, >10%; (h), H$_2$NNH$_2$, DCM, 97%; (i), LiOH, THF/H$_2$O, 87%.

Figure 8:
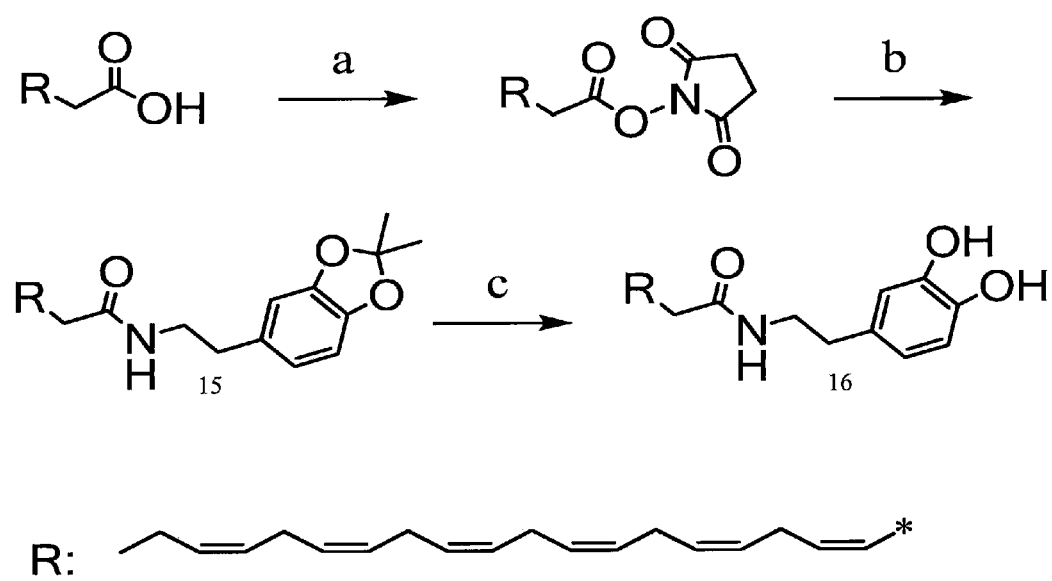

FIG. 8. Synthesis of DHA-dopamine(16). Reagents and conditions: (a), DCC/NHS; (b), dopamine(acetonide), 68% (two steps); (c), 25% trifluoroacetic acid in CHCl$_3$/H$_2$O, 100%.

Figure 9:
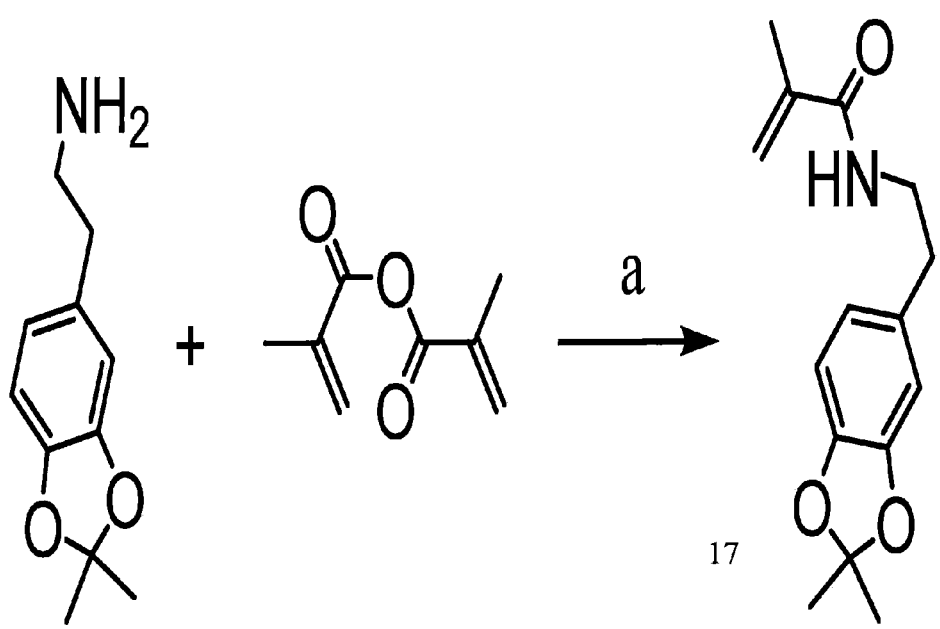

FIG. 9. Synthesis of catechol-containing polymers using dopamine(acetonide) (14). Reagents and conditions: (a), DCM, DIPEA, 93%.

Figure 10:
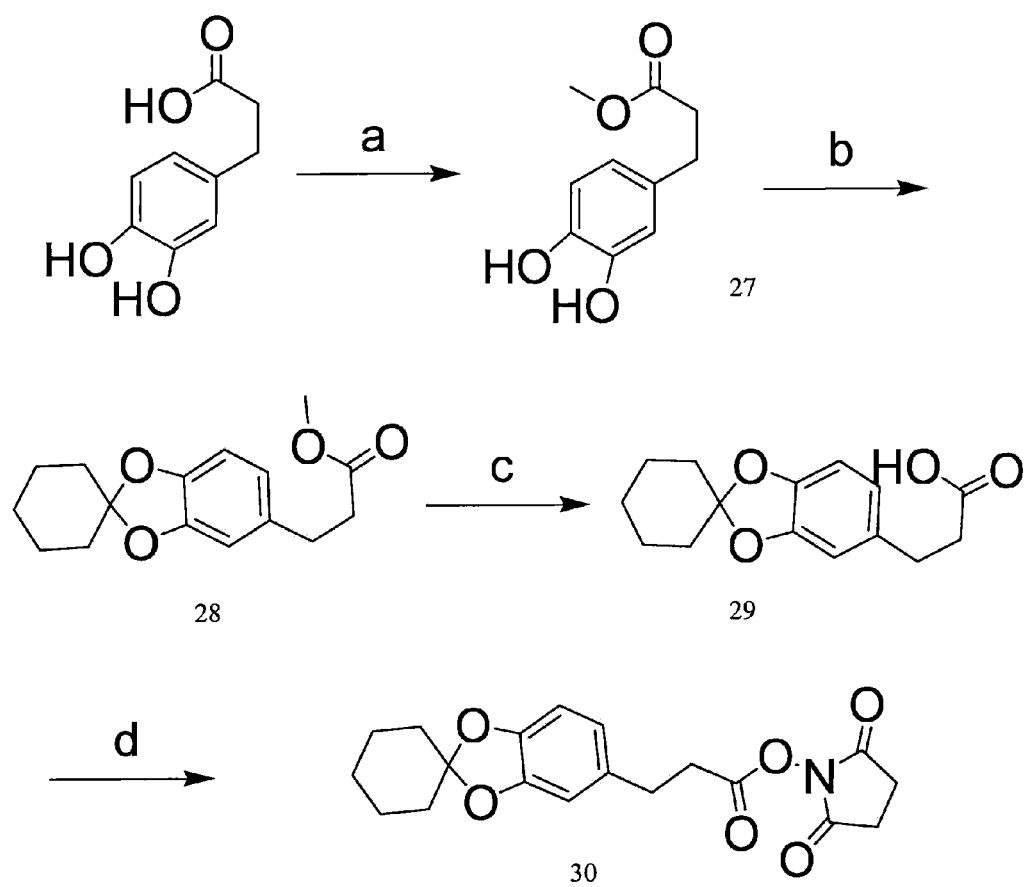

FIG. 10. Synthesis of DHCA(Chex)-OSu (30).

Figure 11:
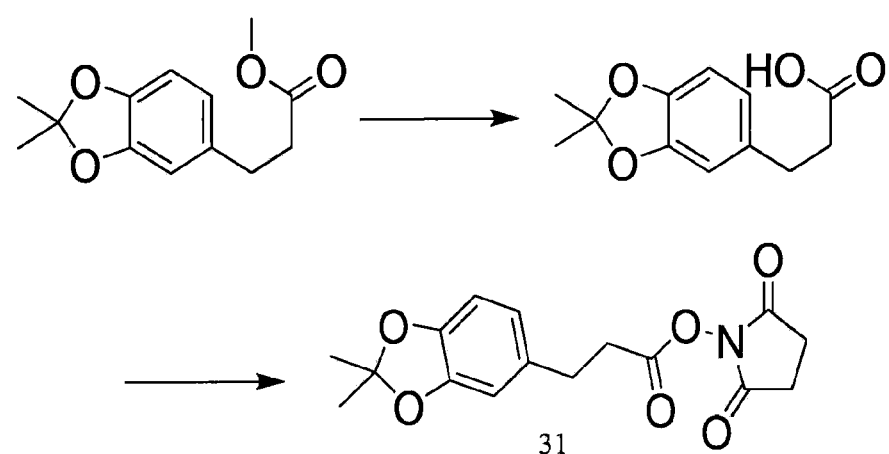

FIG. 11. Synthesis of DHCA(acetonide)-OSu (31)

FIG. 12. Ferric Chloride test results.

Figure 13:
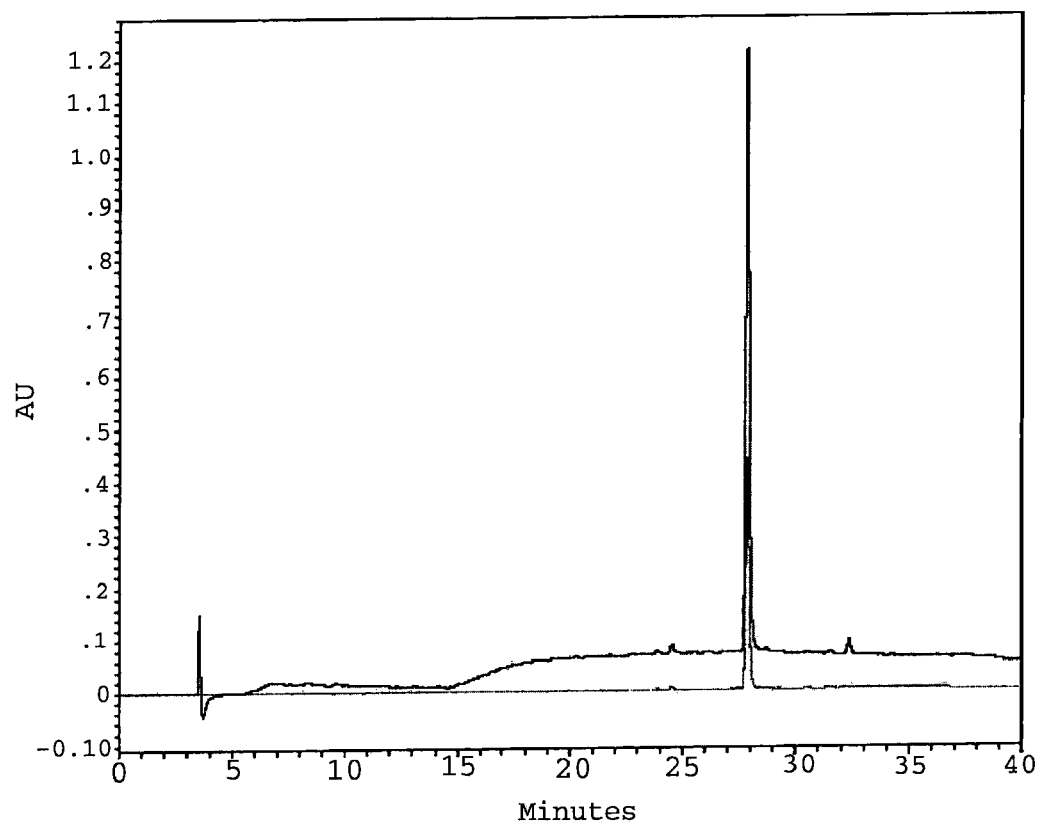

FIG. 13. RP-HPLC of Fmoc-DOPA(acetonide)-Gly-Gly-Lys(Boc)-Lys(Boc)-OH. Elution method: a linear gradient 0-100% Solvent B (v/v) over 30 min, and then a constant 100% Solvent B for 10 min, at a flow rate of 1.0 mL/min. Red line: UV detection at 215 nm. Green line: UV detection at 280 nm.

Figure 14:
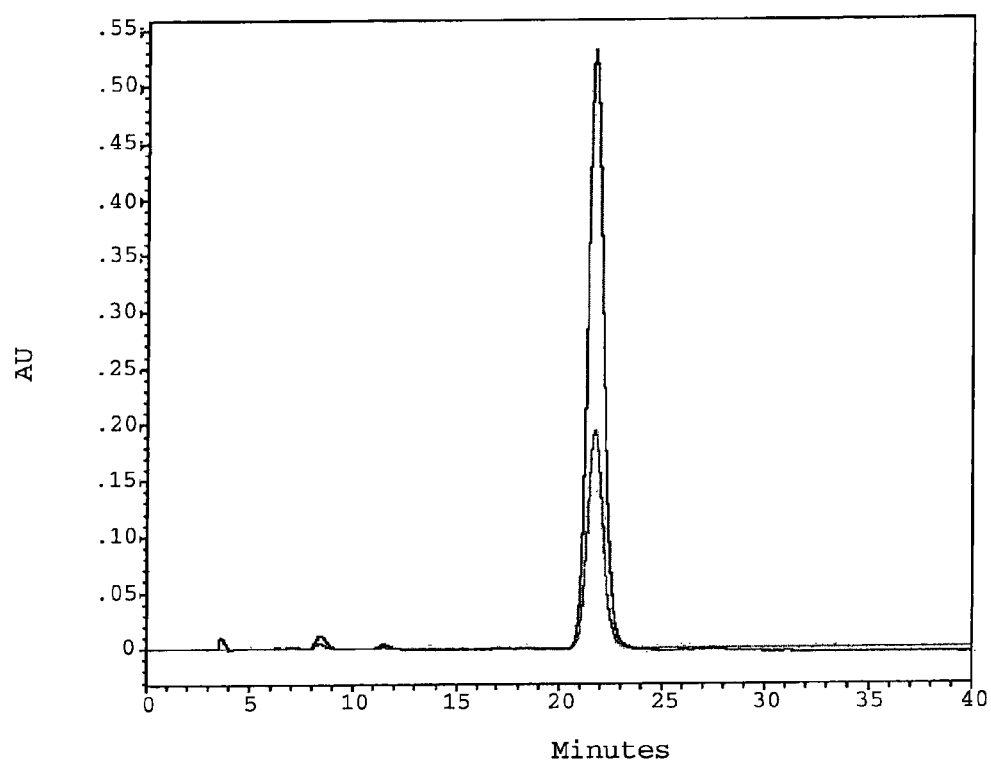

FIG. 14. RP-HPLC of Fmoc-DOPA(acetonide)-Gly-Gly-Lys(Boc)-Lys(Boc)-OH. Elution method: a linear gradient 56-64% Solvent B (v/v) over 40 min at a flow rate of 1.0 mL/min. Red line: UV detection at 215 nm. Green line: UV detection at 280 nm.

Figure 15:
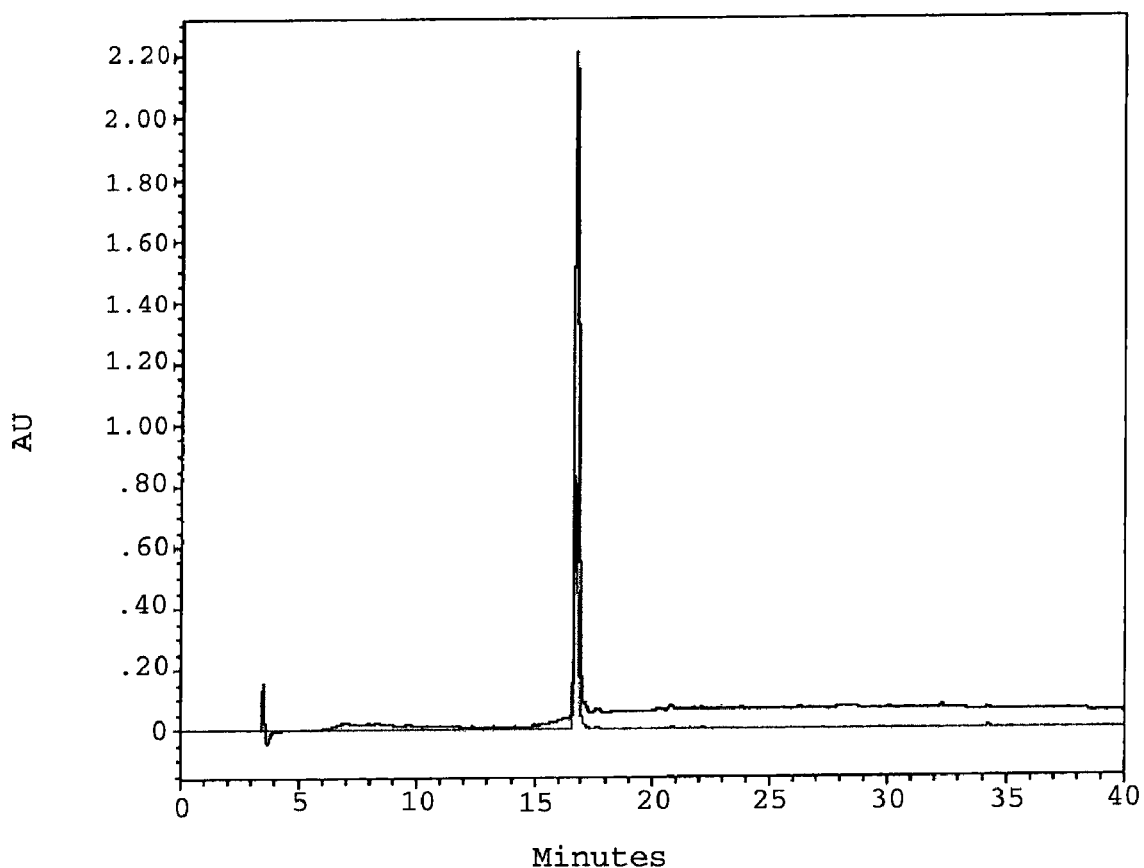

FIG. 15. RP-HPLC of Fmoc-DOPA-Gly-Gly-Lys-Lys-OH. Elution method: a linear gradient 0-100% Solvent B (v/v) over 30 min, and then a constant 100% Solvent B for 10 min, at a flow rate of 1.0 mL/min. Red line: UV detection at 215 nm. Green line: UV detection at 280 nm.

Figure 16:
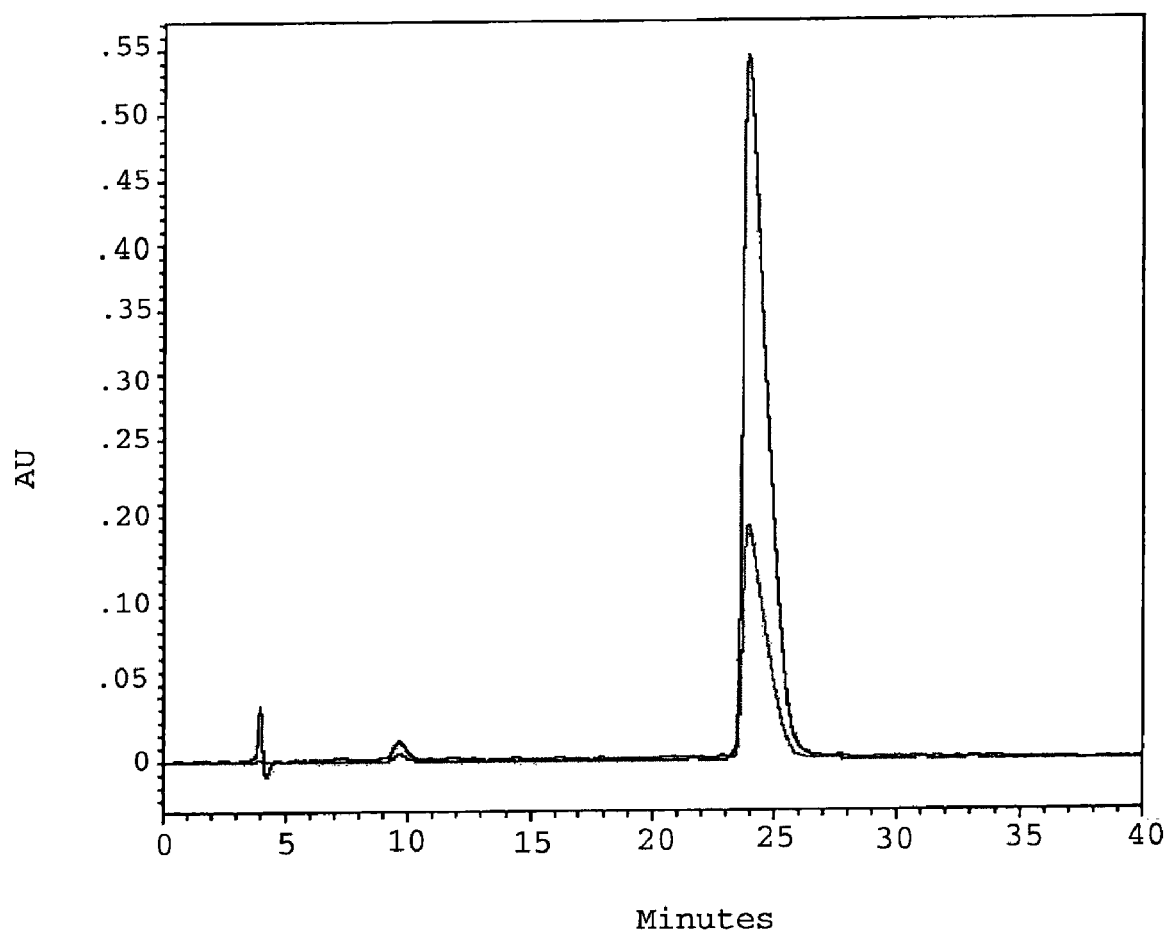

FIG. 16. RP-HPLC of Fmoc-DOPA-Gly-Gly-Lys-Lys-OH. Elution method: a linear gradient 23-31% Solvent B (v/v) over 40 min at a flow rate of 1.0 mL/min. Red line: UV detection at 215 nm. Green line: UV detection at 280 nm.

Figure 17:
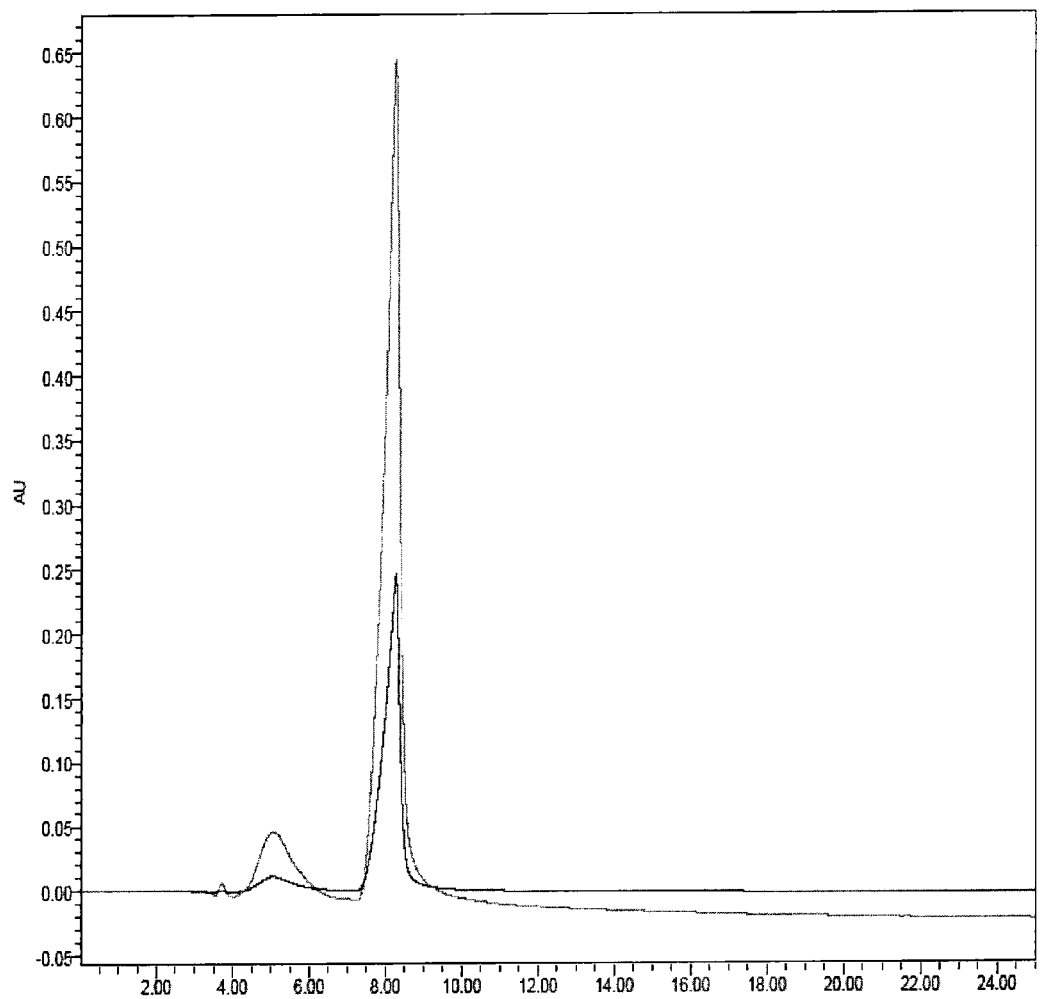

FIG. 17. Chiral-HPLC Analysis: L-DOPA (reference). Red line: UV detection at 215 nm. Green line: UV detection at 280 nm.

Figure 18:
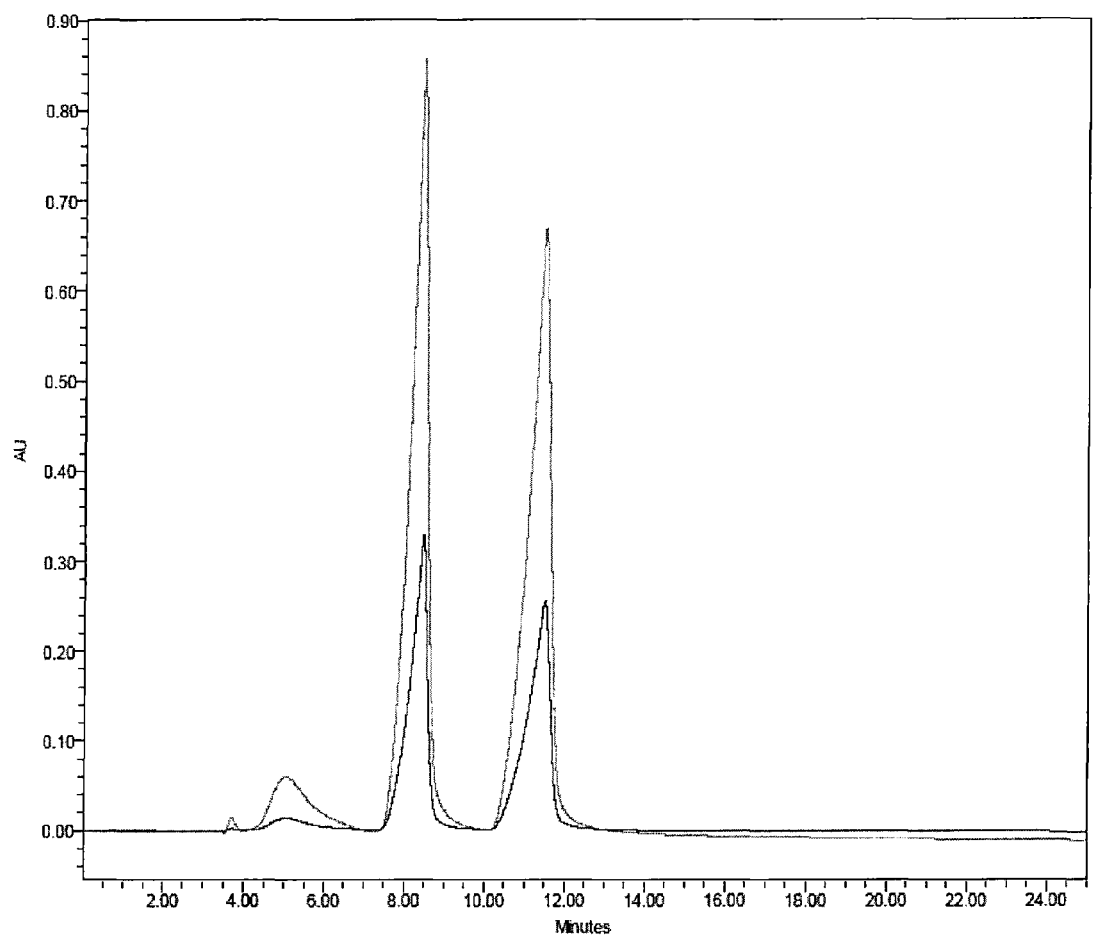

FIG. 18. Chiral-HPLC Analysis:D-/L-DOPA (reference). Red line: UV detection at 215 nm Green line: UV detection at 280 nm.

Figure 19:
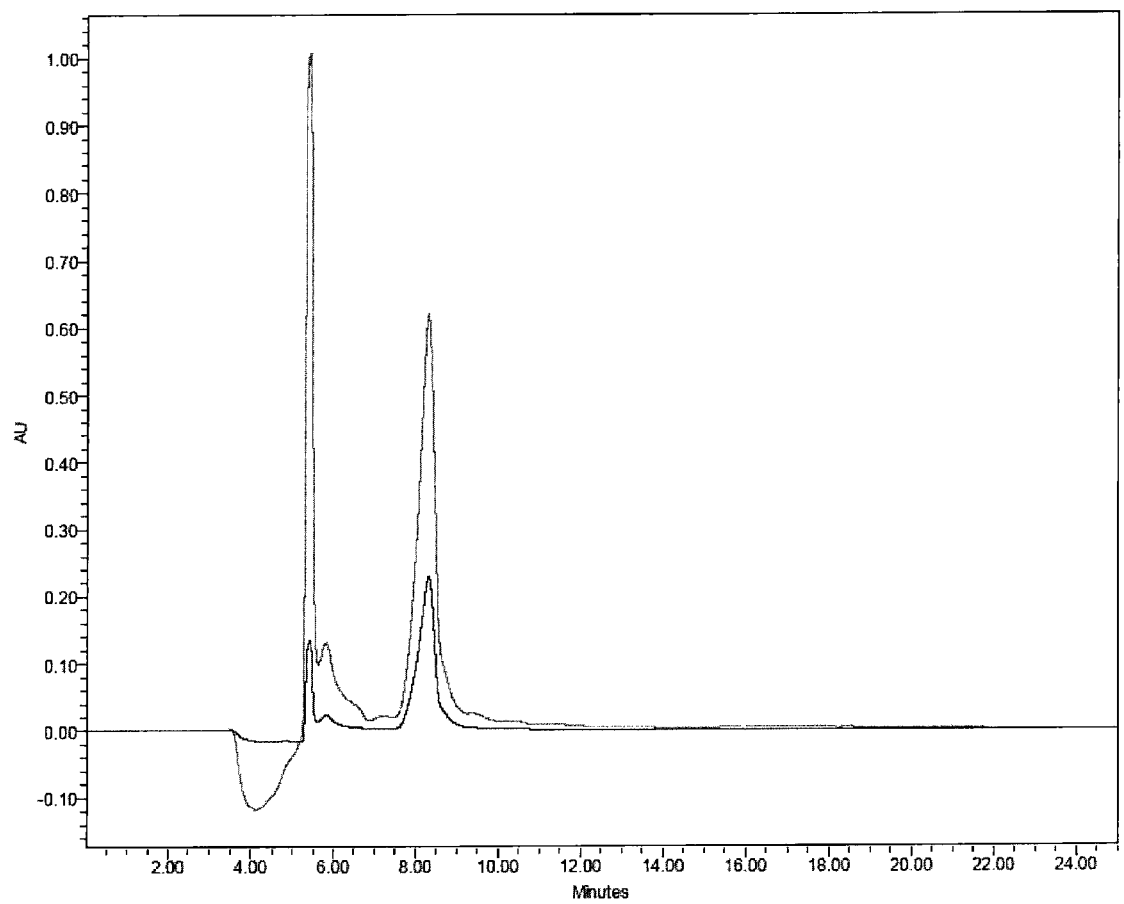

FIG. 19. Chiral-HPLC Analysis: Fmoc-DOPA(acetonide)-OH (7).

Figure 20:
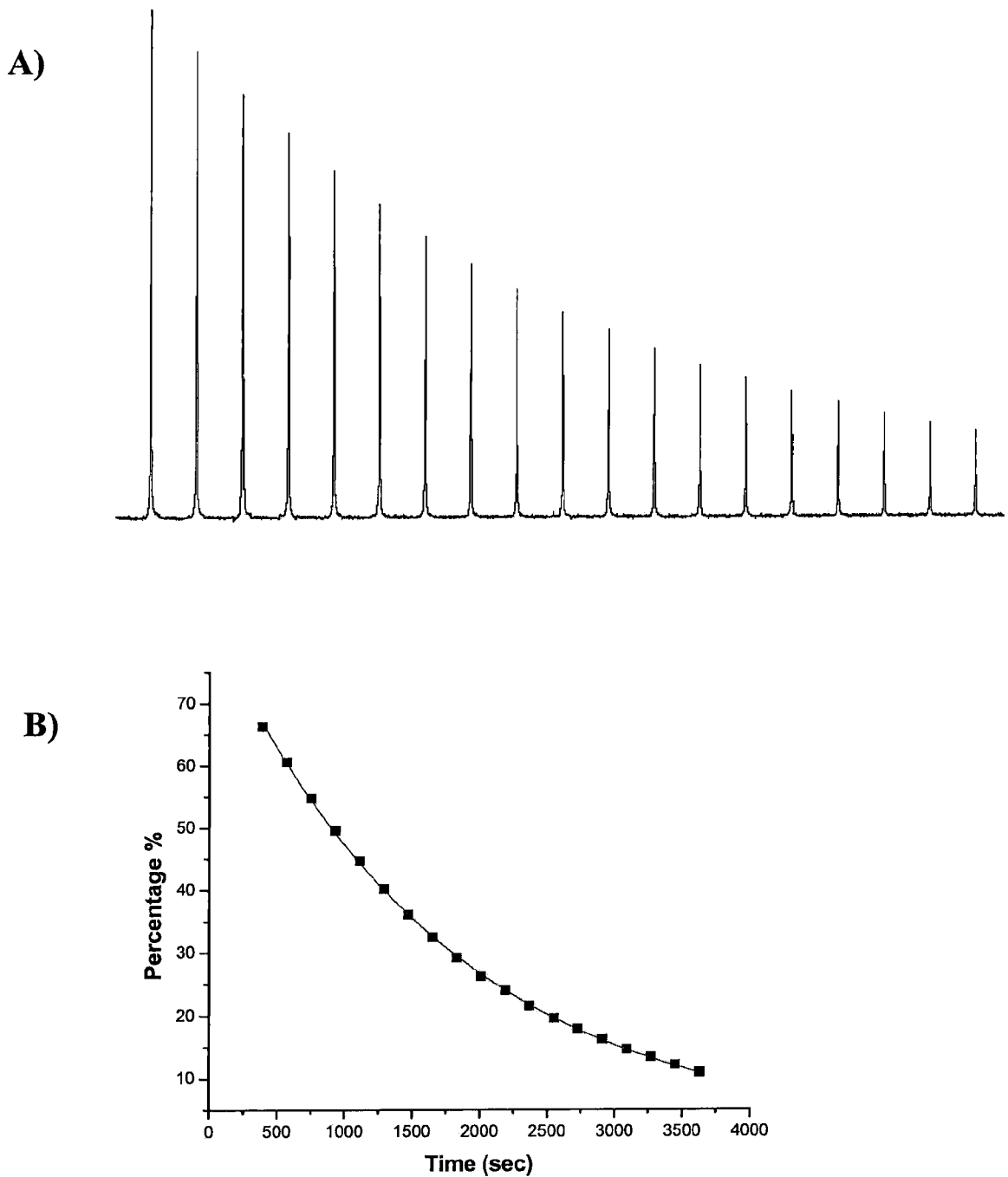

FIG. 20. NMR array experiment of acetonide deprotection of TFA-dopamine(acetonide) in 70% trifluoroacetic acid DMSO-d$_6$ solution with 2.5% TIS and 2.5% H$_2$O. A) Array of the decreasing intensities of the methyl protons of the acetonide group. B) Fitting of the date with first order decay model.

FIG. 21. Phth-DOPA(acetonide)-OMe.

FIG. 22. Phth-DOPA(acetonide)-OMe (4). $^1$H NMR (500 MHz, CDCl$_3$).

Figure 23:
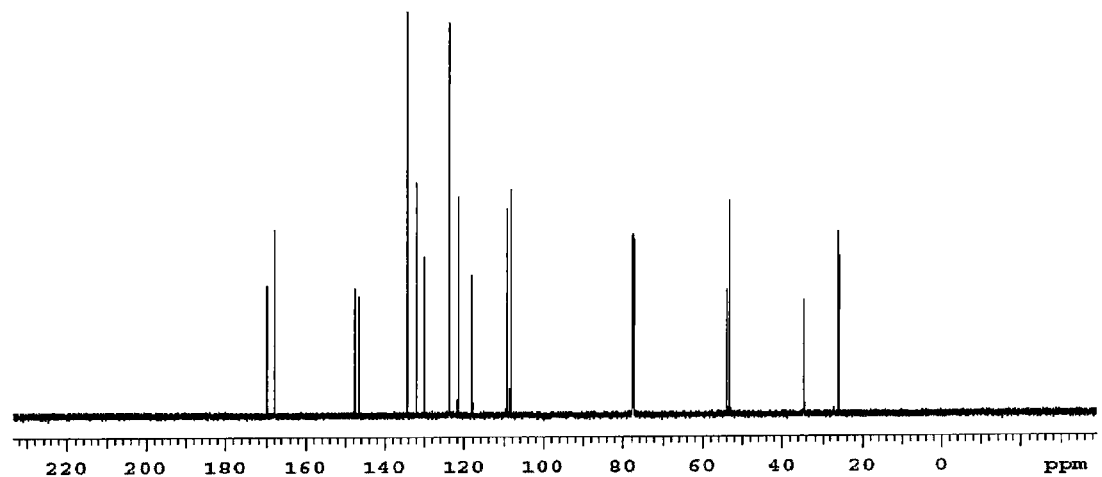

FIG. 23. Phth-DOPA(acetonide)-OMe (4). $^{13}$C NMR (125 MHz, CDCl$_3$).

FIG. 24. H-DOPA(acetonide)-OMe (5a). $^1$H NMR (500 MHz, CDCl$_3$).

Figure 25:
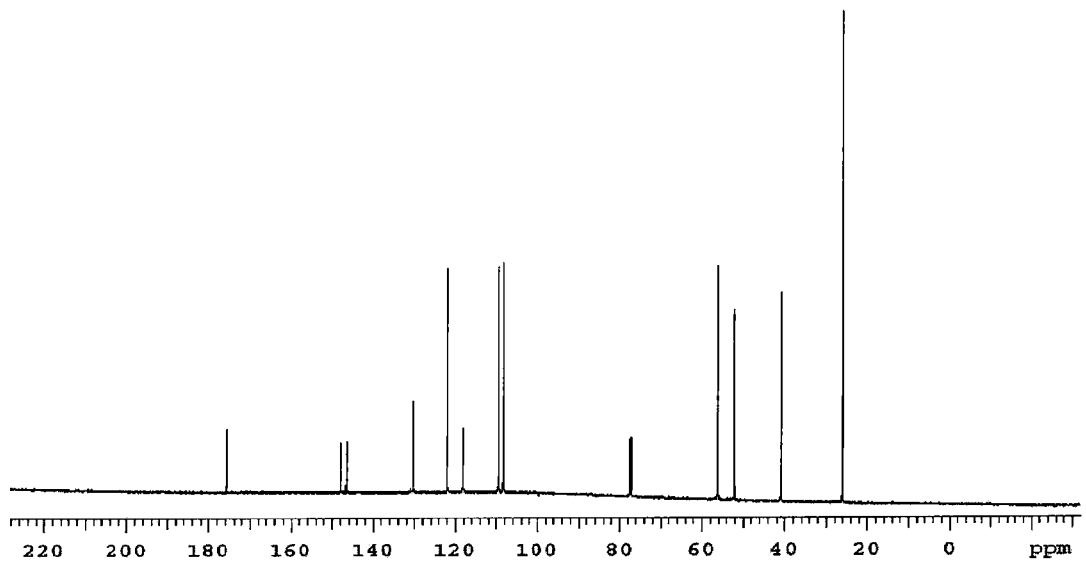

FIG. 25. H-DOPA(acetonide)-OMe (5a). $^{13}$C NMR (125 MHz, CDCl$_3$).

Figure 26:
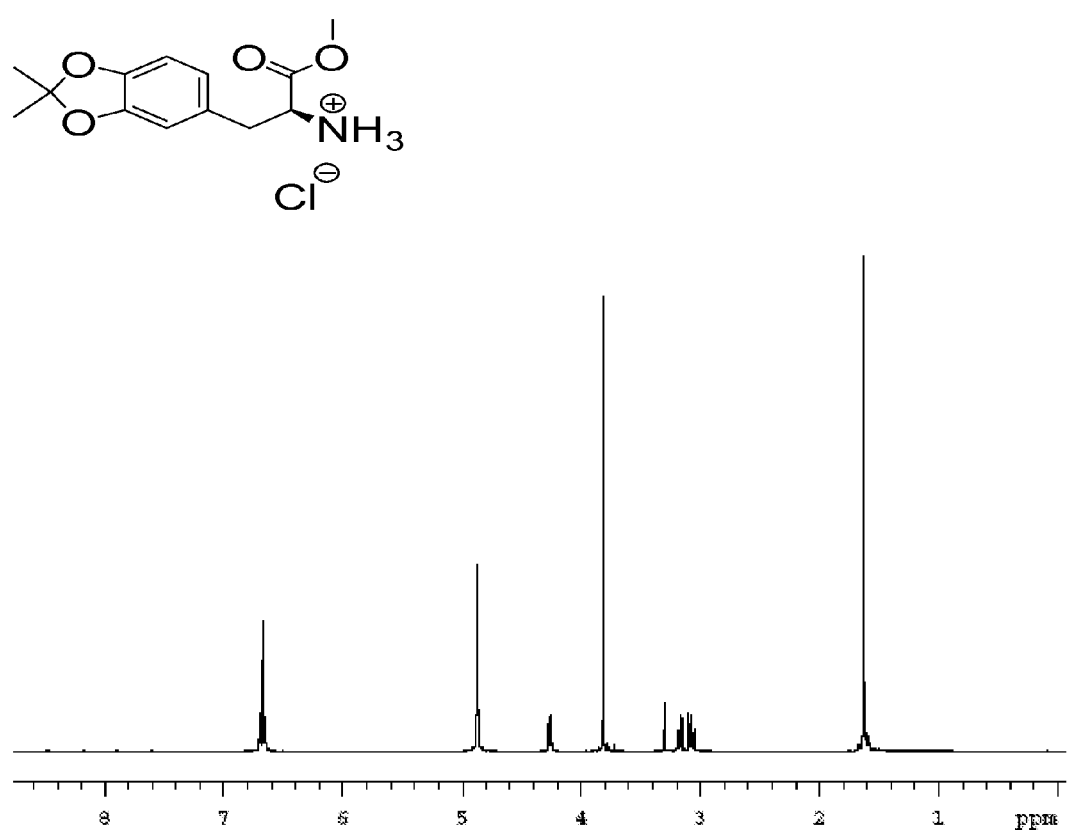

FIG. 26. Hydrochloride Salt of H-DOPA(acetonide)-OH (5b). $^1$H NMR (500 MHz, CD$_3$OD).

Figure 27:
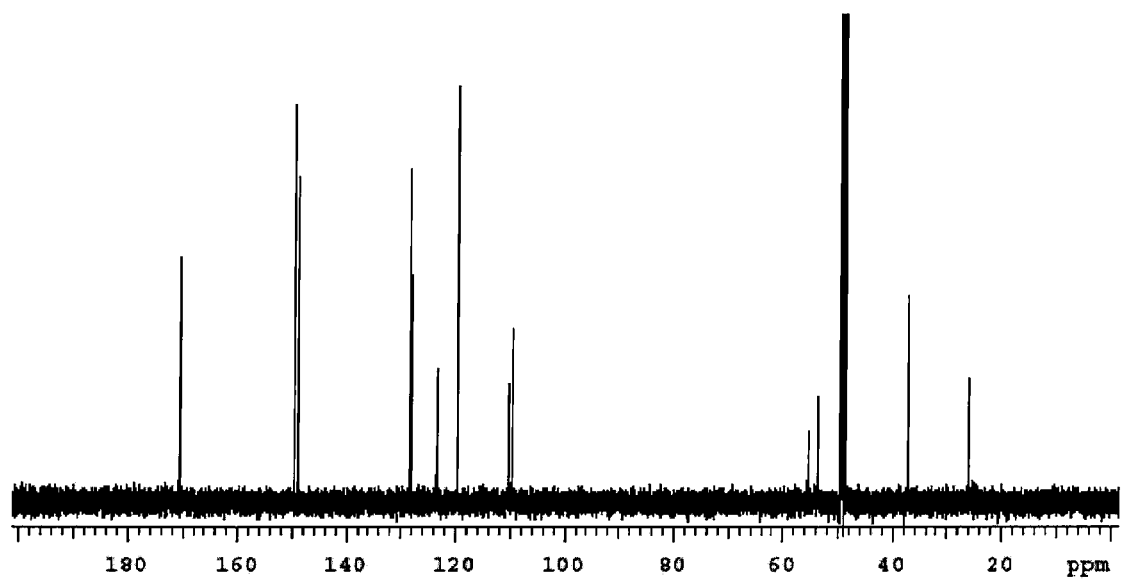

FIG. 27. Hydrochloride Salt of H-DOPA(acetonide)-OH (5b). $^{13}$C NMR (125 MHz, CD$_3$OD).

Figure 28:
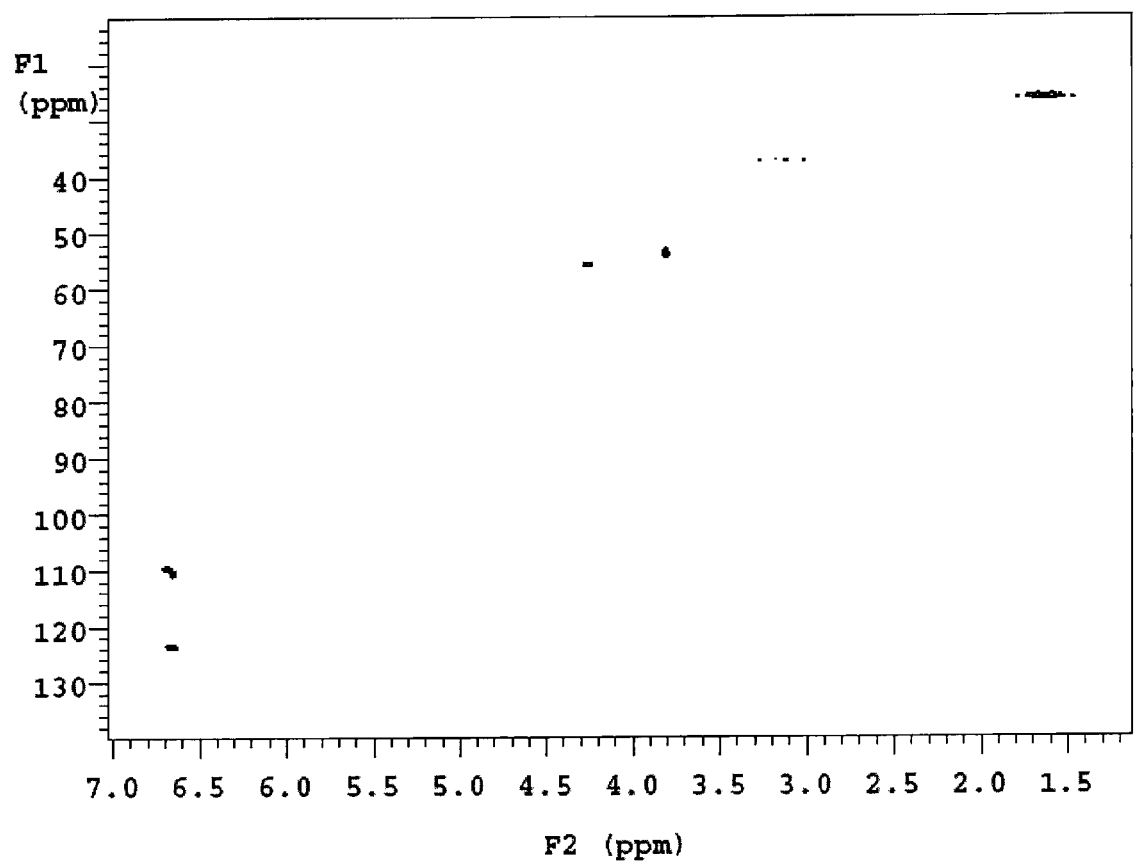

FIG. 28. Hydrochloride Salt of H-DOPA(acetonide)-OH (5b). HMQC (500 MHz, CD$_3$OD).

Figure 29:
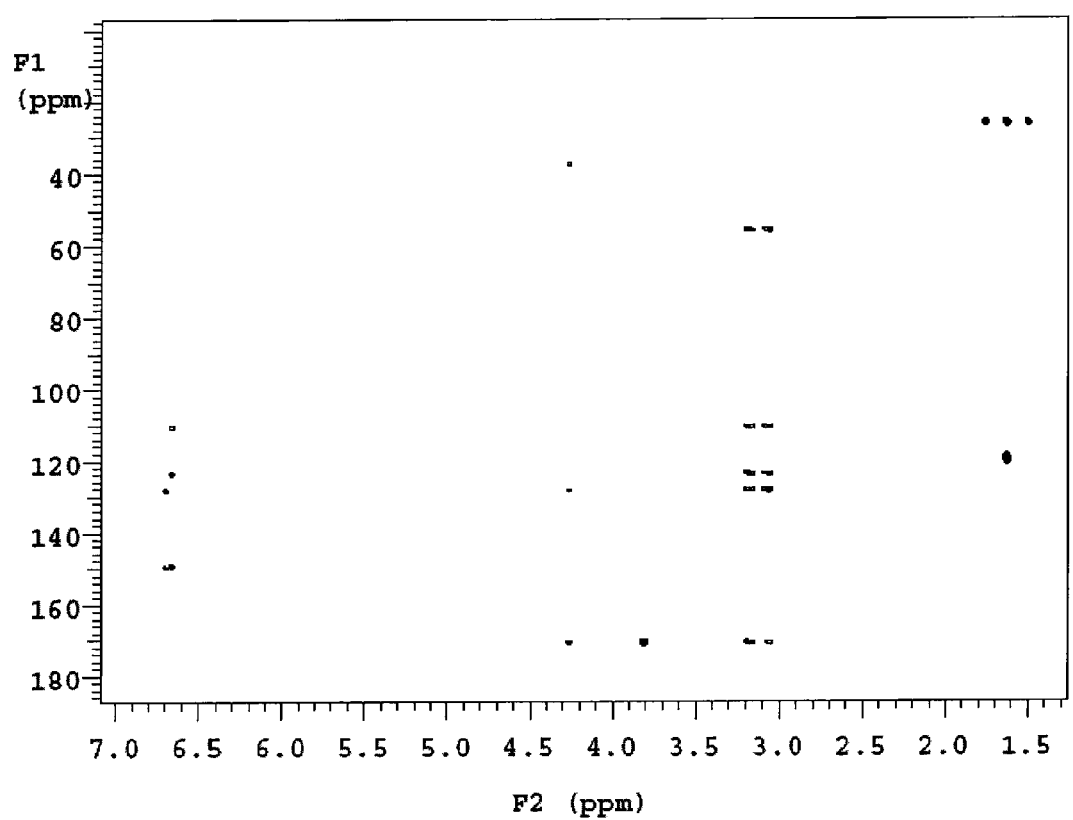

FIG. 29. Hydrochloride Salt of H-DOPA(acetonide)-OH (5b). HMBC (500 MHz, CD$_3$OD).

Figure 30:
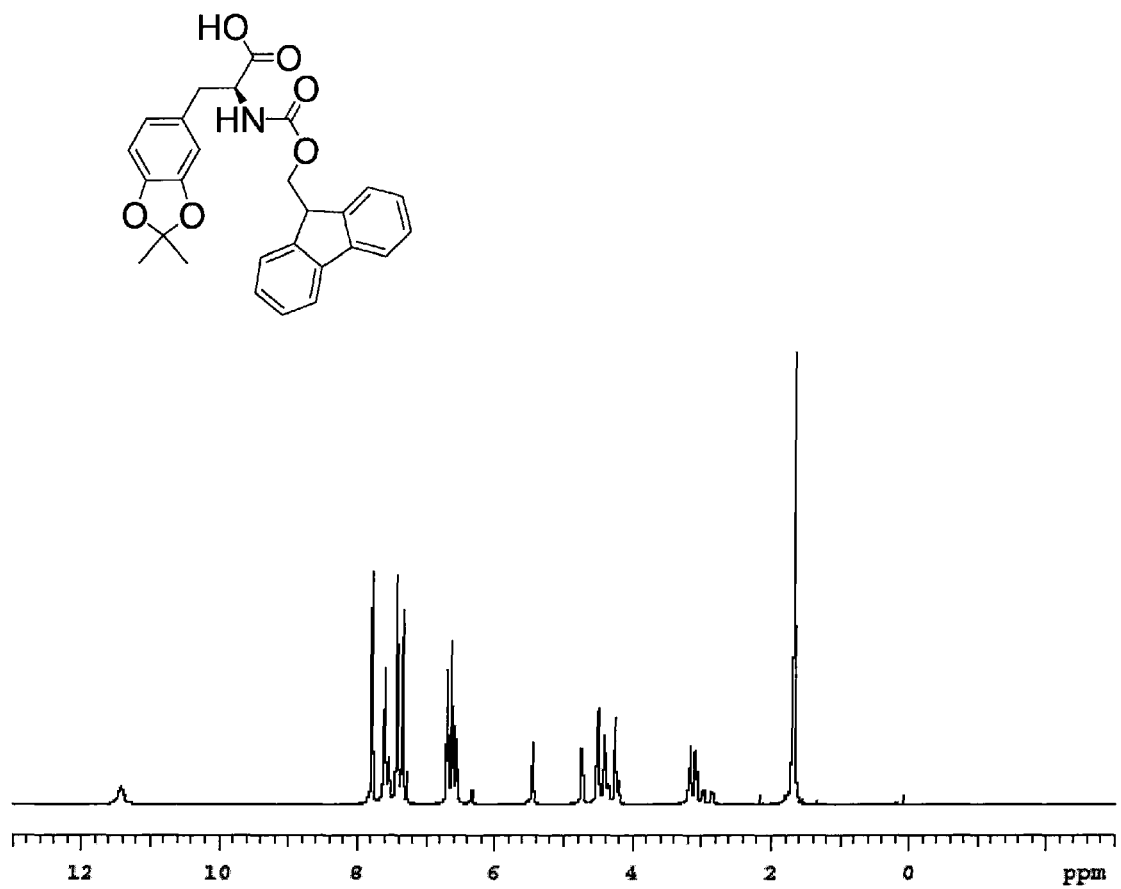

FIG. 30. Fmoc-DOPA(acetonide)-OH (7). $^1$H NMR (500 MHz, CDCl$_3$).

Figure 31:
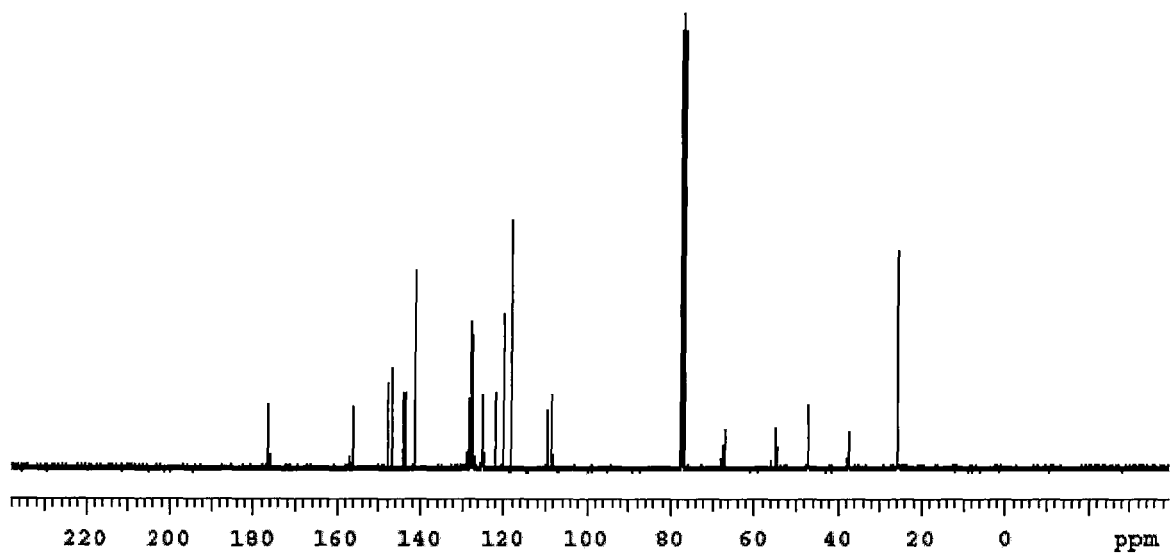

FIG. 31. Fmoc-DOPA(acetonide)-OH (7). $^{13}$C NMR (125 MHz, CDCl$_3$).

Figure 32:
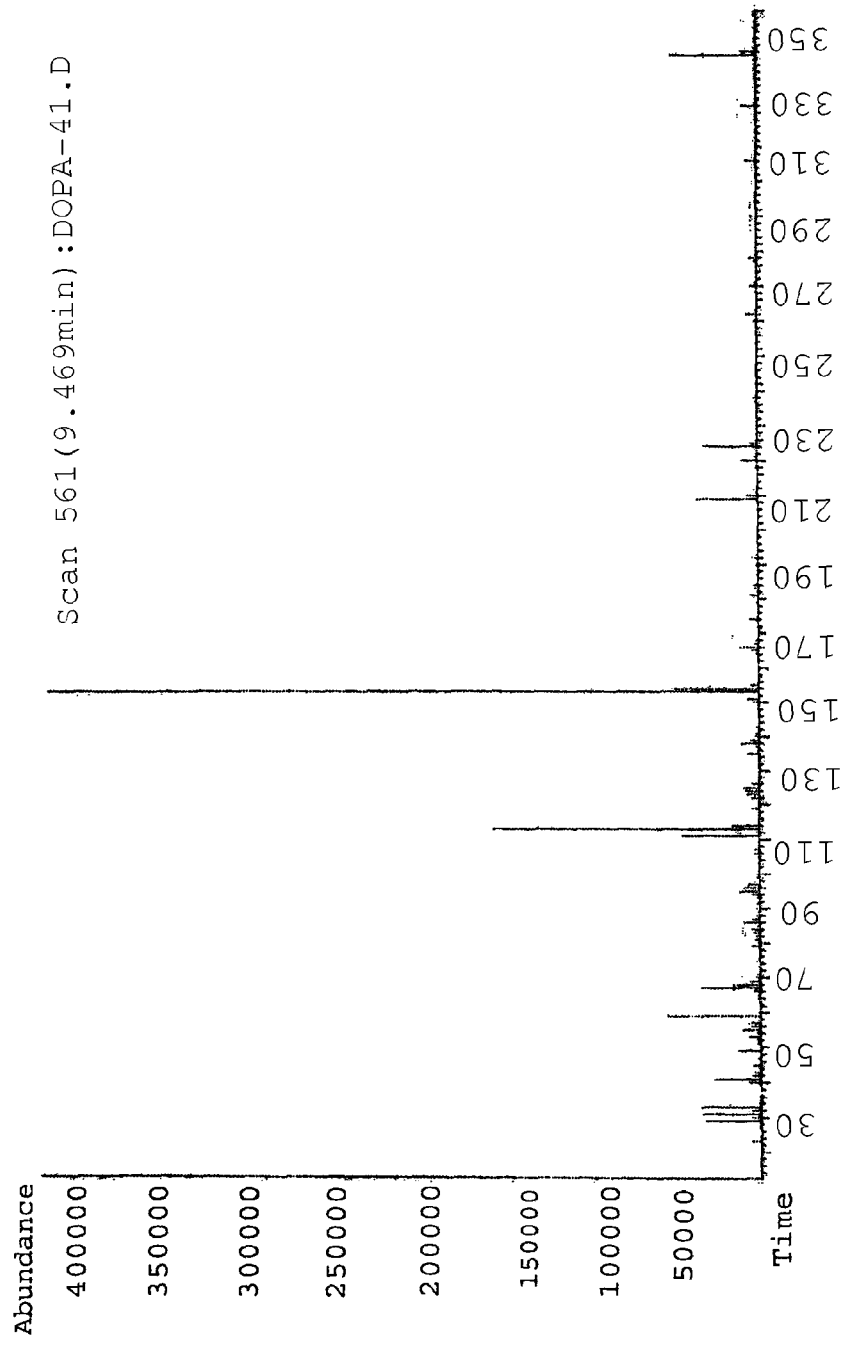

FIG. 32. TFA-DOPA(acetonide)-OMe.

FIG. 33. TFA-DOPA(acetonide)-OMe $^1$H NMR (500 MHz, CDCl$_3$).

Figure 34:
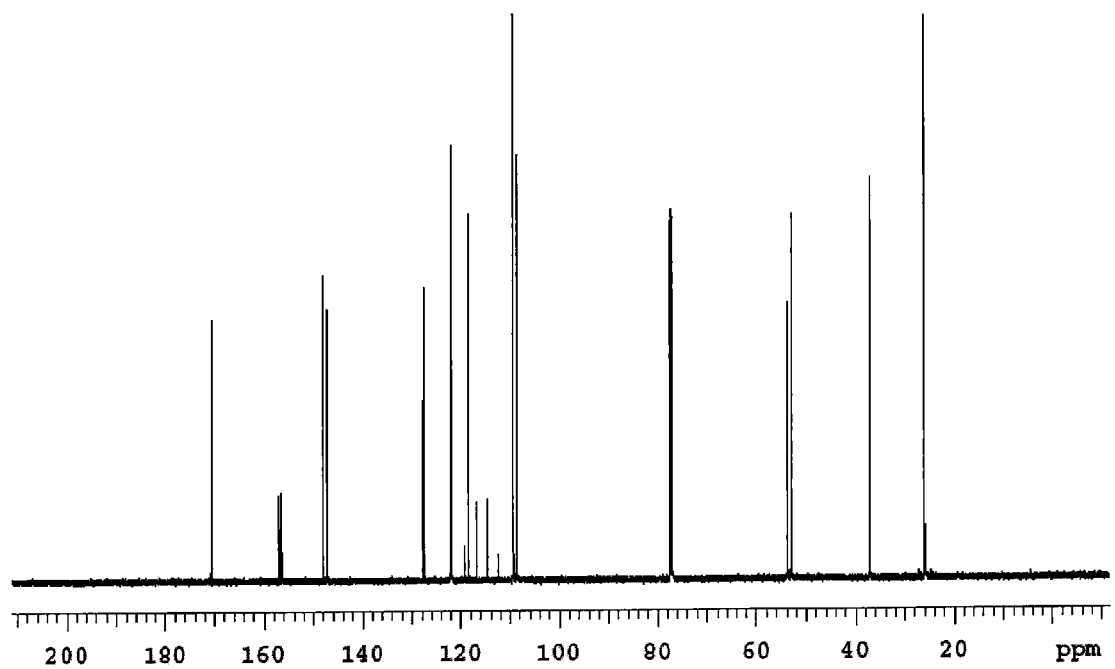

FIG. 34. TFA-DOPA(acetonide)-OMe $^{13}$C NMR (125 MHz, CDCl$_3$).

Figure 35:
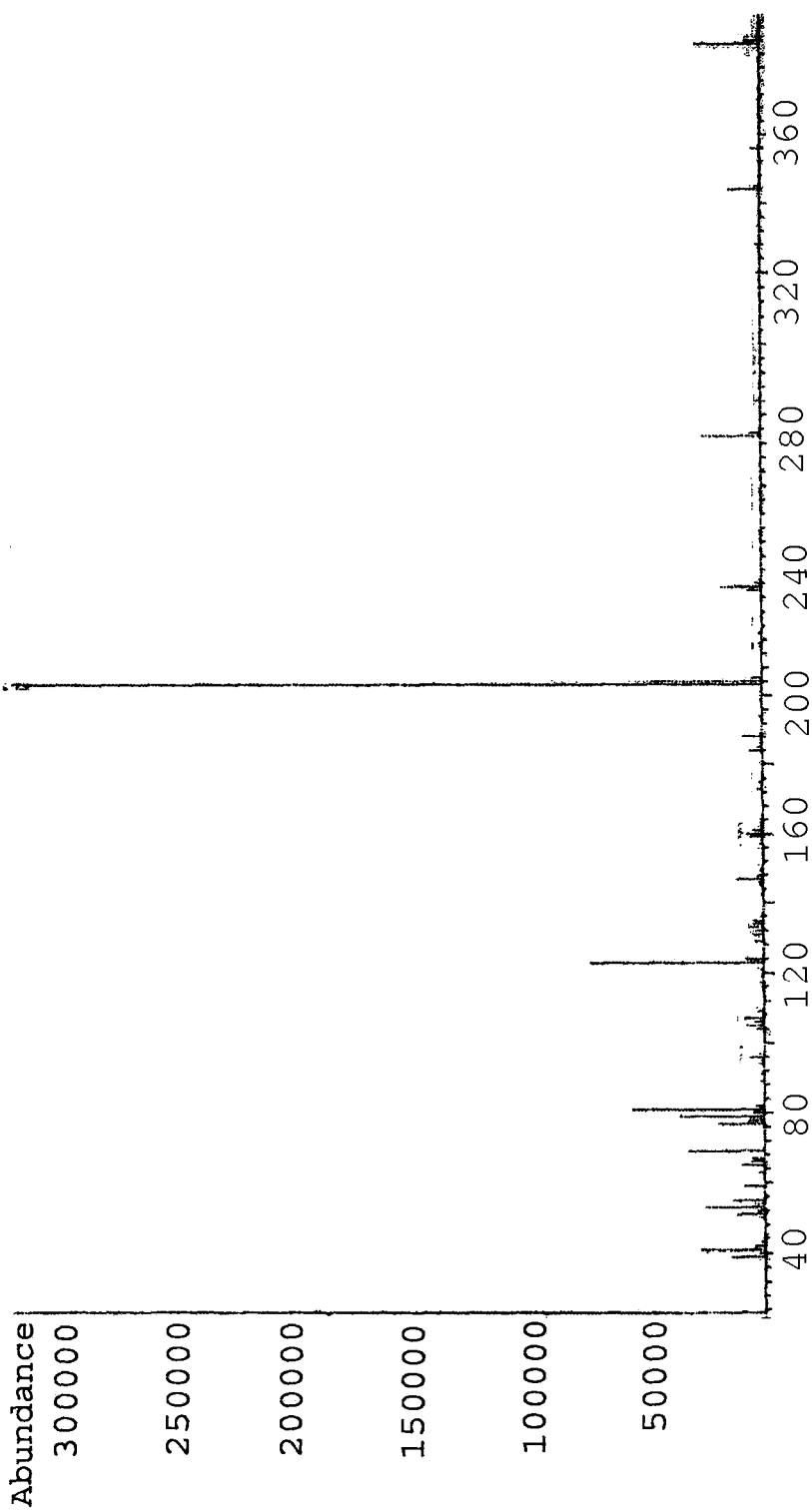

FIG. 35. TFA-DOPA(Chex)-OMe.

Figure 36:
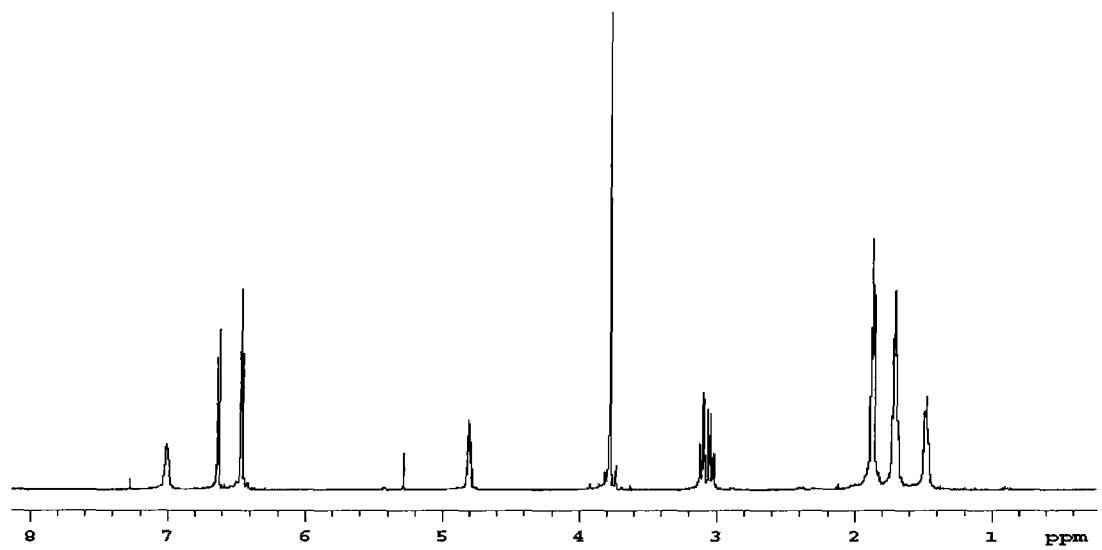

FIG. 36. TFA-DOPA(Chex)-OMe $^1$H NMR (500 MHz, CDCl$_3$).

Figure 37:
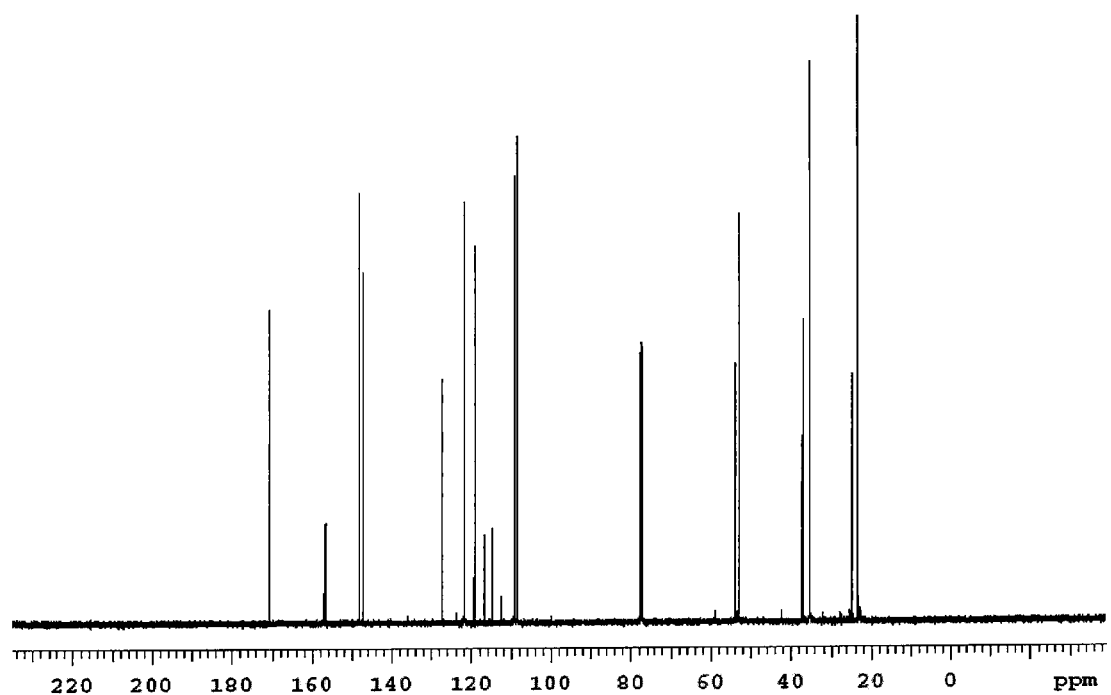

FIG. 37. TFA-DOPA(Chex)-OMe $^{13}$C NMR (125 MHz, CDCl$_3$).

FIG. 38. TFA-DOPA(BA)-OMe $^1$H NMR (500 MHz, CDCl$_3$).

Figure 39:
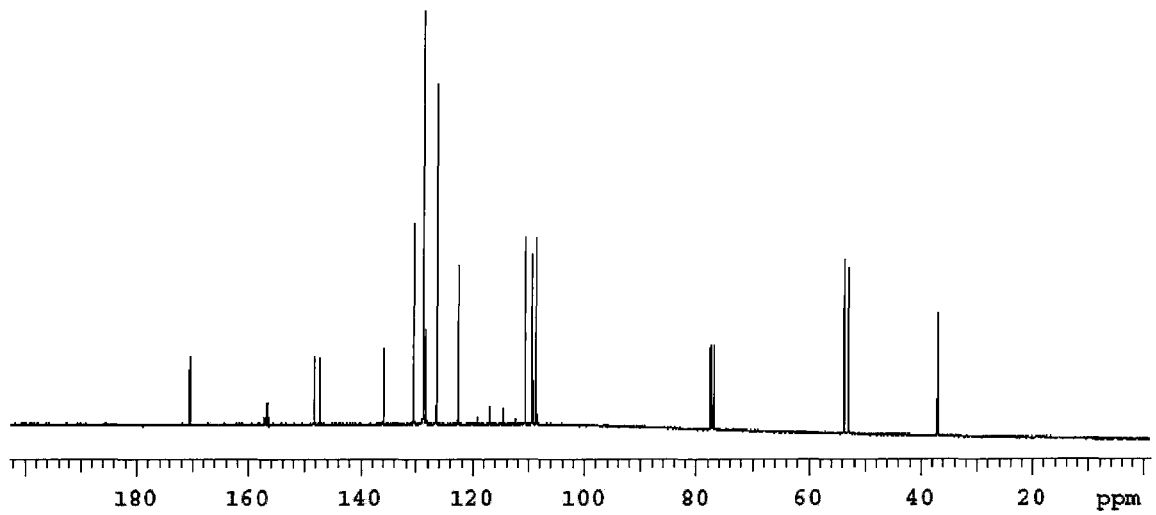

FIG. 39. TFA-DOPA(BA)-OMe $^{13}$C NMR (125 MHz, CDCl$_3$).

FIG. 40. Fmoc-DOPA(Chex)-OH $^1$H NMR (500 MHz, CDCl$_3$).

Figure 41:
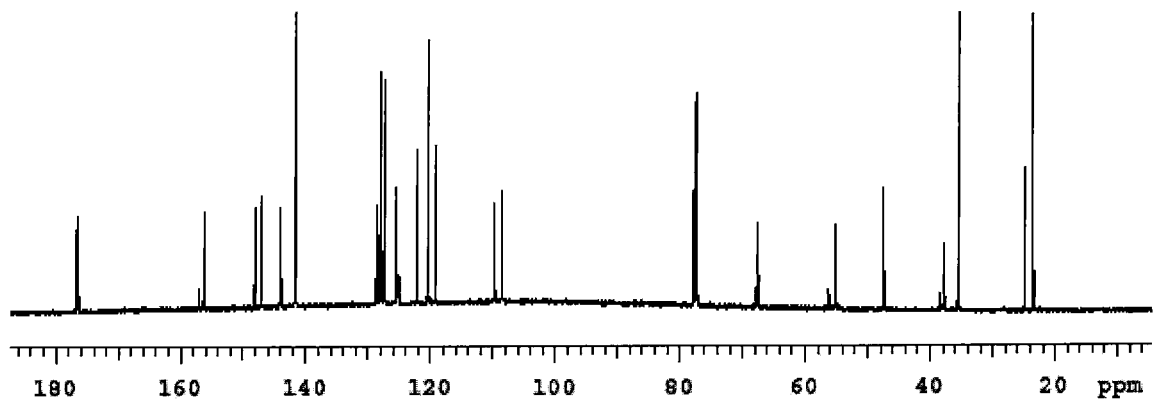

FIG. 41. Fmoc-DOPA(Chex)-OH $^{13}$C NMR (125 MHz, CDCl$_3$).

FIG. 42. Boc-DOPA(acetonide)-OH $^1$H NMR (500 MHz, CDCl$_3$).

Figure 43:
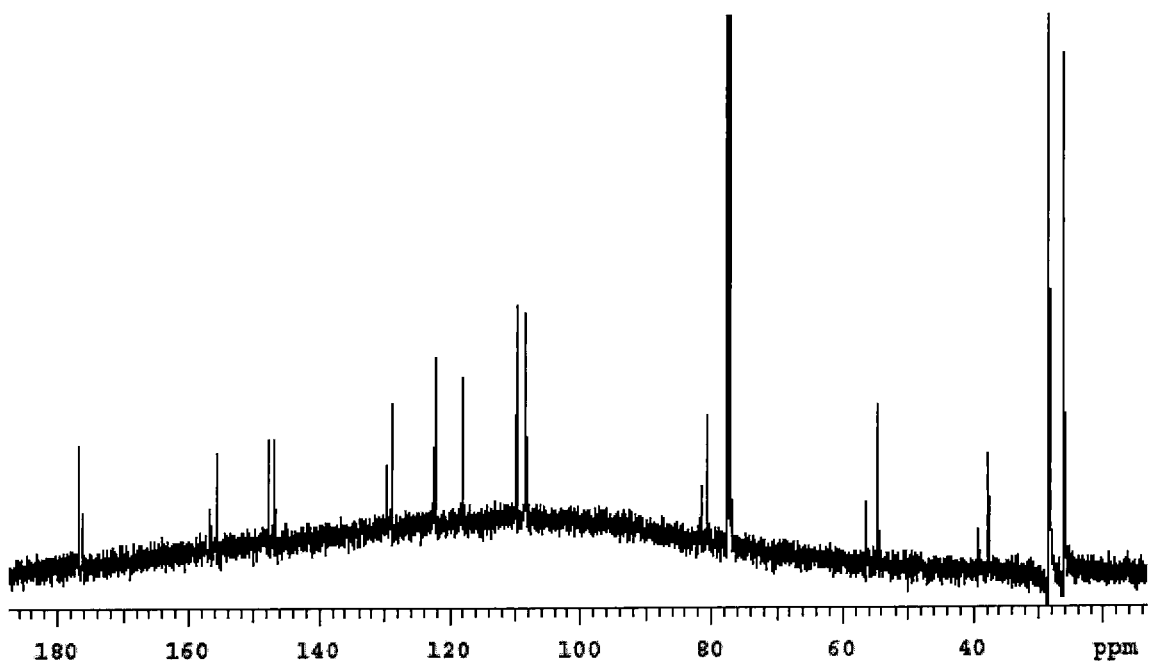

FIG. 43. Boc-DOPA(acetonide)-OH $^{13}$C NMR (125 MHz, CDCl$_3$).

FIG. 44. Boc-DOPA(acetonide)-OH $^1$H NMR (500 MHz, CDCl$_3$).

Figure 45:
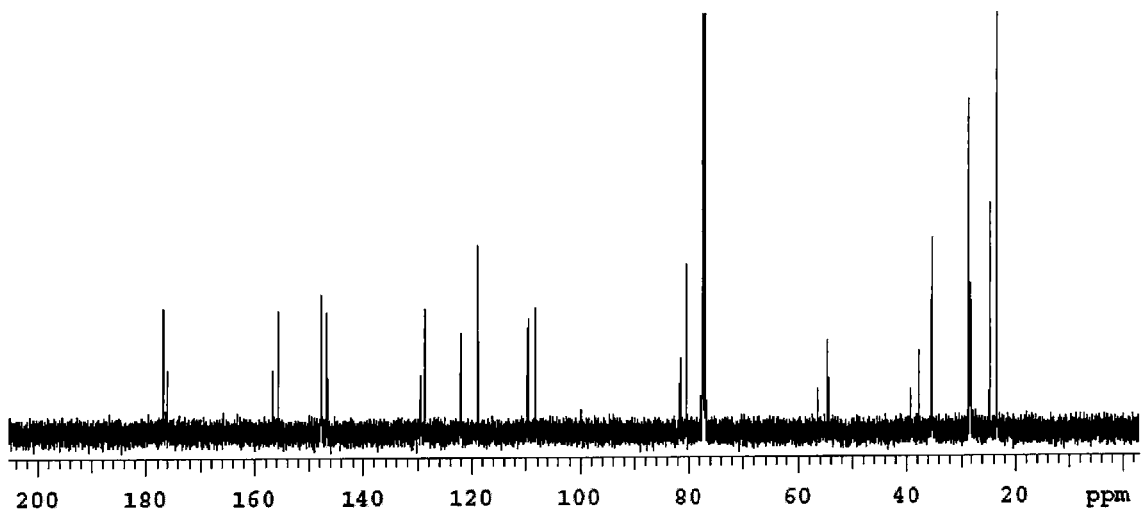

FIG. 45. Boc-DOPA(acetonide)-OH $^{13}$C NMR (125 MHz, CDCl$_3$).

Figure 46:
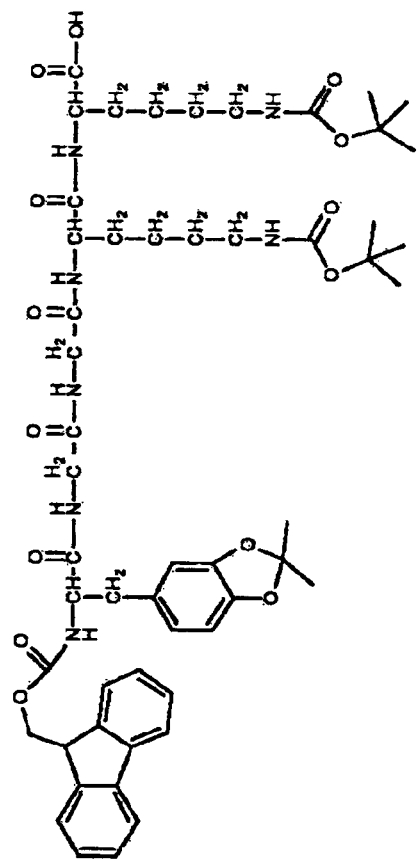
Figure 46:
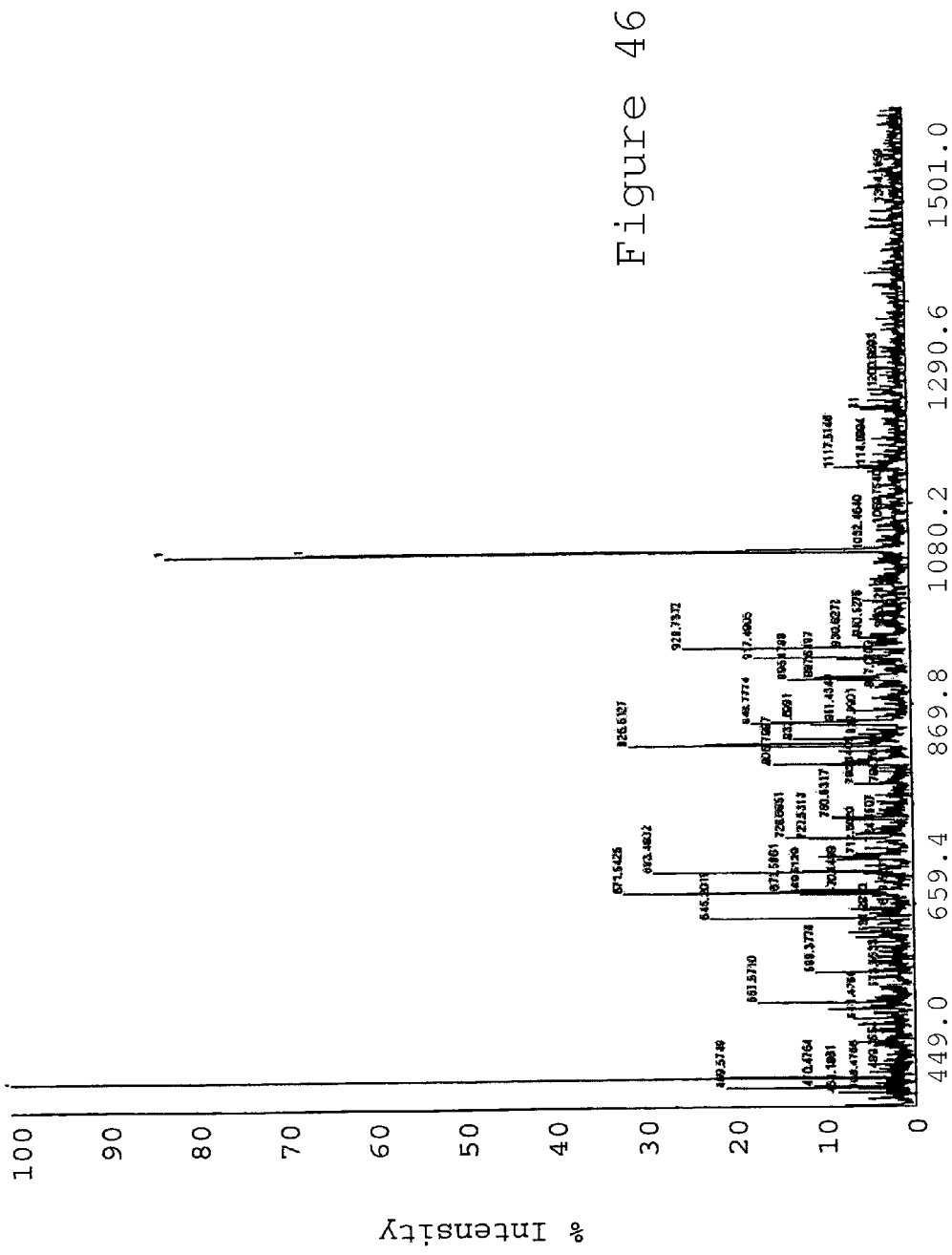

FIG. 46. MALDI-TOF Spectra of Fmoc-DOPA(acetonide)-Gly-Gly-Lys(Boc)-Lys(Boc)-OH.

Figure 47:
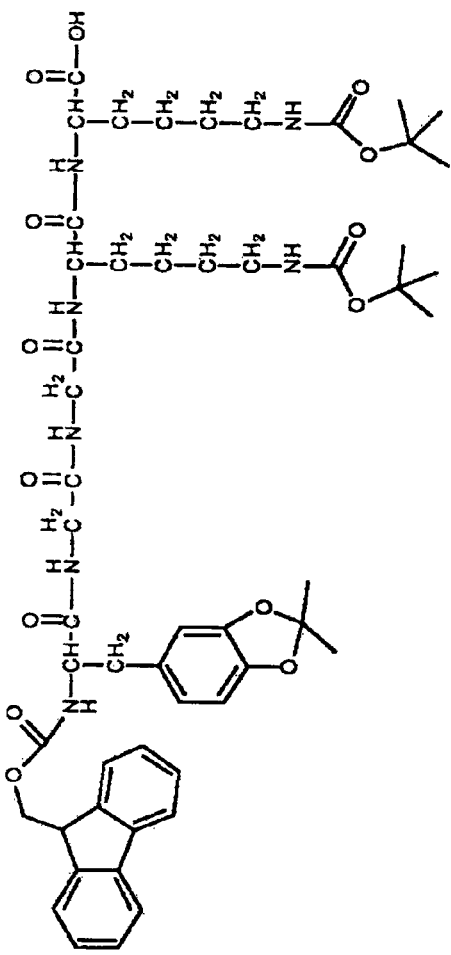
Figure 47:
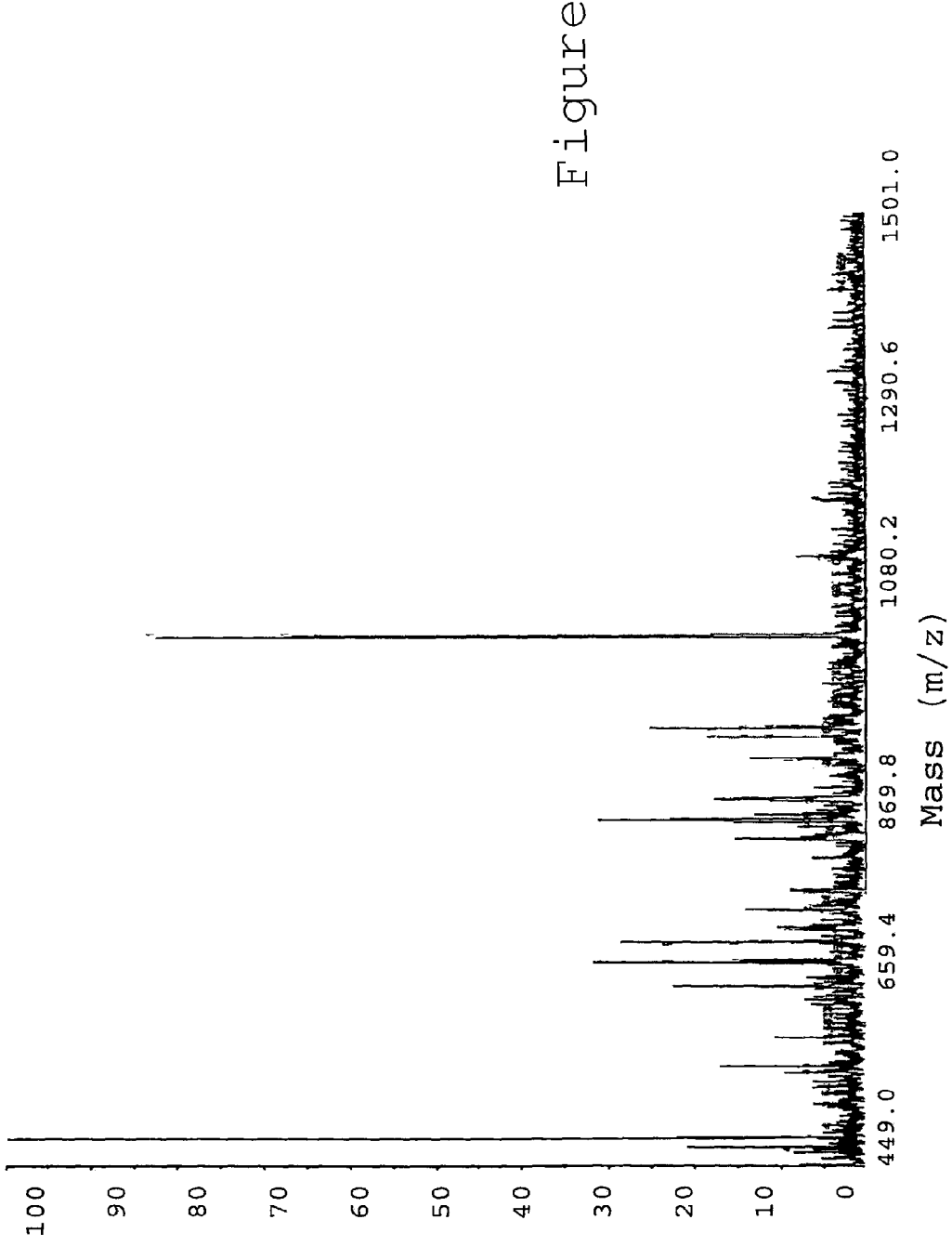

FIG. 47. MALDI-TOF Spectra of Fmoc-DOPA(Chex)-Gly-Gly-Lys(Boc)-Lys(Boc)-OH.

Figure 48:
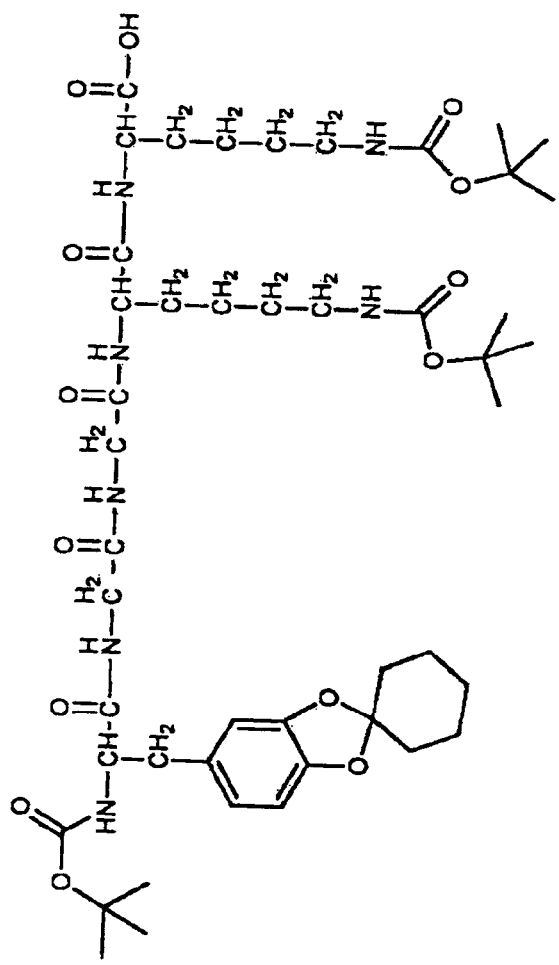
Figure 48:
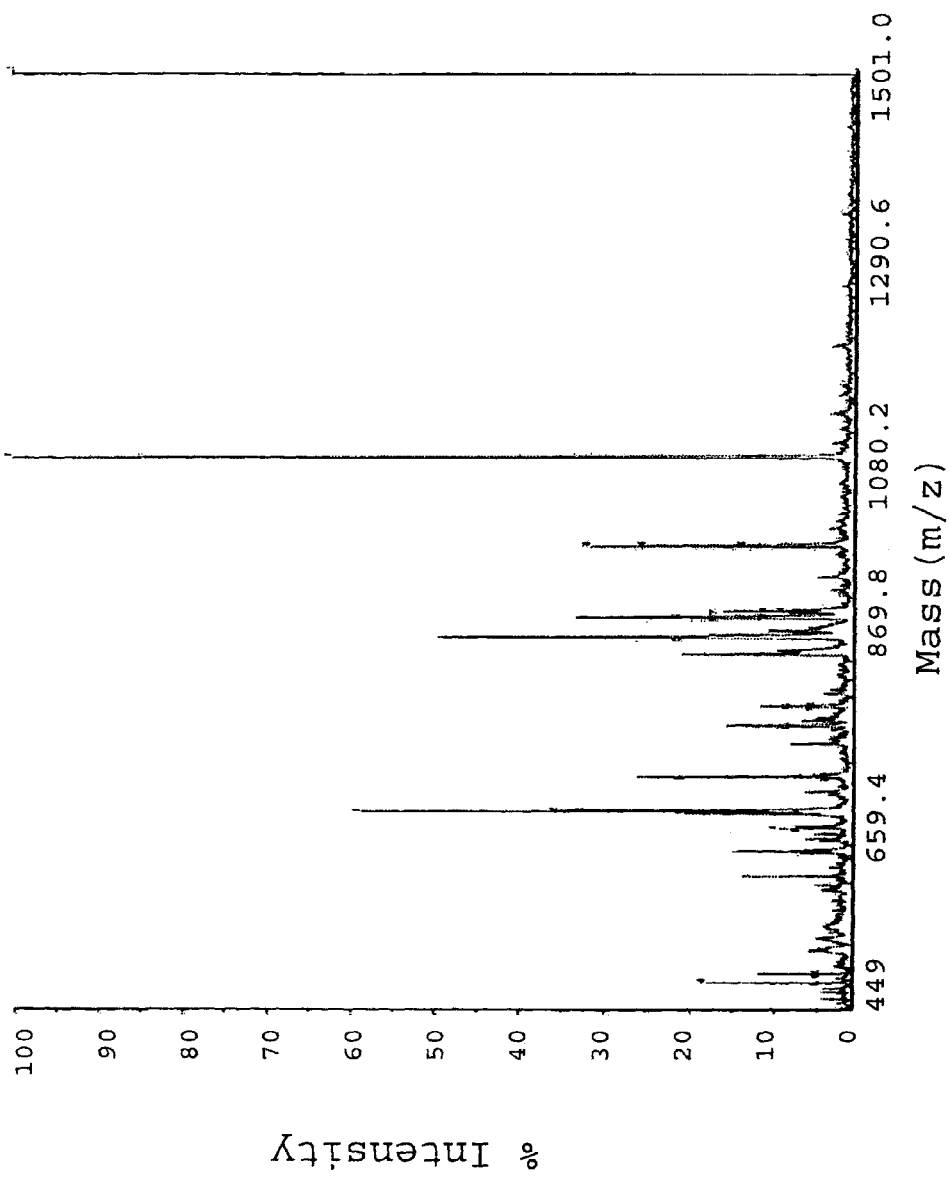

FIG. 48. MALDI-TOF Spectra of Boc-DOPA(Chex)-Gly-Gly-Lys(Boc)-Lys(Boc)-OH.

FIG. 49. Phth-dopamine $^1$H NMR (500 MHz, DMSO-d$_6$).

Figure 50:
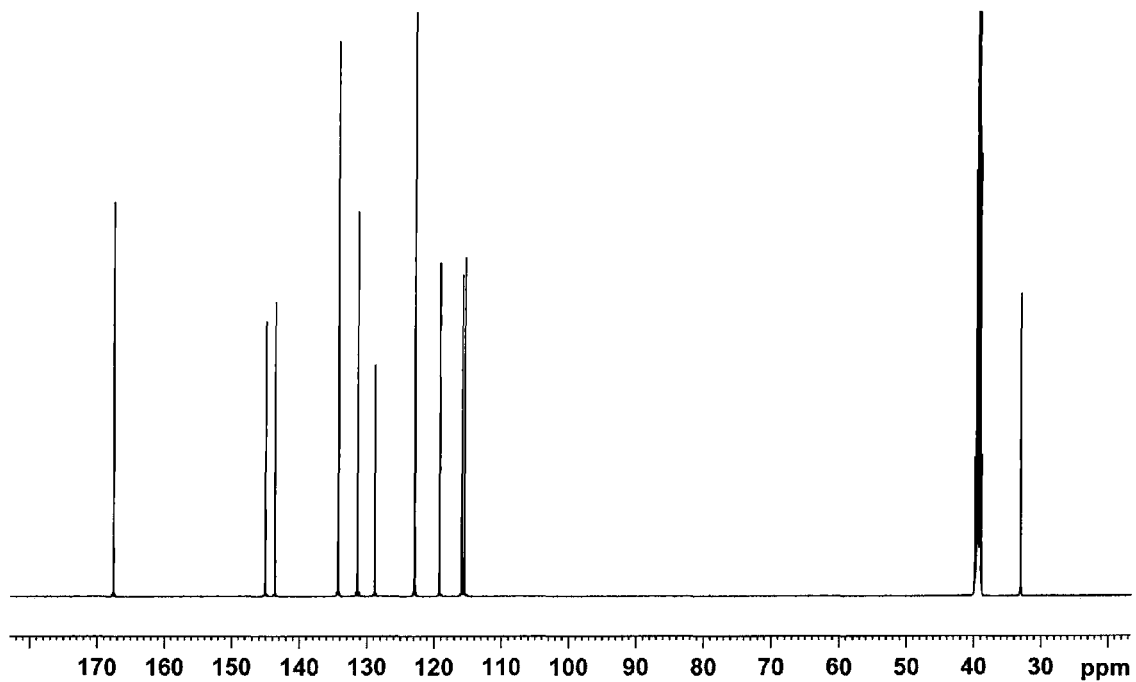

FIG. 50. Phth-dopamine $^{13}$C NMR (125 MHz, DMSO-d$_6$).

Figure 51:
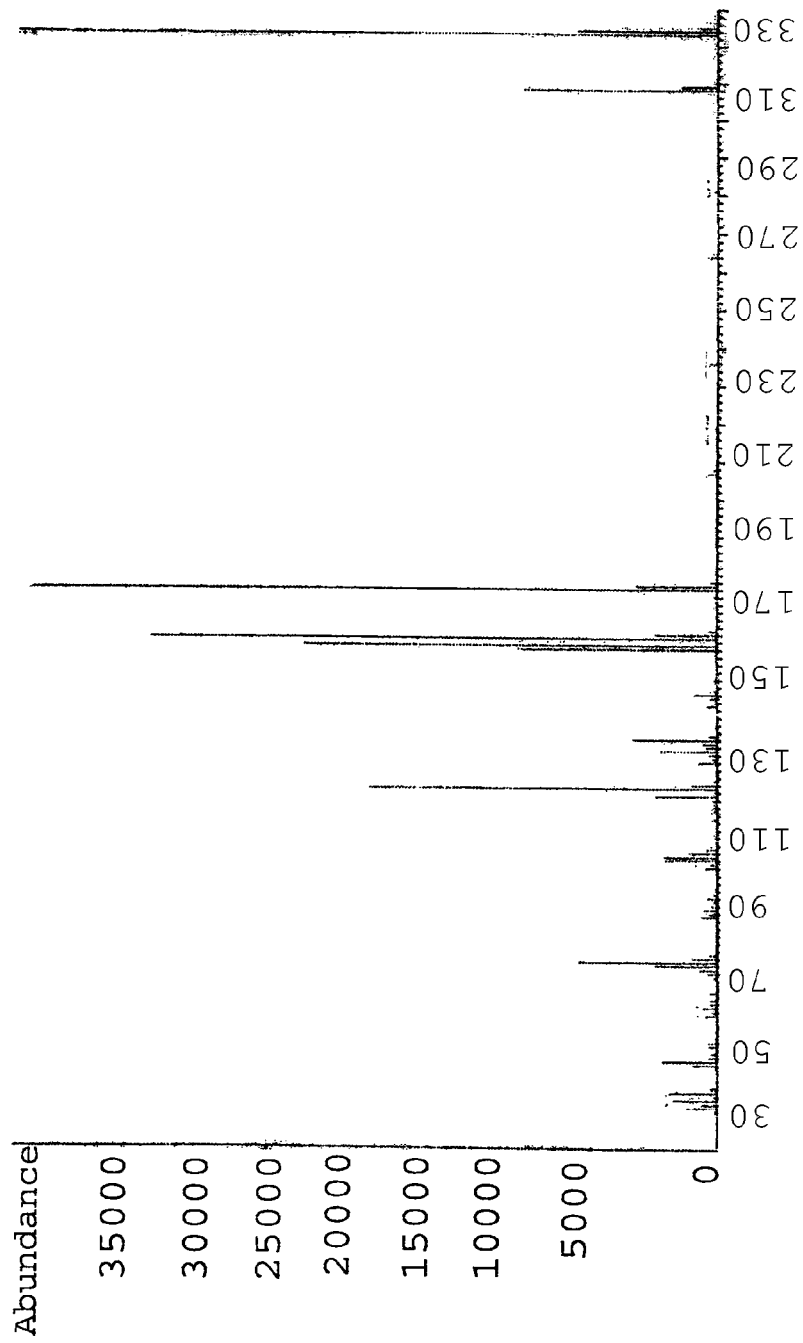

FIG. 51. GC-MS Spectrum of Phth-dopamine(acetonide).

FIG. 52. Phth-dopamine(acetonide). $^1$H NMR (500 MHz, CDCl$_3$).

Figure 53:
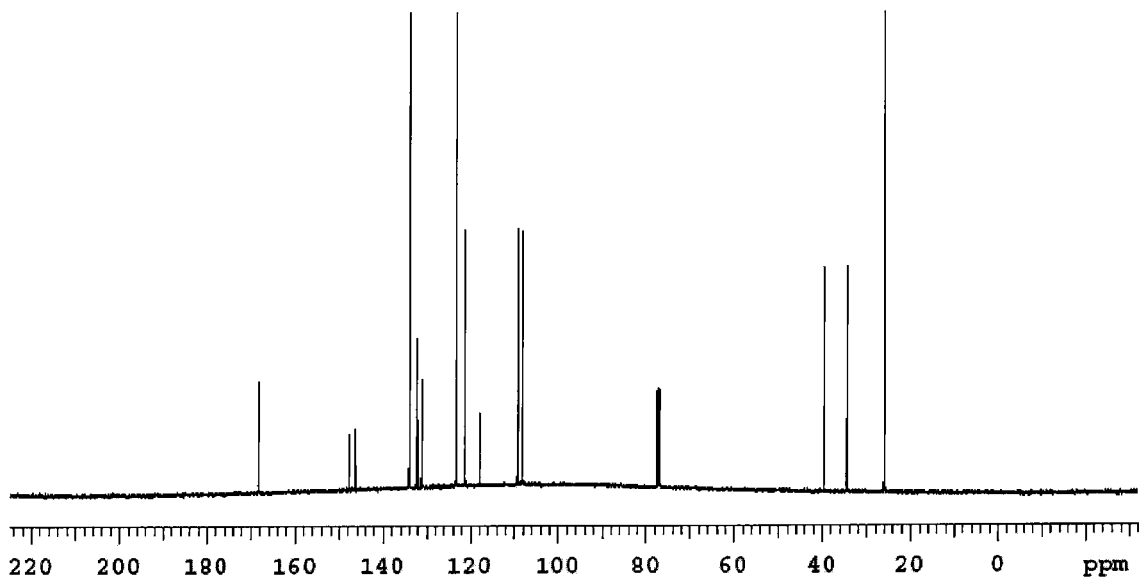

FIG. 53. Phth-dopamine(acetonide). $^{13}$C NMR (125 MHz, CDCl$_3$).

Figure 54:
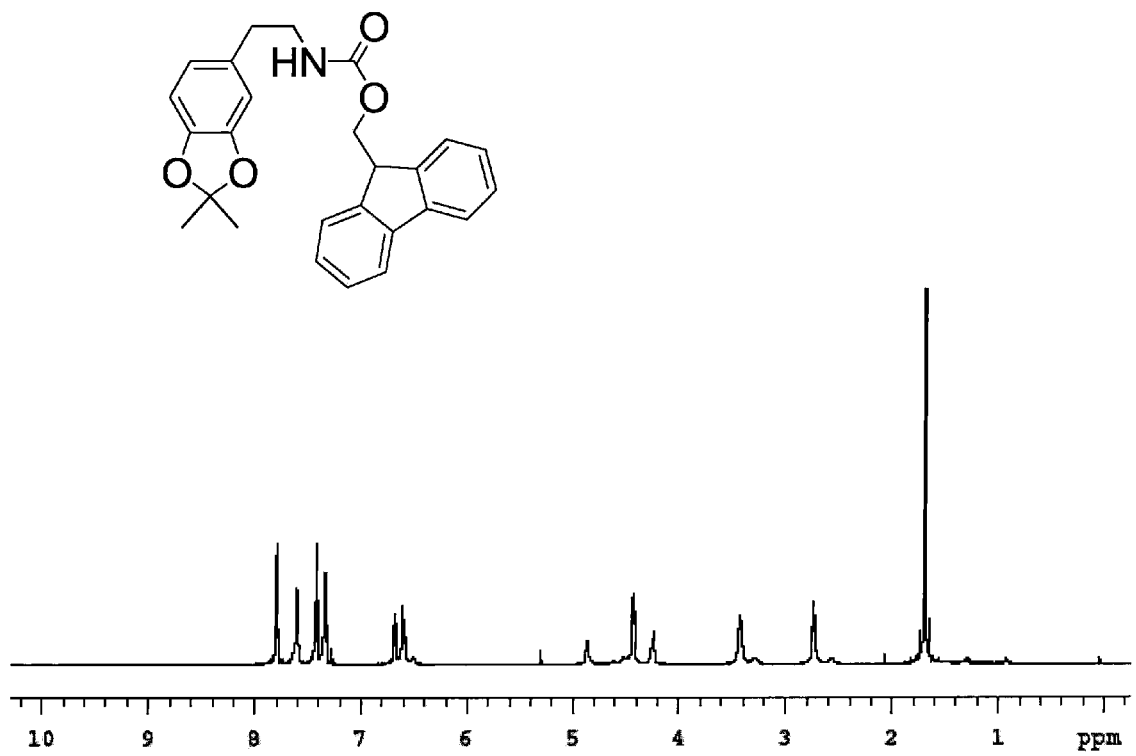

FIG. 54. Fmoc-dopamine(acetonide) $^1$H NMR (500 MHz, CDCl$_3$).

Figure 55:
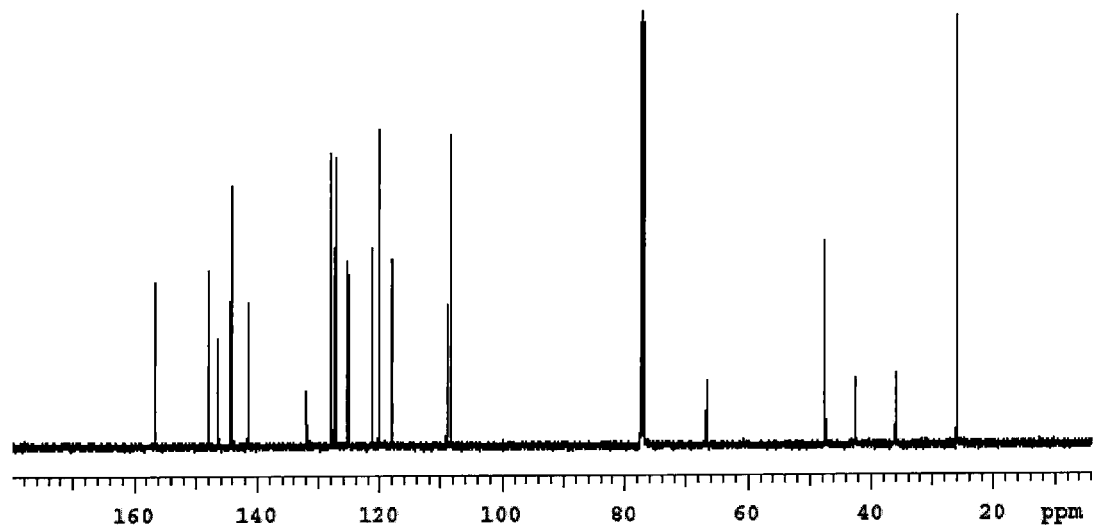

FIG. 55. Fmoc-dopamine(acetonide) $^{13}$C NMR (125 MHz, CDCl$_3$).

FIG. 56. LC-MS Data of TsOH-DDTQ (Positive Mode).

FIG. 57. LC-MS Data of TsOH-DDTQ (Negative Mode).

FIG. 58. TsOH-DDTQ $^1$H NMR (500 MHz, DMSO-d$_6$).

Figure 59:
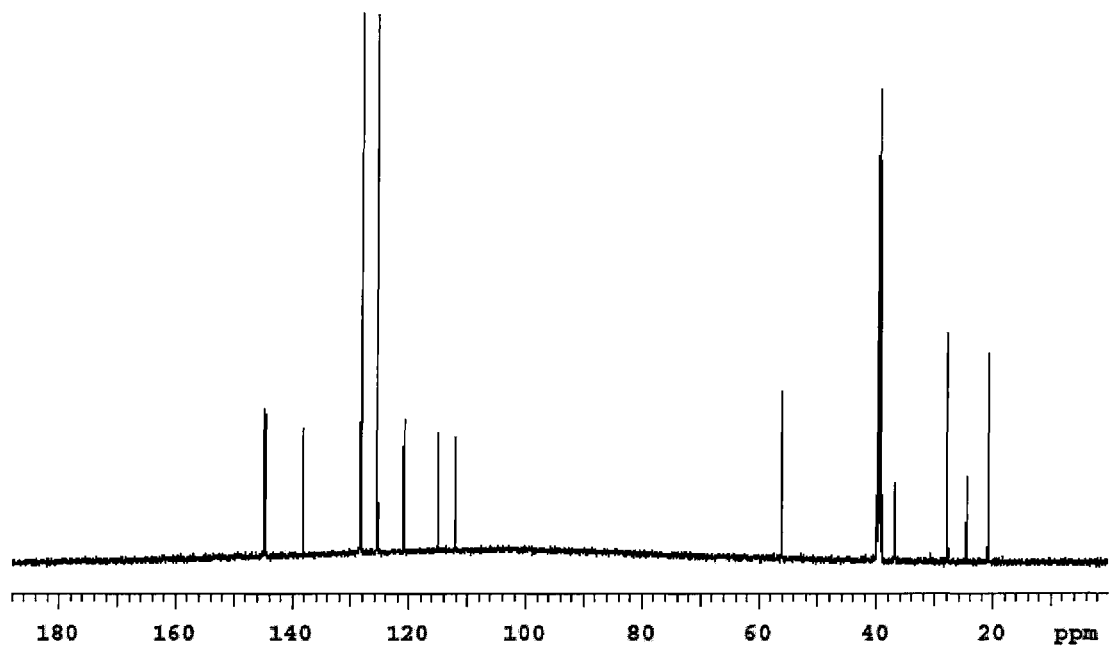

FIG. 59. TsOH-DDTQ $^{13}$C NMR (125 MHz, DMSO-d$_6$).

FIG. 60. TsOH-DDTQ $^{13}$C NMR (125 MHz, DMSO-d$_6$).

Figure 61:
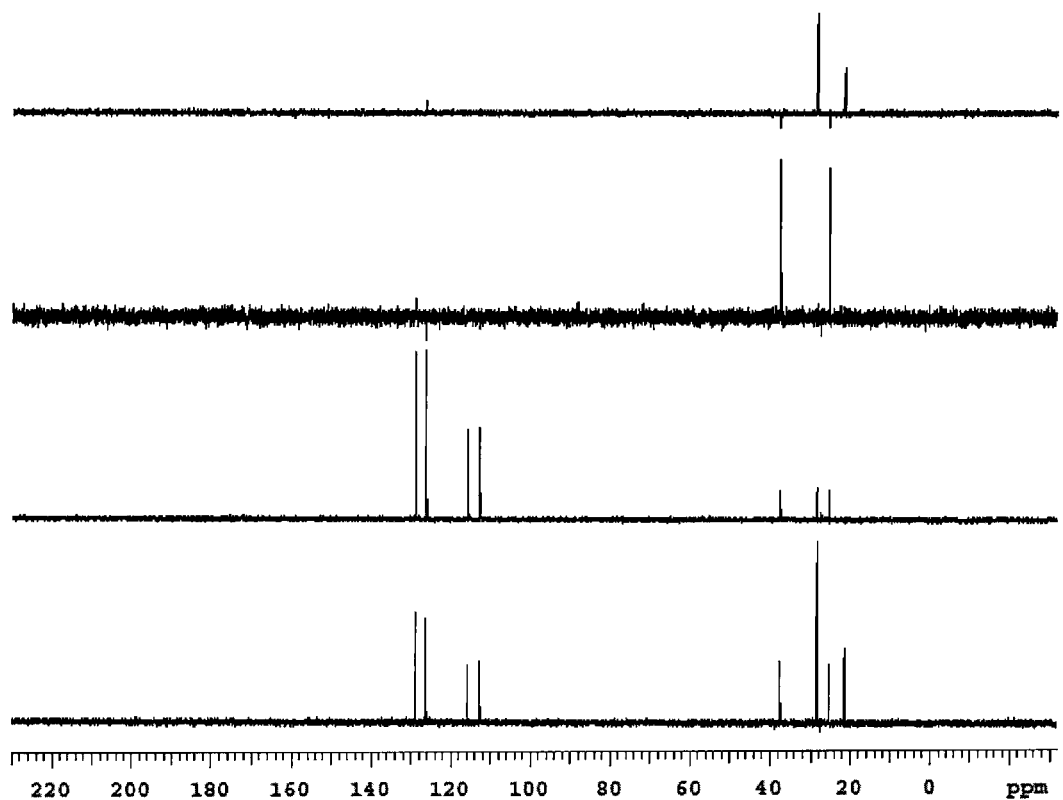

FIG. 61. TsOH-DDTQ $^{13}$C NMR-DEPT (125 MHz, DMSO-d$_6$).

FIG. 62. TsOH-DDTQ $^1$H NMR-COSY (500 MHz, DMSO-d$_6$).

FIG. 63. Hydrochloride Salt of (S)-methyl6,7-dihydroxy-1,1-dimethyl-1,2,3,4-tetrahydroisoquinoline-3-carboxylate. $^1$H NMR (500 MHz, CD$_3$OD).

Figure 64:
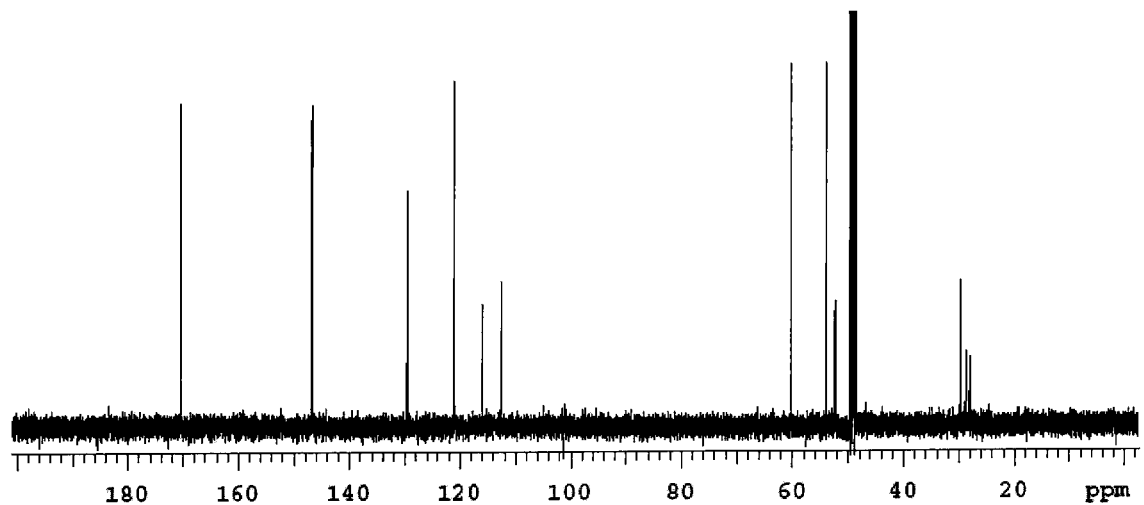

FIG. 64. Hydrochloride Salt of (S)-methyl6,7-dihydroxy-1,1-dimethyl-1,2,3,4-tetrahydroisoquinoline-3-carboxylate. $^{13}$C NMR (125 MHz, CD$_3$OD).

Figure 65:
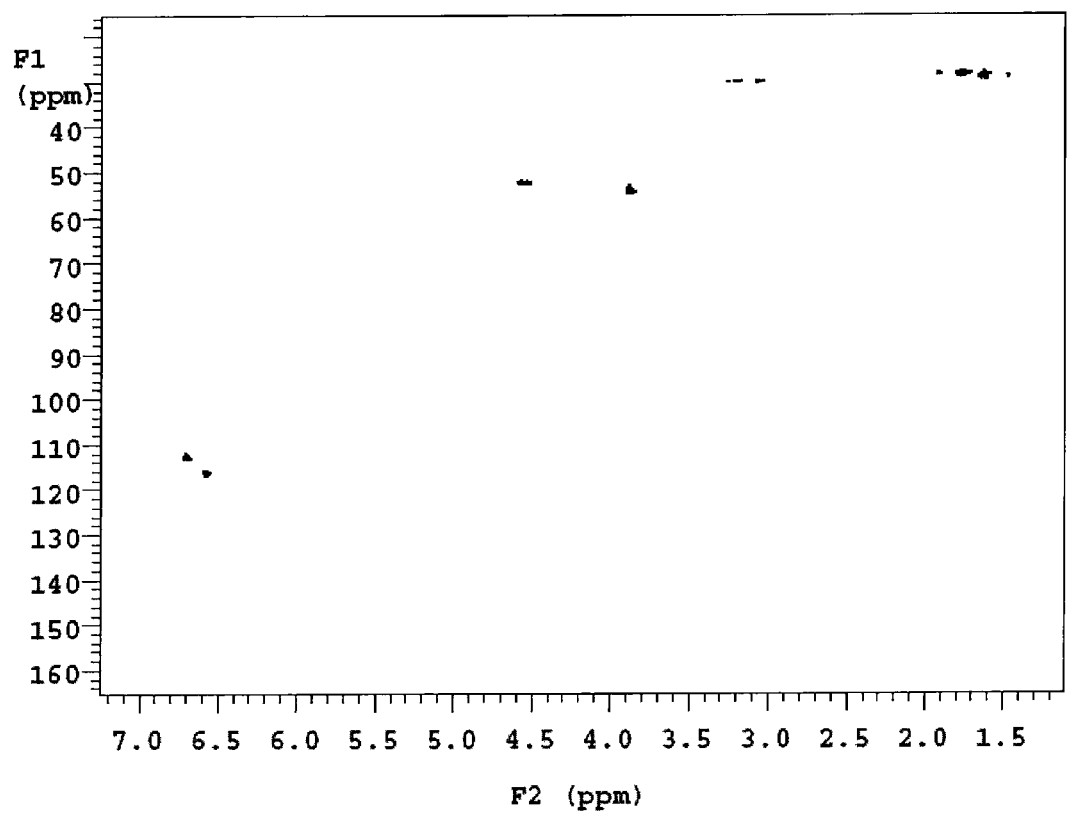

FIG. 65. Hydrochloride Salt of (S)-methyl6,7-dihydroxy-1,1-dimethyl-1,2,3,4-tetrahydroisoquinoline-3-carboxylate. HMQC (500 MHz, CD$_3$OD).

Figure 66:
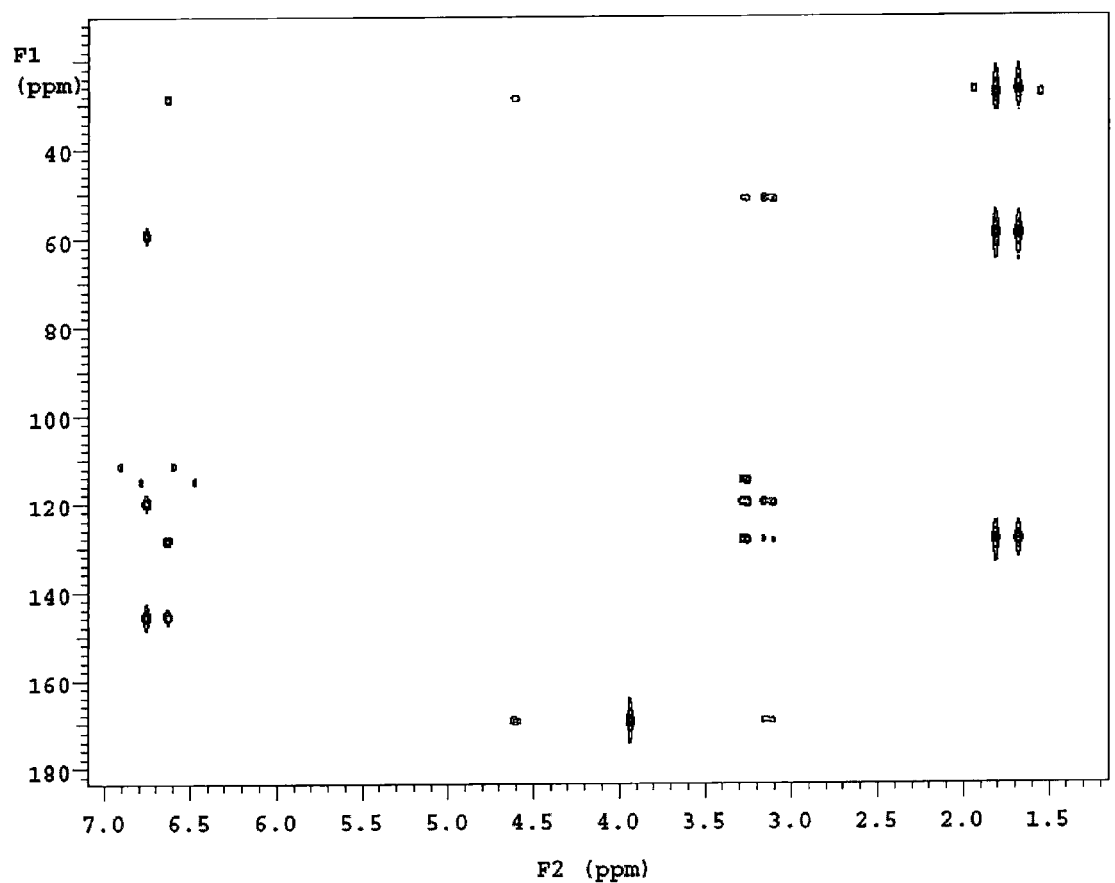

FIG. 66. Hydrochloride Salt of (S)-methyl6,7-dihydroxy-1,1-dimethyl-1,2,3,4-tetrahydroisoquinoline-3-carboxylate. HMBC (500 MHz, CD$_3$OD).

FIG. 67. TFA-dopamine $^1$H NMR (500 MHz, DMSO-d$_6$).

Figure 68:
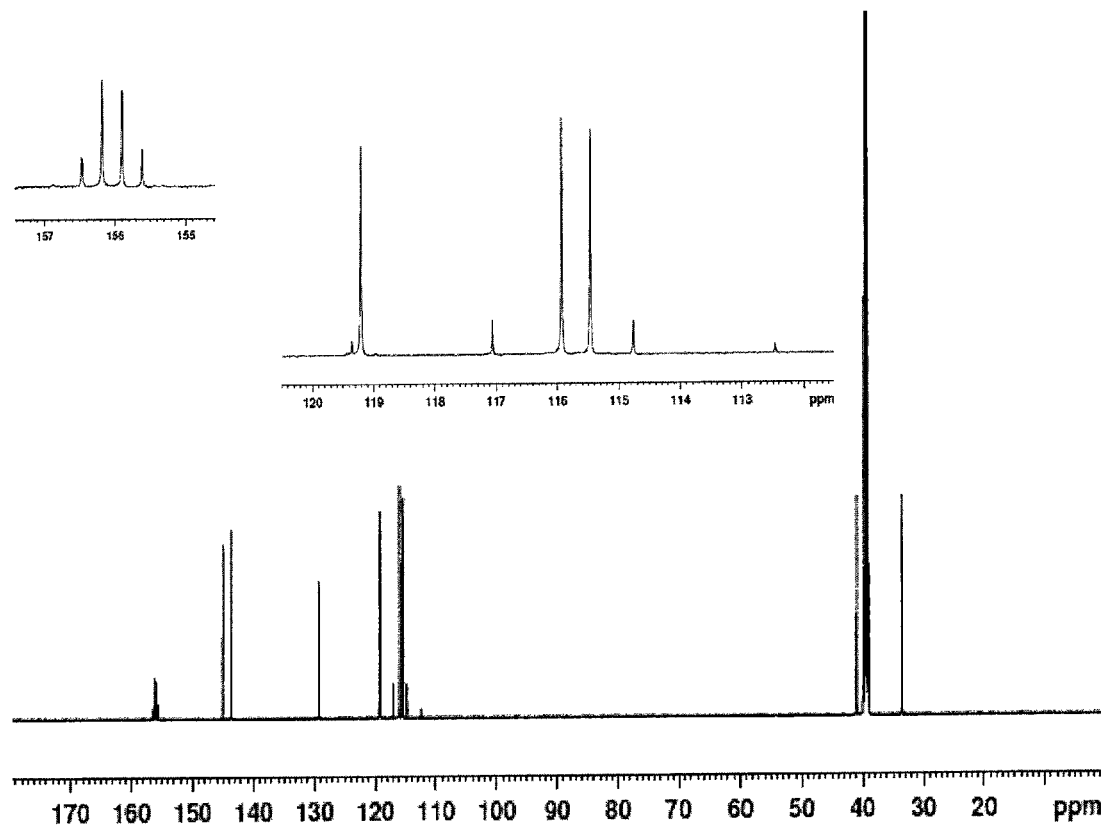

FIG. 68. TFA-dopamine $^{13}$C NMR (125 MHz, DMSO-d$_6$).

FIG. 69. TFA-dopamine(acetonide) $^1$H NMR (500 MHz, CDCl$_3$).

Figure 70:
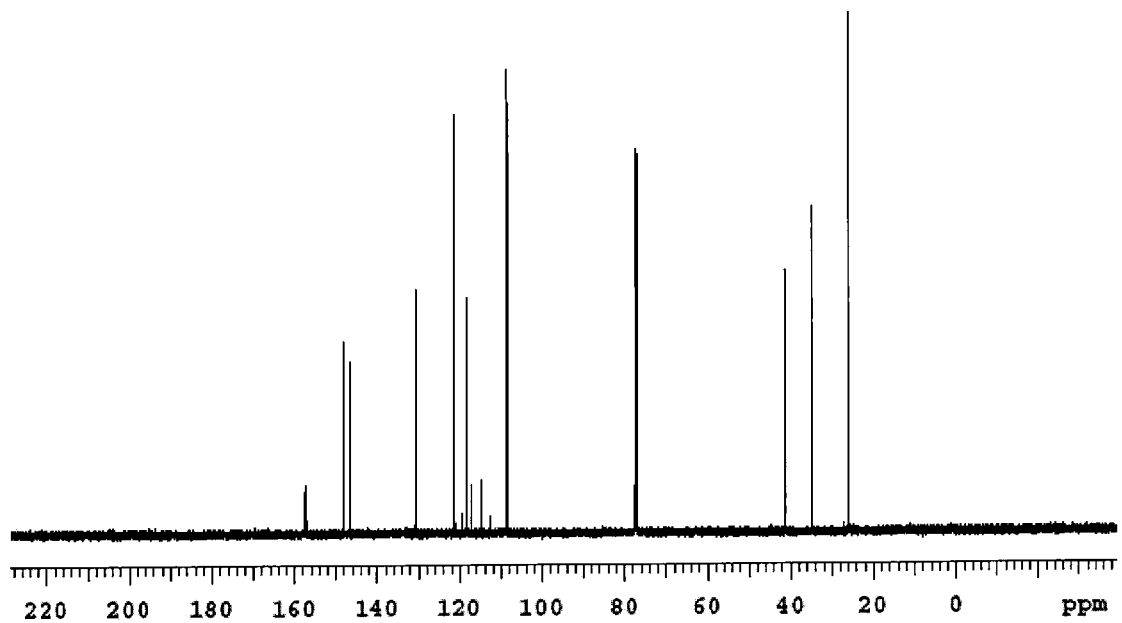

FIG. 70. TFA-dopamine(acetonide) $^{13}$C NMR (125 MHz, CDCl$_3$).

Figure 71:
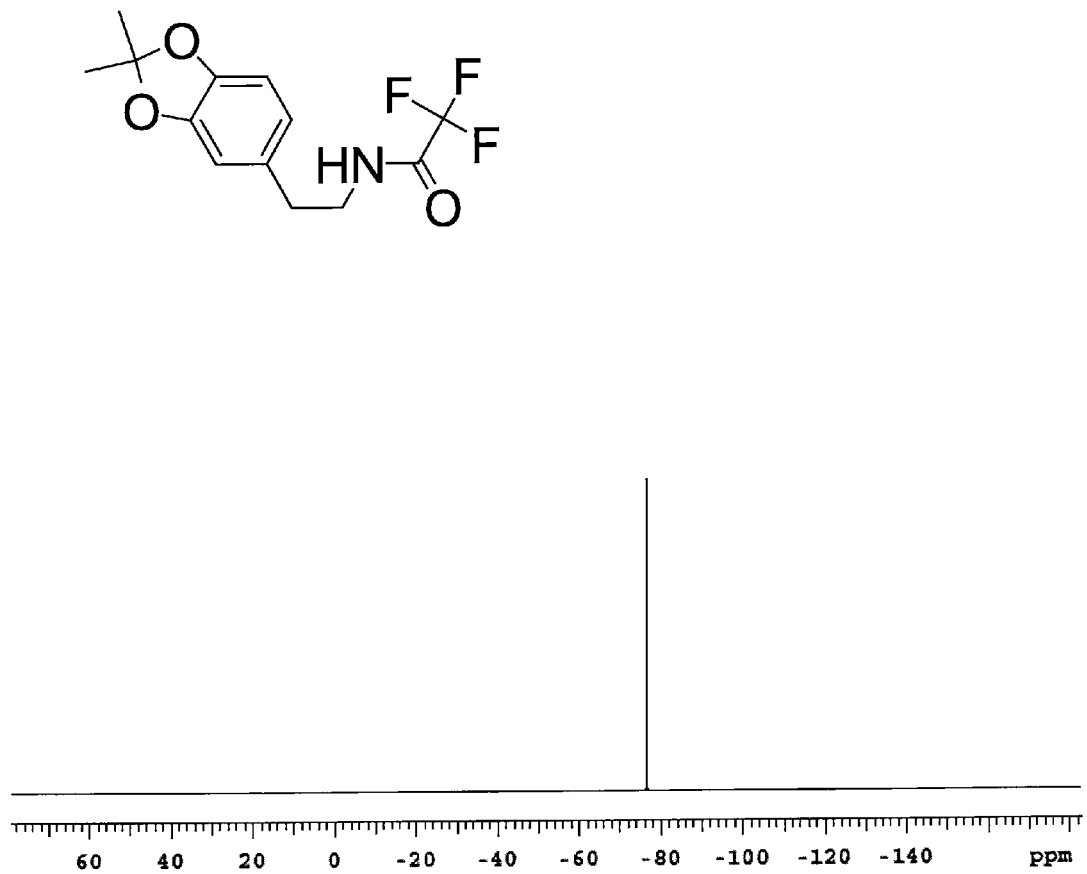

FIG. 71. TFA-dopamine(acetonide) $^{19}$F NMR (376 MHz, CDCl$_3$).

FIG. 72. GC-MS Spectrum of Dopamine(acetonide).

FIG. 73. Dopamine(acetonide). $^1$H NMR (500 MHz, CDCl$_3$).

Figure 74:
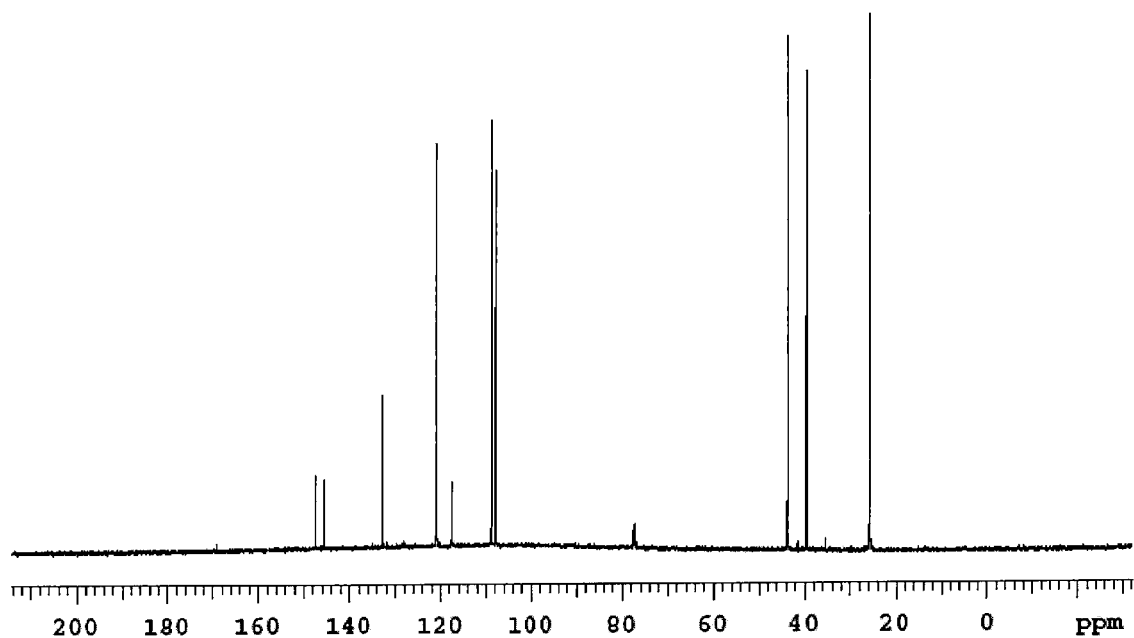

FIG. 74. Dopamine(acetonide). $^{13}$C NMR (125 MHz, CDCl$_3$).

Figure 75:
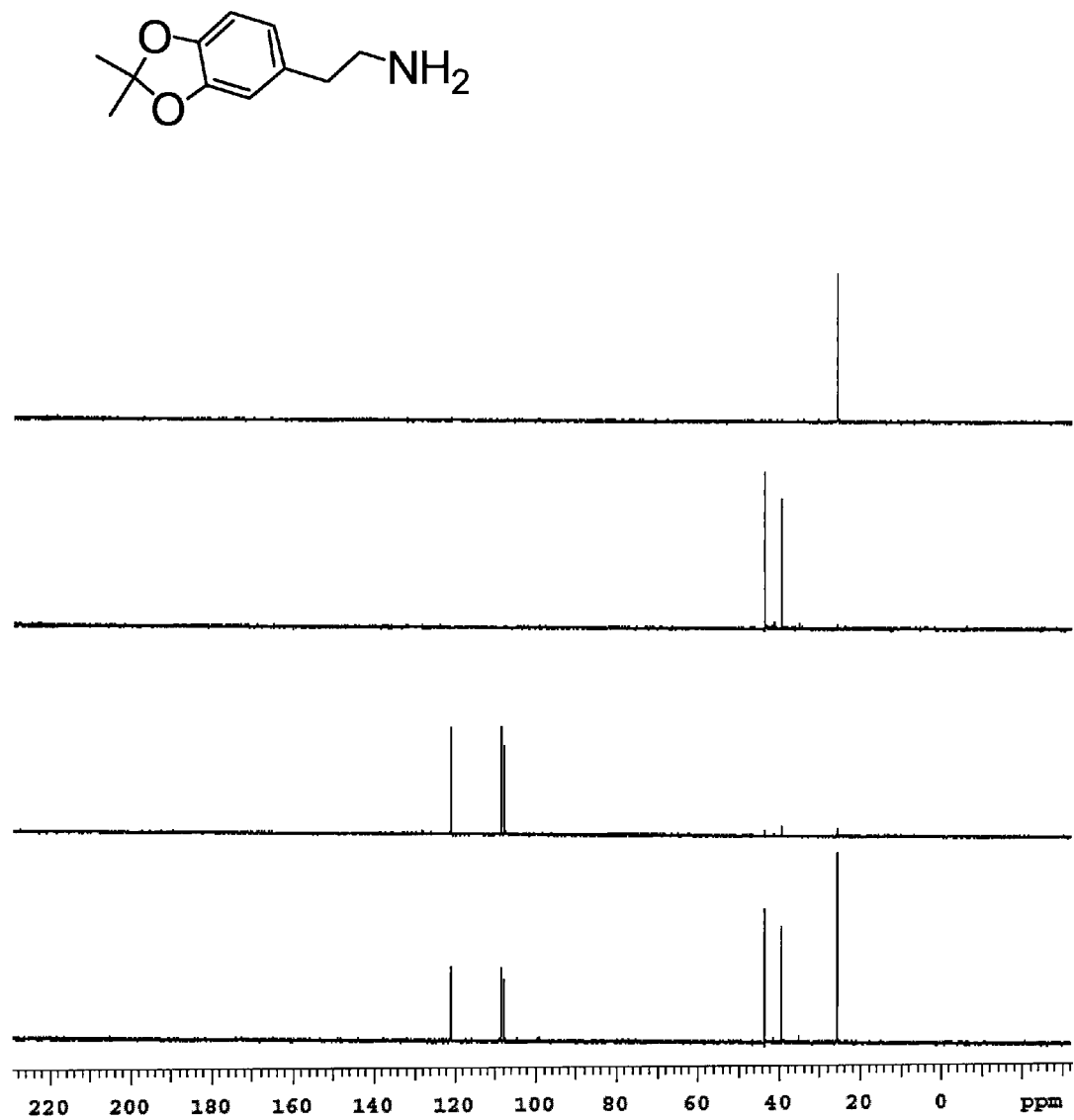

FIG. 75. Dopamine(acetonide). $^{13}$C NMR-DEPT (125 MHz, CDCl$_3$).

FIG. 76. MS Spectra of DHA-dopamine(acetonide).

Figure 77:
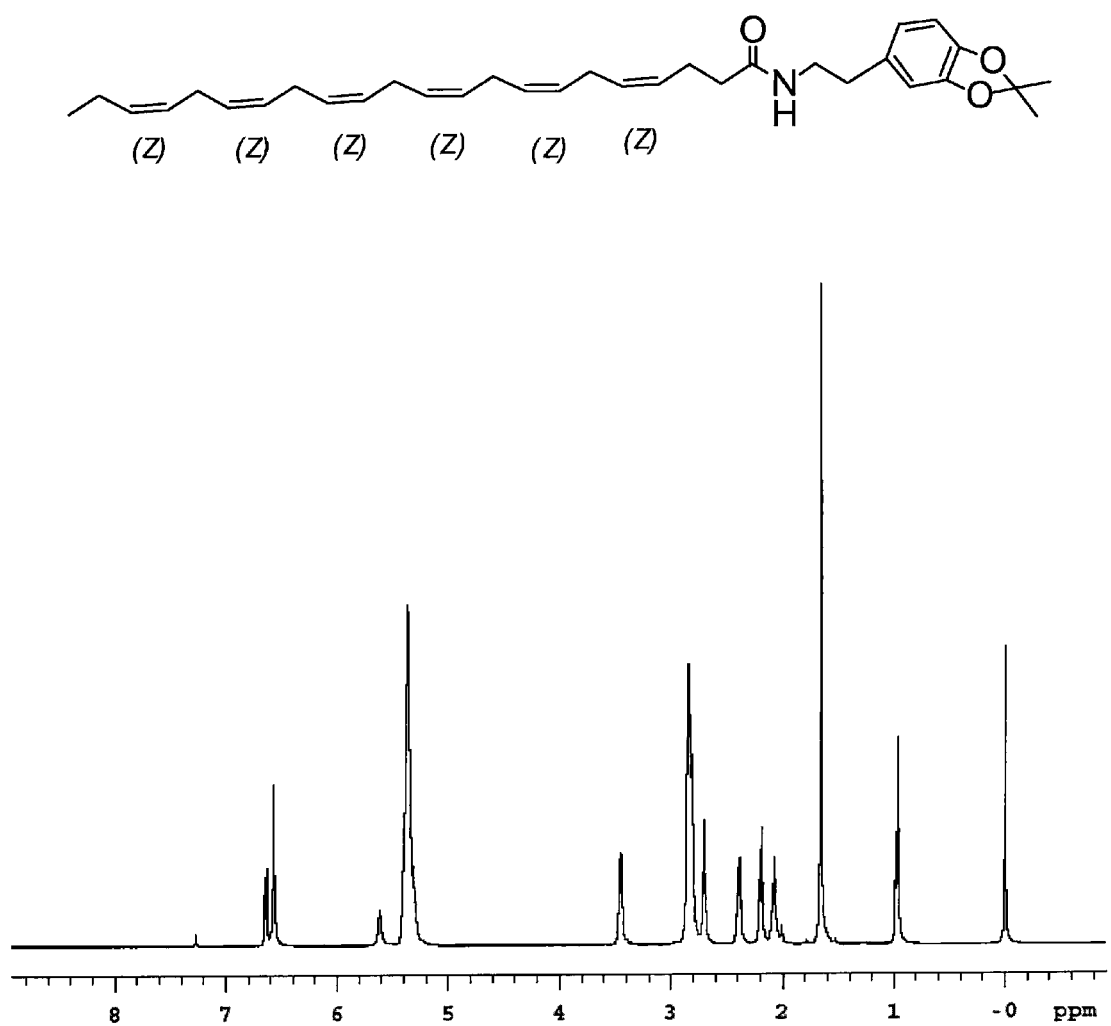

FIG. 77. DHA-dopamine(acetonide). $^1$H NMR (500 MHz, CDCl$_3$).

Figure 78:
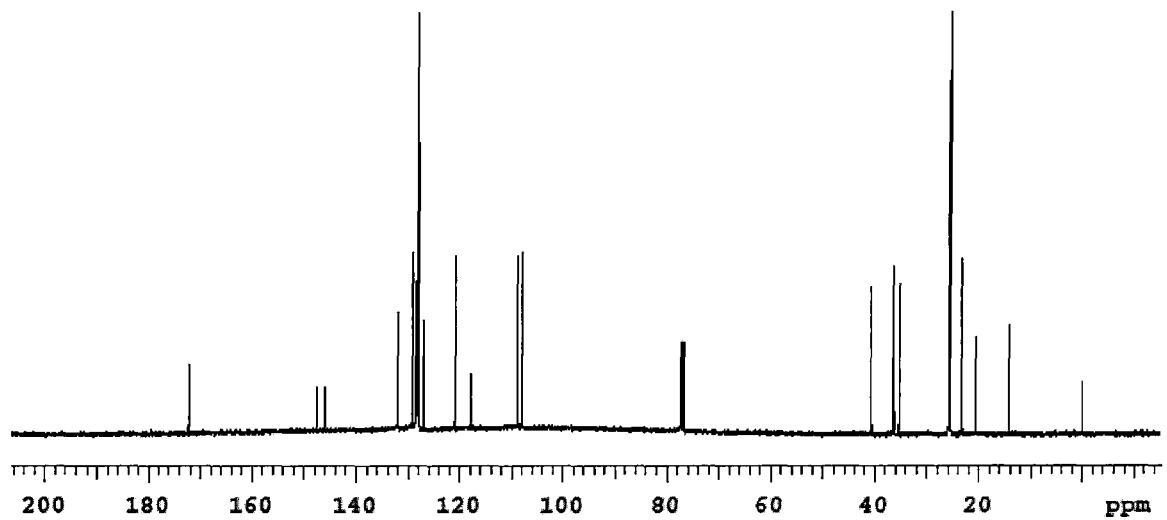

FIG. 78. DHA-dopamine(acetonide). $^{13}$C NMR (125 MHz, CDCl$_3$).

Figure 79:
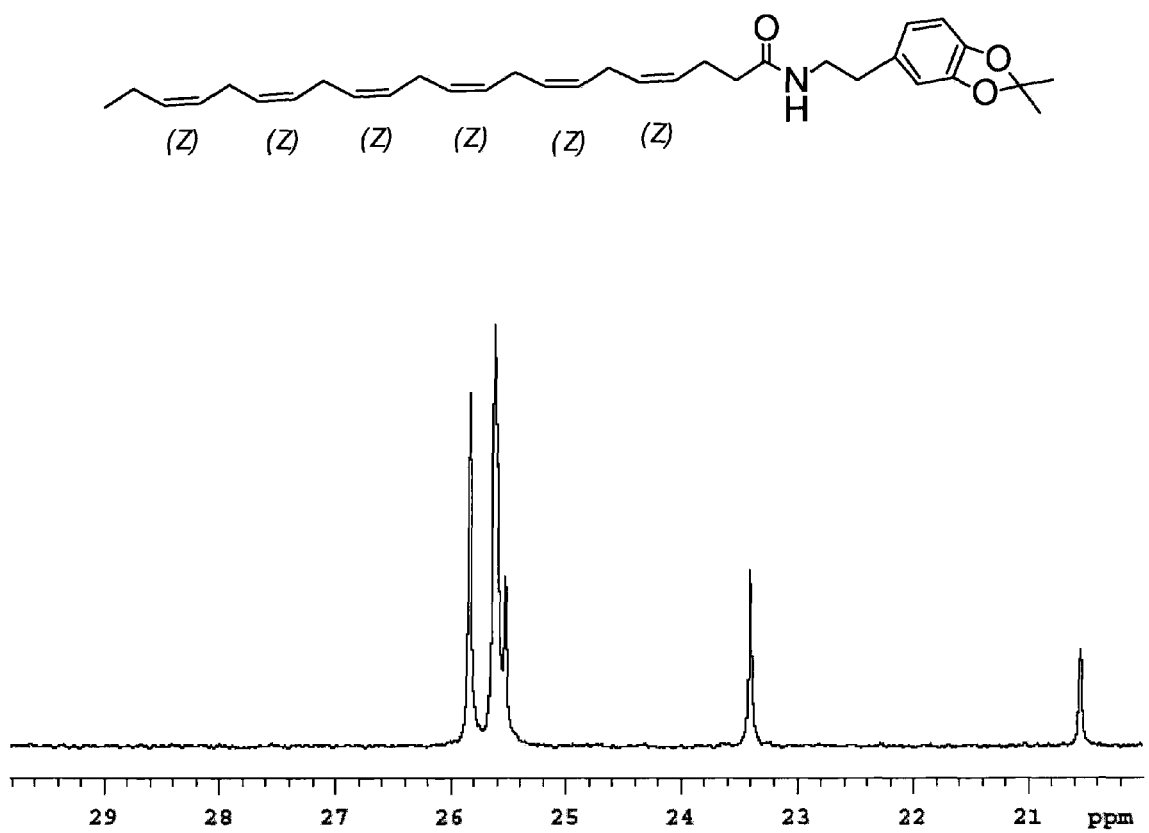

FIG. 79. DHA-dopamine(acetonide). $^{13}$C NMR (125 MHz, CDCl$_3$).

Figure 80:
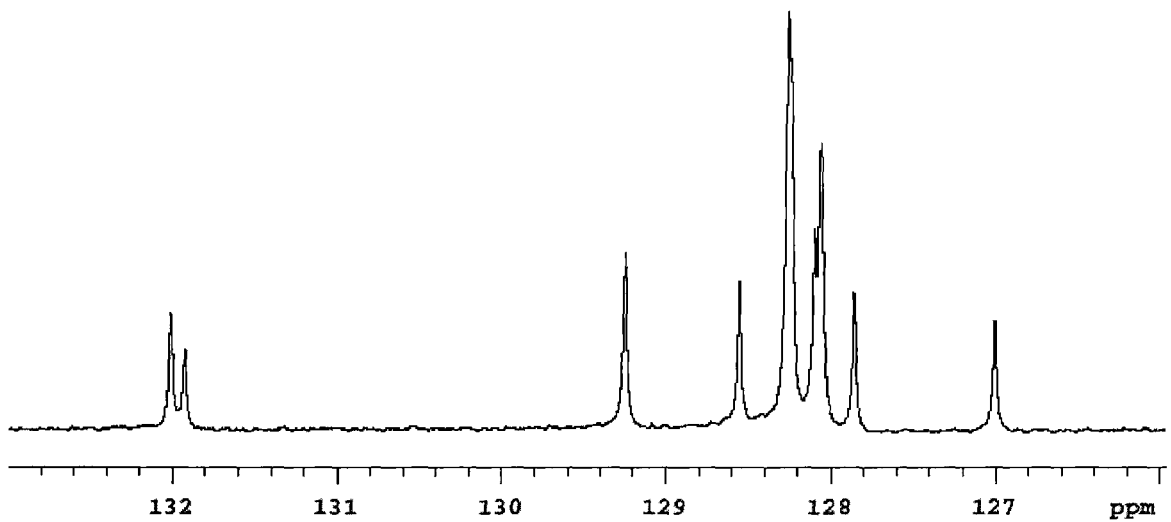

FIG. 80. DHA-dopamine(acetonide). $^{13}$C NMR (125 MHz, CDCl$_3$), from 125 ppm to 135 ppm.

FIG. 81. MS Spectra of DHA-dopamine.

Figure 82:
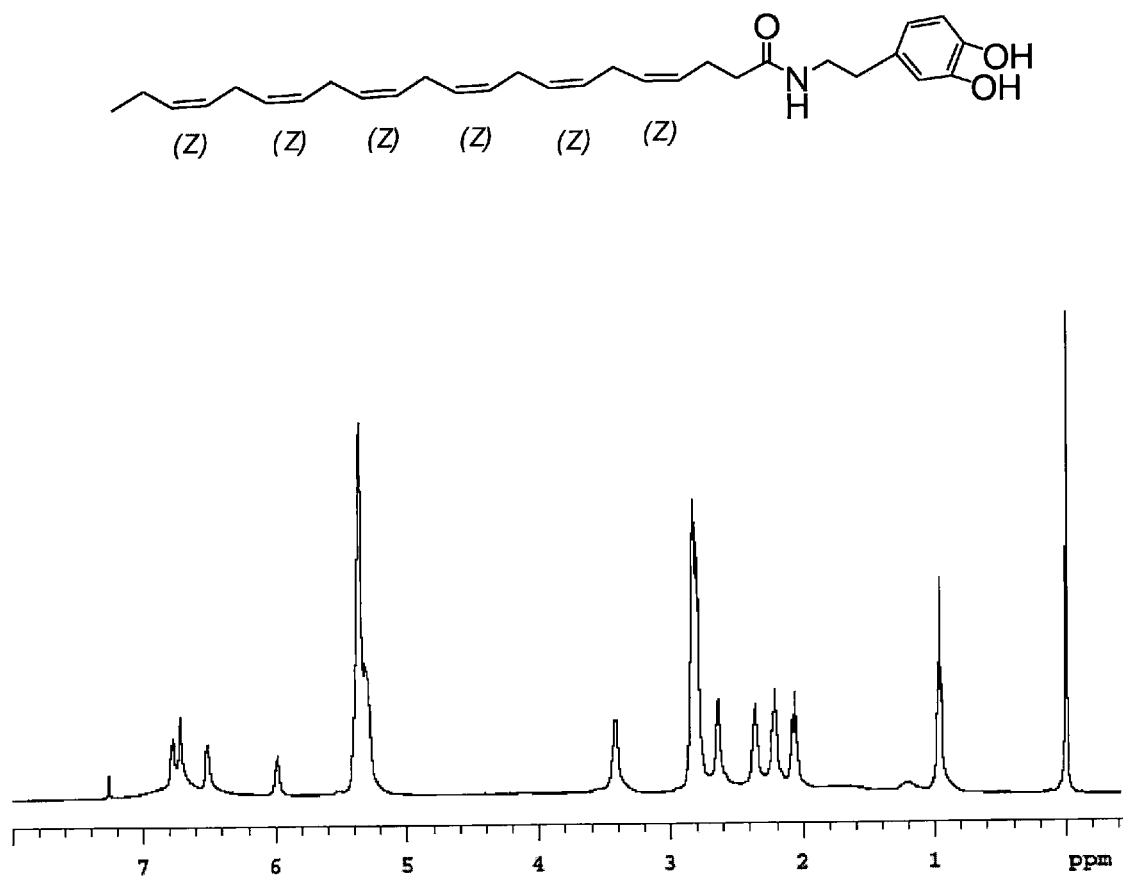

FIG. 82. DHA-dopamine $^1$H NMR (500 MHz, CDCl$_3$).

Figure 83:
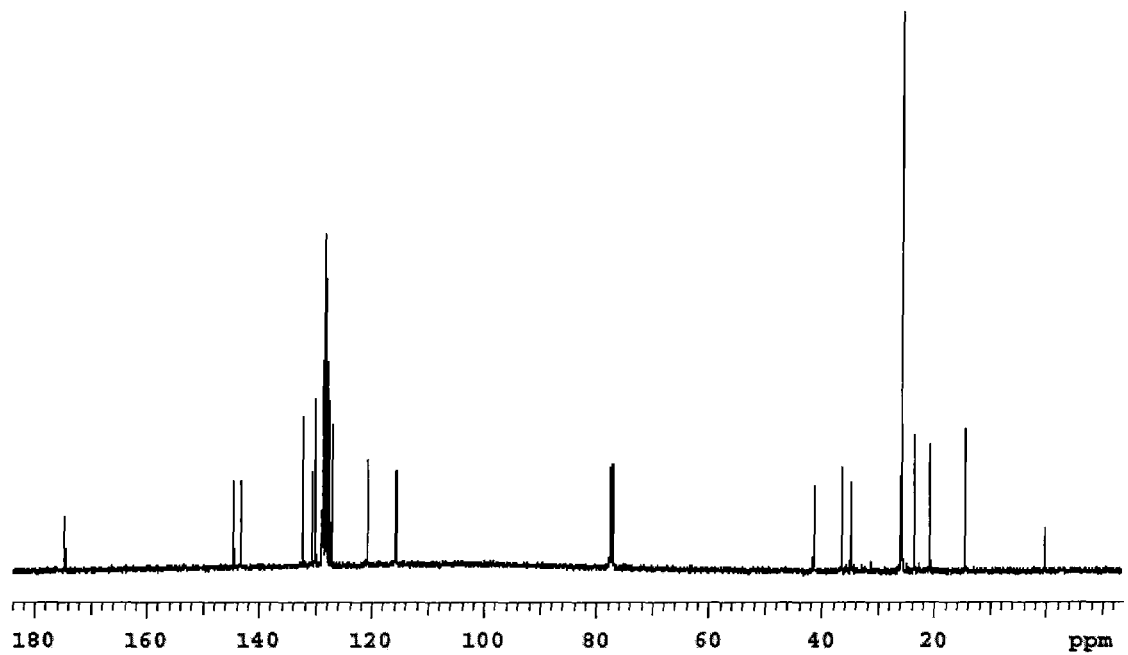

FIG. 83. DHA-dopamine $^{13}$C NMR (125 MHz, CDCl$_3$).

Figure 84:
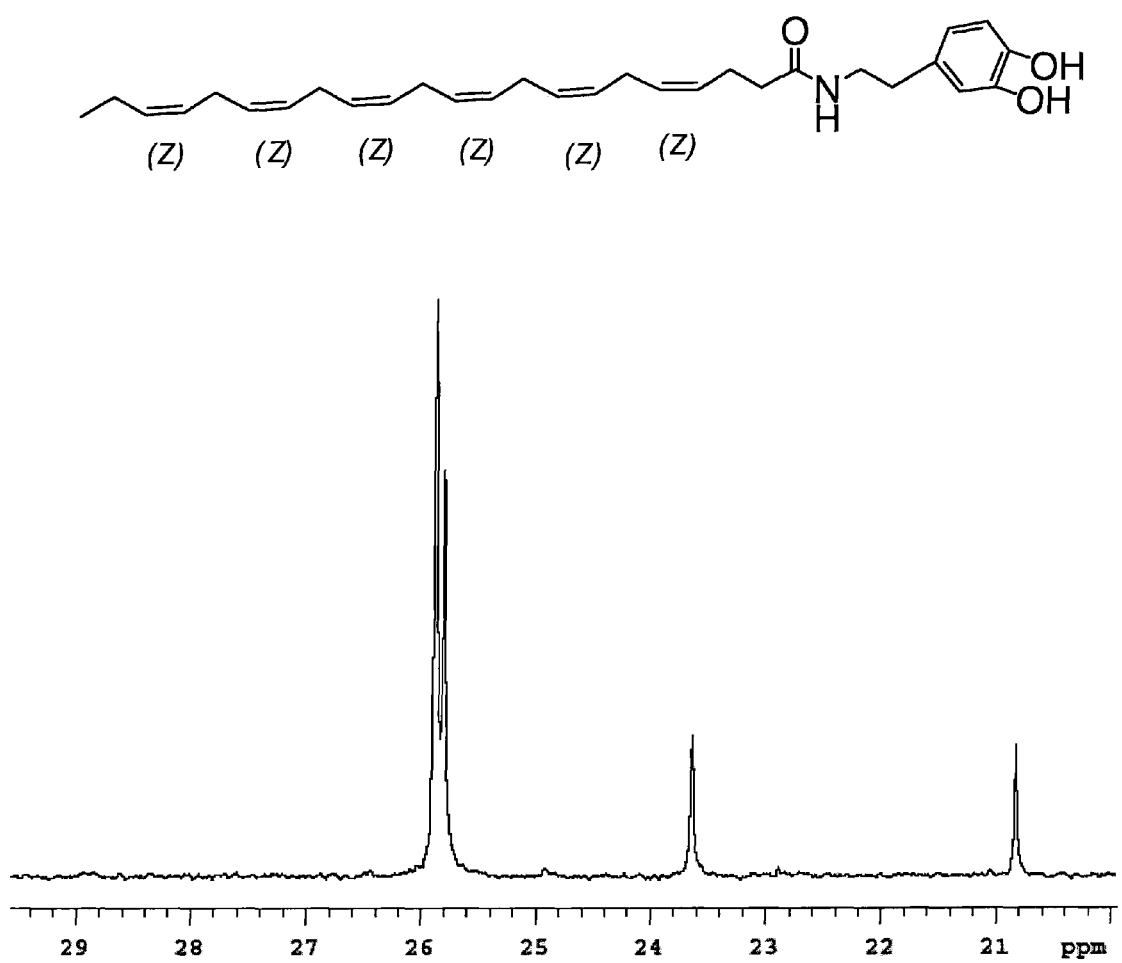

FIG. 84. DHA-dopamine $^{13}$C NMR (125 MHz, CDCl$_3$).

Figure 85:
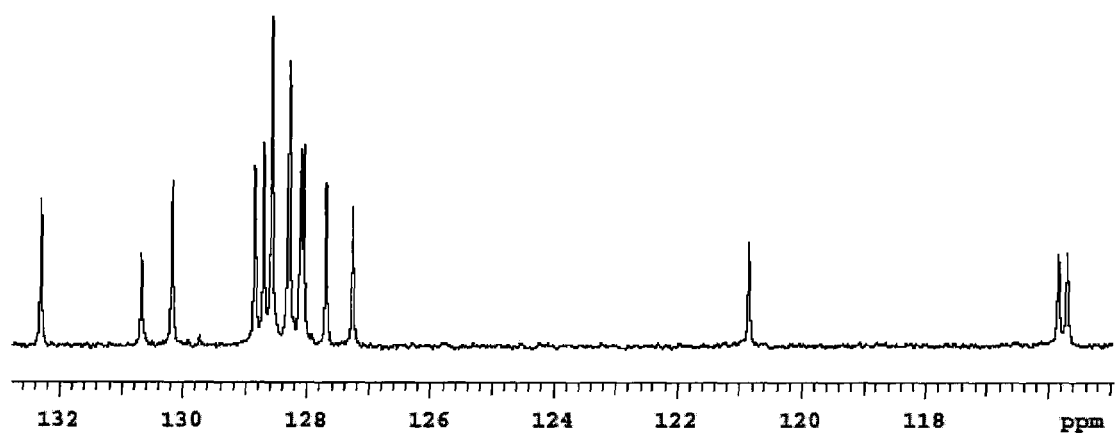

FIG. 85. DHA-dopamine $^{13}$C NMR (125 MHz, CDCl$_3$), 115 ppm to 133 ppm.

Figure 86:
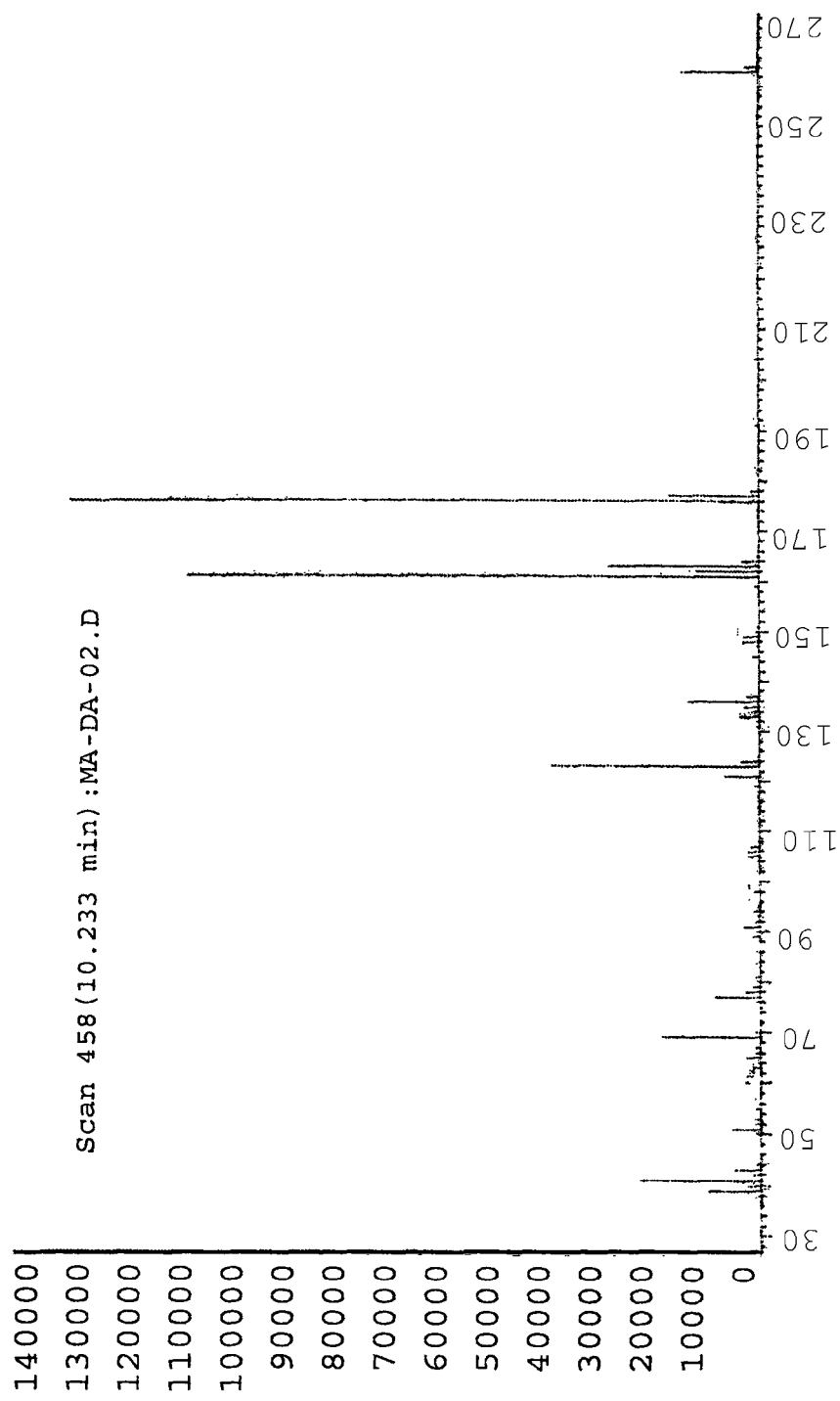

FIG. 86. MA-dopamine(acetonide).

Figure 87:
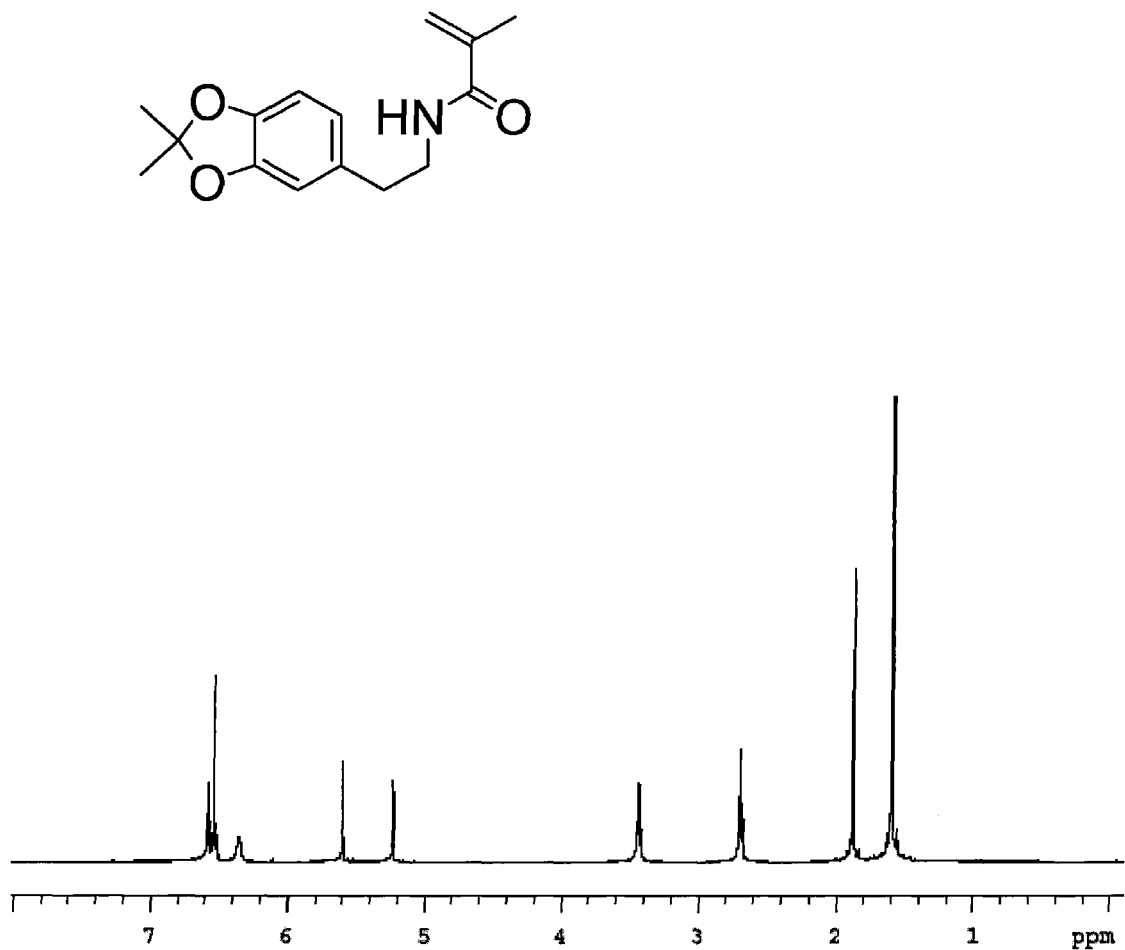

FIG. 87. MA-dopamine(acetonide) $^1$H NMR (500 MHz, CDCl$_3$).

Figure 88:
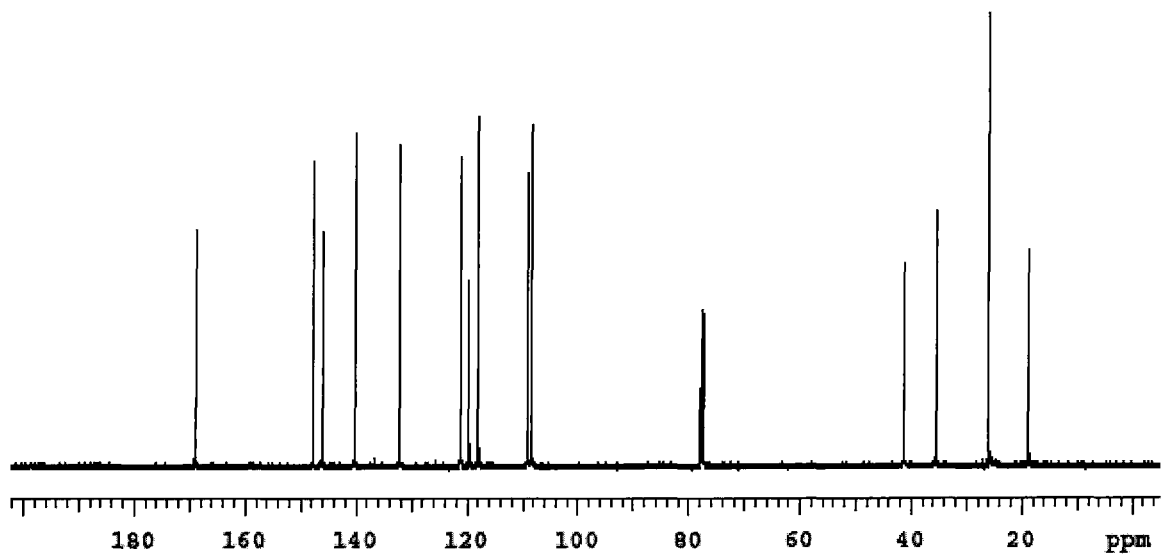

FIG. 88. MA-dopamine(acetonide) $^{13}$C NMR (125 MHz, CDCl$_3$).

FIG. 89. DHCA(Chex)-OMe $^1$H NMR (500 MHz, CDCl$_3$).

Figure 90:
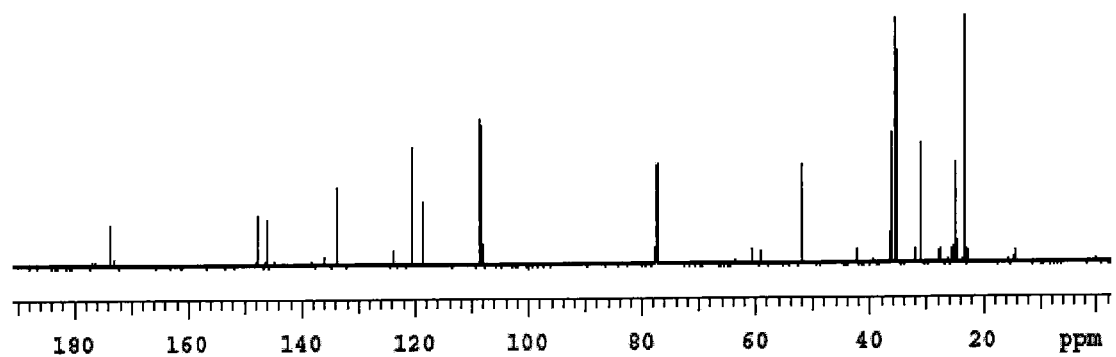

FIG. 90. DHCA(Chex)-OMe $^{13}$C NMR (125 MHz, CDCl$_3$).

Figure 91:
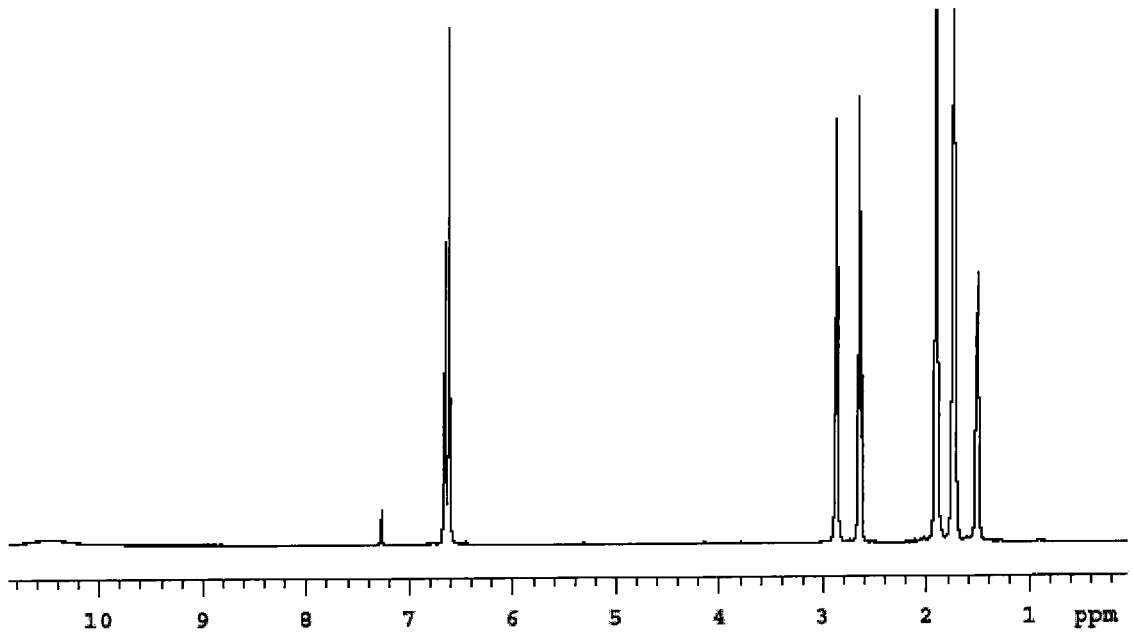

FIG. 91. DHCA(Chex)-OH $^1$H NMR (500 MHz, CDCl$_3$).

Figure 92:
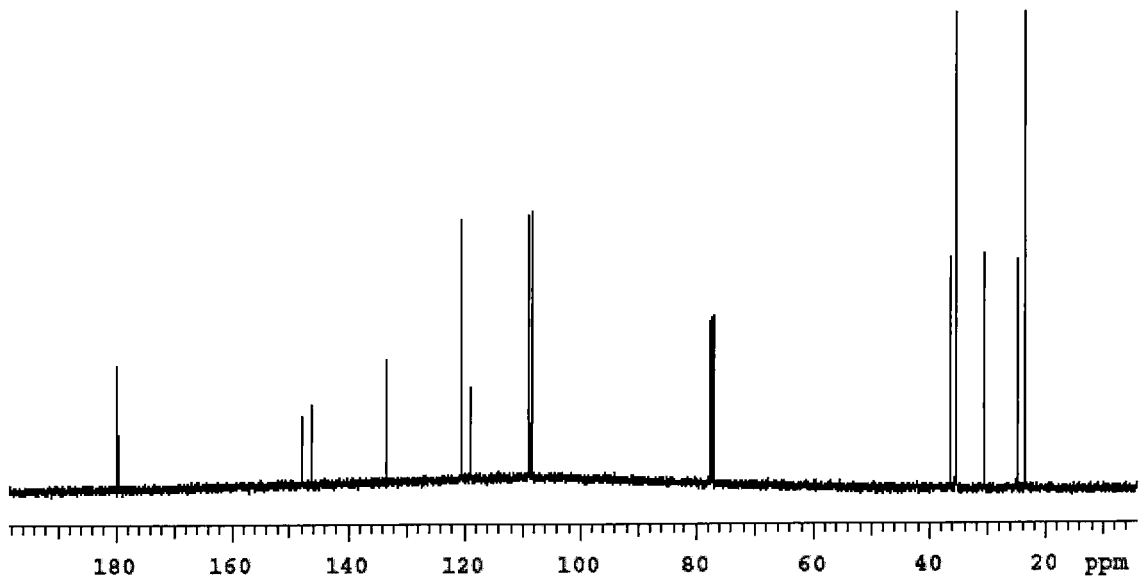

FIG. 92. DHCA(Chex)-OH $^{13}$C NMR (125 MHz, CDCl$_3$).

FIG. 93. DHCA(Chex)-OSu $^1$H NMR (500 MHz, CDCl$_3$).

Figure 94:
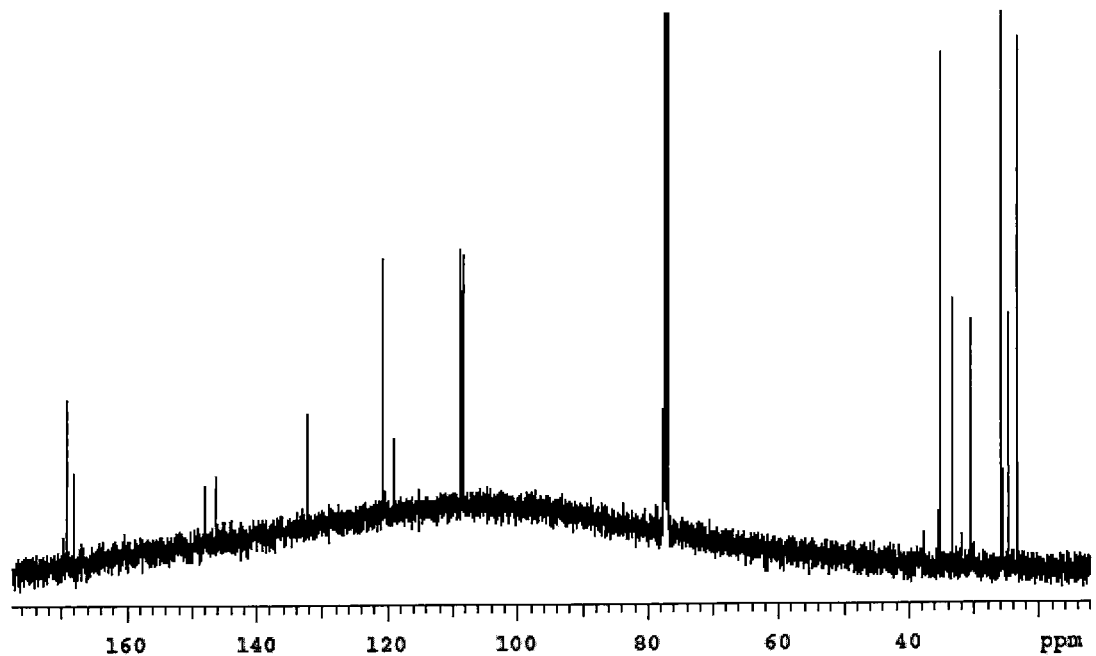

FIG. 94. DHCA(Chex)-OSu $^{13}$C NMR (125 MHz, CDCl$_3$).

SUMMARY OF THE INVENTION

The inventors disclose here a novel, facile approach to the synthesis of acetonide-protected catechol-containing compounds having at least one amine group. In specific embodiments, the invention provides novel methods of synthesizing 3,4-dihydroxyphenylalanine (H-DOPA(acetonide)-OH (6)), Fmoc-protected H-DOPA(acetonide)-OH (Fmoc-DOPA(acetonide)-OH (7)), Fmoc-protected dopamine (Fmoc-dopamine(acetonide) (10)), TFA-protected dopamine (TFA-dopamine(acetonide) (13)) and acetonide-protected 4-(2-aminoethyl)benzene-1,2-diol (acetonide-protected dopamine (14)).

In one embodiment, the present invention describes a method of preparing optically pure acetonide-protected 3,4-dihydroxyphenylalanine (H-DOPA(acetonide)-OH (6)). The method comprises protecting the amine group of L-DOPA with a phthaloyl group to yield Phth-DOPA-OH (2); protecting the carboxyl group of Phth-DOPA-OH (2) with a methyl ester to yield Phth-DOPA-OMe (3); converting Phth-DOPA-OMe (3) via acetonide cyclization to yield Phth-DOPA(acetonide)-OMe (4); and deprotecting Phth-DOPA(acetonide)-OMe (4) to yield optically pure H-DOPA(acetonide)-OH (6).

The step of protecting the amine group of the L-DOPA may further comprise reacting the L-DOPA with N-carbethoxyphthalimide to yield Phth-DOPA-OH (2). The step of deprotecting Phth-DOPA(acetonide)-OMe (4) further comprises reacting Phth-DOPA(acetonide)-OMe (4) with hydrazine in methanol and dichloromethane. The step of deprotecting Phth-DOPA(acetonide)-OMe (4) further comprises alkaline hydrolysis of Phth-DOPA(acetonide)-OMe (4) by lithium hydroxide in tetrahydrofuran and water. The invention also provides optically pure acetonide-protected 3,4-dihydroxyphenylalanine (H-DOPA(acetonide)-OH) (6) prepared according to the method described above.

In one embodiment of the invention, a method for preparing Fmoc-protected 3,4-dihydroxyphenylalanine (Fmoc-DOPA(acetonide)-OH (7)) is provided. The method comprises protecting the amine group of L-DOPA with a phthaloyl group to yield Phth-DOPA-OH (2); protecting the carboxyl group of Phth-DOPA-OH (2) with a methyl ester to yield Phth-DOPA-OMe (3); converting Phth-DOPA-OMe (3) via acetonide cyclization to yield Phth-DOPA(acetonide)-OMe (4); deprotecting Phth-DOPA(acetonide)-OMe (4) to yield H-DOPA(acetonide)-OH (6); and reacting H-DOPA(acetonide)-OH (6) with Fmoc-OSu to yield optically pure Fmoc-DOPA(acetonide)-OH (7). The invention also provides an optically pure acetonide-protected Fmoc-DOPA(acetonide)-OH prepared according to the method described above.

The invention also provides novel compositions prepared during the synthesis of acetonide- and Fmoc-protected DOPA. In one embodiment, the invention describes intermediate useful in the synthesis of H-DOPA(acetonide)-OH (6) selected from Phth-DOPA(acetonide)-OMe (4) or H-DOPA(acetonide)-OMe (5a).

In an alternate embodiment the present invention provides intermediates useful in the synthesis of Fmoc-DOPA(acetonide)-OH selected from Phth-DOPA(acetonide)-OMe (4), H-DOPA(acetonide)-OMe (5a), or mixtures thereof.

In an alternate embodiment, the present invention provides a method of carrying out Fmoc-Solid Phase Peptide Synthesis (SPSS) to provide a DOPA-containing peptide product. The method comprises attaching a Fmoc-protected amino acid to a resin; deprotecting the amino acid to yield a deprotected amino acid; coupling another Fmoc-protected amino acid to the deprotected amino acid; and repeating the deprotecting and coupling steps to yield an elongating peptide. The method further includes the steps of incorporating Fmoc-DOPA(acetonide)-OH prepared according to the method described above at any point in the elongating peptide to yield a DOPA-containing peptide product. In some embodiments the deprotecting and coupling steps are repeated at least twice. The Fmoc-DOPA(acetonide)-OH may be incorporated into the elongated peptide at any position known to the art, including at either end of the peptide.

In one embodiment, the present invention describes a novel method of providing an acetonide-protected 4-(2-aminoethyl)benzene-1,2-diol (dopamine). The method comprises preprotecting the amine group of dopamine with a protecting group selected from the group consisting of a phthalimide, a carbamate and an amide to yield a protected dopamine product; converting the protected dopamine product of step (a) via acetonide cyclization to yield an acetonide-protected product; and deprotecting the amine group of the acetonide-protected product of step (b) to yield acetonide-protected dopamine. In one embodiment the acetonide cyclization is carried out in the presence of paratoluene sulfonic acid under polar aprotic conditions. However, other catalysts known to the art including $P_2O_5$ and montmorillonite may also be used. Further, the aprotic conditions may also be nonpolar, and known to one of skill in the art. Acetonide-protected dopamine products prepared according to this method are also provided. In one embodiment, an acetonide-protected dopamine preparation is provided where the protecting group is phthalimide, and the resultant acetonide-protected product is Phth-dopamine(acetonide) (9). Where the protecting group is carbamate, the resultant acetonide-protected product is Fmoc-dopamine(acetonide) (10). Where the protecting group is an amide, and the acetonide-protected product is TFA-dopamine(acetonide) (13).

The invention also describes an acetonide-protected dopamine prepared according to the method described herein. In addition, intermediates useful in the synthesis of acetonide-protected dopamine(acetonide) selected from the group consisting of Phth-dopamine(acetonide) (9), Fmoc-dopamine(acetonide) (10) and TFA-dopamine(acetonide) (13) are provided.

In one embodiment, the present invention describes a method of providing an acetonide-protected catechol-containing molecule bearing at least one amine group. The method comprises preprotecting the amine group with a protecting group to yield a protected catechol-containing molecule; converting the protected molecule of step (a) via acetonide cyclization to yield an acetonide-protected molecule; and deprotecting the amine group of the acetonide-protected molecule of step (b) to yield an acetonide-protected catechol-containing molecule. In one embodiment, the protecting group is selected from the group consisting of a phthalimide, a carbamate and an amide, and the catechol-containing compound is selected from the group consisting of 3,4-dihydroxyphenylalanine (DOPA), 4-(2-aminoethyl)benzene-1,2-diol (dopamine), norepinephrine and epinephrine.

While multiple embodiments are disclosed, still other embodiments of the present invention will become apparent to those skilled in the art from the following detailed description. As will be apparent, the invention is capable of modifications in various obvious aspects, all without departing from the spirit and scope of the present invention. Accordingly, the detailed descriptions are to be regarded as illustrative in nature and not restrictive.

DETAILED DESCRIPTION OF THE INVENTION

The inventors disclose here a novel, facile approach to the synthesis of acetonide-protected catechol-containing compounds having at least one amine group. In specific embodiments, the invention provides novel methods of synthesizing 3,4-dihydroxyphenylalanine (H-DOPA(acetonide)-OH (6)), Fmoc-protected H-DOPA(acetonide)-OH (Fmoc-DOPA(acetonide)-OH (7)), Fmoc-protected dopamine (Fmoc-dopamine(acetonide) (10)), TFA-protected dopamine (TFA-dopamine(acetonide) (13)) and acetonide-protected 4-(2-aminoethyl)benzene-1,2-diol (acetonide-protected dopamine (14)).

I. In General

In the specification and in the claims, the terms "including" and "comprising" are open-ended terms and should be interpreted to mean "including, but not limited to . . . ." These terms encompass the more restrictive terms "consisting essentially of" and "consisting of."

As used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprising", "including", "characterized by" and "having" can be used interchangeably.

In the general description, the general chemical terms are all used in their normal and customary meanings. For example, the small alkyl and alkoxy groups, such as $(C_1-C_6)$ alkyl and $(C_1-C_6)$alkoxy groups include, depending on the size of the groups, methyl, ethyl, propyl, isopropyl, n-butyl, s-butyl, pentyl, 3-methylbutyl, hexyl, and branched hexyl groups, and the corresponding alkoxy groups, as may be allowed by the individually named groups. Where a number of possible substituent groups are permitted on a group, such as the one to three alkyl, alkoxy or halo groups permitted on an Ar group, it will be understood by the reader that only substitution which is electronically and sterically feasible is intended.

Unless defined otherwise, all technical and scientific terms used herein have the same meanings as commonly understood by one of ordinary skill in the art to which this invention belongs. All publications and patents specifically mentioned herein are incorporated by reference in their entirety for all purposes including describing and disclosing the chemicals, instruments, statistical analyses and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

II. The Invention

The inventors disclose here a novel, facile approach to the synthesis of acetonide-protected catechol-containing compounds having at least one amine group. In specific embodiments, the invention provides novel methods of synthesizing 3,4-dihydroxyphenylalanine (H-DOPA(acetonide)-OH (6)), Fmoc-protected H-DOPA(acetonide)-OH (Fmoc-DOPA(acetonide)-OH (7)), Fmoc-protected dopamine (Fmoc-dopamine(acetonide) (10)), TFA-protected dopamine (TFA-dopamine(acetonide) (13)) and acetonide-protected 4-(2-aminoethyl)benzene-1,2-diol (acetonide-protected dopamine (14)).

A. DOPA

In the present invention, the inventors provide a novel, facile synthetic method for providing an optically pure acetonide-protected 3,4-dihydroxyphenylalanine (H-DOPA(acetonide)-OH (6)) and an optically pure Fmoc-protected H-DOPA(acetonide)-OH (Fmoc-DOPA(acetonide)-OH (7)) with good yield. Conventional methods of preparing optically pure preparations of acetonide- and Fmoc-protected DOPA have been unsuccessful, resulting in along felt need for successful synthesis methods.

For instance, conventional methods of synthesizing acetonide-protected DOPA have relied on direct protection of the catechol side-chain group of commercially available L-DOPA with 2,2-dimethoxypropane (DMP) and a commonly used catalyst p-toluenesulfonic acid (TsOH). Refluxing the hydrochloride salt of L-DOPA methyl ester with acetone in the presence of TsOH also failed to protect the catechol side-chain catechol of the L-DOPA instead of an isoquinoline product.[17] Further, it has been reported that Fmoc-DOPA-OH could not be converted to the acetonide-protected form.[12]

However, the present invention provides a novel method wherein optically pure preparations of acetonide- and Fmoc-protected DOPA are successfully prepared. The method comprises protecting the amine and carboxyl groups with a phthaloyl group and a methyl ester, respectively, to protect the side-chain catechol group of methyl 3-(3,4-dihydroxyphenyl)propionate with acetonide to yield an optically pure preparation of H-DOPA(acetonide)-OH (6). After subsequent removal of the amine and carboxyl protecting groups, an optically pure preparation of Fmoc-DOPA(acetonide)-OH (7) was successfully achieved.

Acetonide-Protected DOPA.

Figure 1:
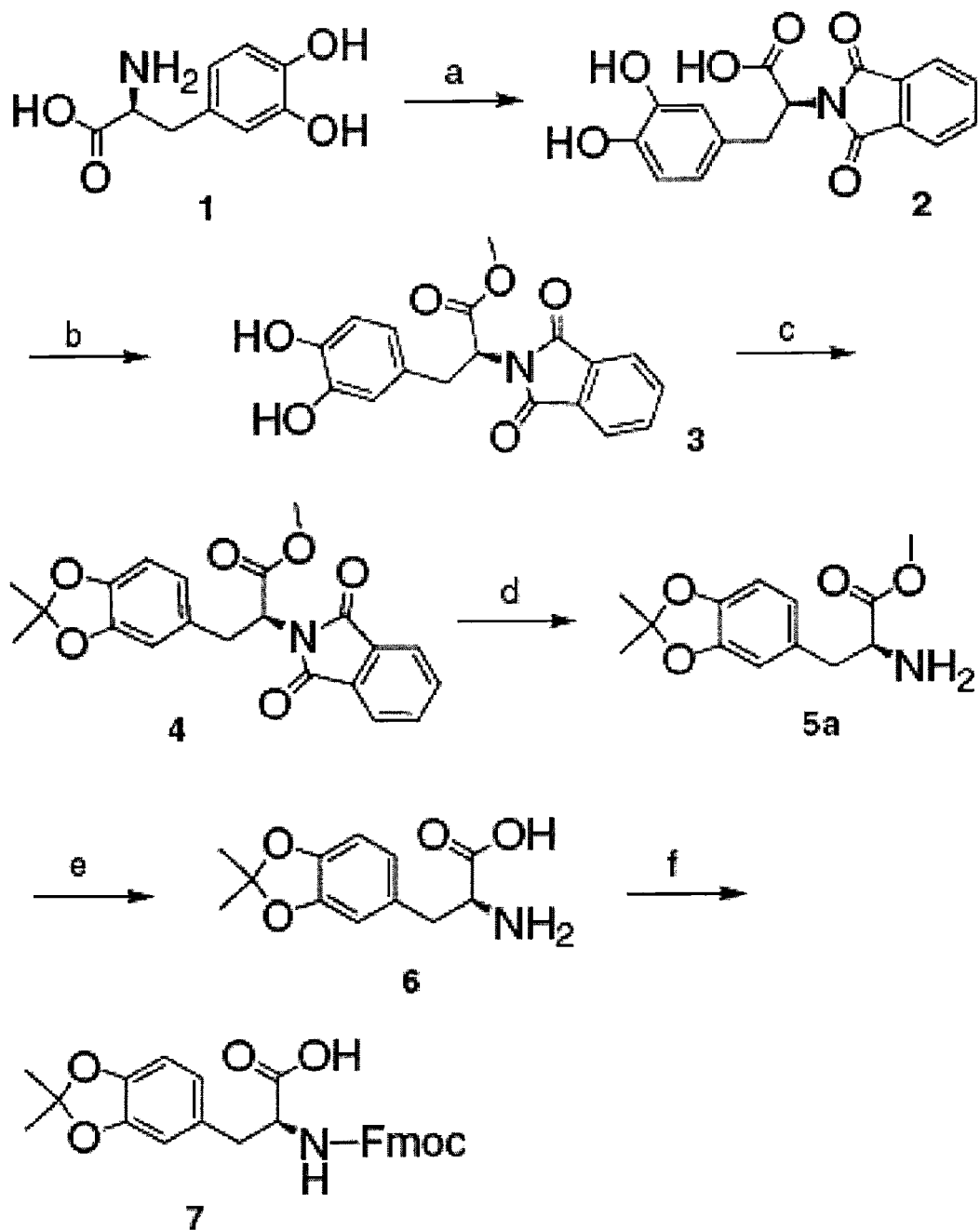
FIG. 1. Synthesis of acetonide-protected DOPA and intermediates. Reagents and conditions: (a) N-carbethoxyphthalimide, Borax, Na2CO3; (b) SOCl2/MeOH, 92% (a and b); (c)

As shown in FIG. 1, in one embodiment, the present invention describes a method of preparing optically pure acetonide-protected 3,4-dihydroxyphenylalanine (H-DOPA (acetonide)-OH (6)). The method comprises protecting the amine group of L-DOPA with a phthaloyl group to yield Phth-DOPA-OH (2); protecting the carboxyl group of Phth-DOPA-OH (2) with a methyl ester to yield Phth-DOPA-OMe (3); converting Phth-DOPA-OMe (3) via acetonide cyclization to yield Phth-DOPA(acetonide)-OMe (4); and deprotecting Phth-DOPA(acetonide)-OMe (4) to yield optically pure H-DOPA(acetonide)-OH (6).

The step of protecting the amine group of the L-DOPA may further comprise reacting the L-DOPA with N-carbethoxyphthalimide to yield Phth-DOPA-OH (2). The step of deprotecting Phth-DOPA(acetonide)-OMe (4) further comprises reacting Phth-DOPA(acetonide)-OMe (4) with hydrazine in methanol and dichloromethane. The step of deprotecting Phth-DOPA(acetonide)-OMe (4) further comprises alkaline hydrolysis of Phth-DOPA(acetonide)-OMe (4) by lithium hydroxide in tetrahydrofuran and water.

By "DOPA" we mean the naturally occurring amino acid 3,4-dihydroxyphenylalanine (DOPA). In nature, DOPA is derived from post-translational modification of tyrosine, and is the biosynthetic precursor of dopamine. It is well known that DOPA is rarely included in proteins. However, it is detected in marine mussel adhesive proteins as well as egg-shell precursor proteins, and it is postulated that the adhesive and cohesive properties of mussel adhesive proteins is attributable to the catechol side chain of DOPA residues. On the other hand, it is well known that many biologically active natural products contain DOPA derivatives as a key structural unit. Thus, not only in biological and medicinal fields but also in the field of synthetic organic chemistry, DOPA derivatives are regarded as a useful building block for design and synthesis of biologically active compounds, such as a-Me-DOPA, b3-H-DOPA, calpain I inhibitor, ribasine alkaloids, benzazepine derivatives, pseudobactin, piperonylsyndnone derivatives, to mention just a few. However, DOPA itself possesses a carboxyl group, an amino group, and a catechol moiety. To construct such desired useful compounds from DOPA, selective and efficient protection/deprotection steps are crucial, yet until now, have been impossible to achieve. Furthermore, the physical and chemical properties of unprotected DOPA, which is hardly soluble in most of organic solvents and is oxidized readily under basic conditions, sometimes make it difficult to synthesize desired DOPA compounds. This is why the efficient and practical synthetic transformation methods of DOPA, including protection/deprotection, are highly demanded.

By "protecting" we mean preserving the catechol group of DOPA for use in subsequence reactions by introducing a "protecting group" which binds to the catechol. Protecting groups protect the vulnerable groups of a given compound via chemical modification of a functional group to obtain chemoselectivity in a subsequent chemical reaction. For instance, in many preparations of delicate organic compounds, some specific parts of their molecules cannot survive the required reagents or chemical environments. Then, these parts, or groups, must be protected.

By "protecting groups" we mean any protecting group known to the art useful in protecting reactant groups during synthesis reactions, including but not limited to the trifluoroacetyl (TFA), the 9-fluorenylmethyloxycarbonyl (Fmoc), the tert-Butyloxycarbonyl (BOC), the 4-toluenesulfonylethyloxycarbonyl (Tsoc), the methylsulfonylethyloxycarbonyl (Meson), the 2-(triphenylphosphono)-ethyloxycarbonyl (Peoc), the 2-cyano-t-butyloxycarbonyl (Cyoc), the cyclohexyl ester (Chex), the benzaldehyde (BA), the benzyl ester (Bzl) and the phthaloyl (Pht) groups. Protecting groups, and their uses in organic synthesis reactions, are well known to those of skill in the art. See, for instance, Greene's Protective Groups in Organic Synthesis, 4th ed., incorporated by reference for all purposes.

By "phthaloyl group" we mean the 1,2-benzenedicarbonyl residue obtained by removing two hydroxyl groups from a phthalic acid. Phthaloyl groups include phthaloyl, isophthaloyl and terephthaloyl. The phthaloyl-protecting group (Phth) has been well-known for the full protection of primary amino groups and can be readily removed with hydrazine,[20] making it compatible with the chemistry of the acetonide-protecting group, which is relatively labile to acids and stable to bases.

By "acetonide" we mean a cyclic acetal formed especially by reaction of acetone with both hydroxyl groups of a diol. Acetonide is commonly used as a protecting group for hydroxyl or alcohol groups.

By "acetonide cyclization" we mean reacting the protected product with paratoluene sulfonic acid under polar aprotic conditions to yield the acetonide-protected product. Using acetonide protecting groups have been shown to be compatible with Fmov SPPS methods, see, for instance, Ogura, Tetrahedron Lett. 1971, 3151-3154 and Statz, et al. J. Am. Chem. Soc. 2005, 127, 7972-7973.

By "aprotic conditions" we mean conditions that stabilize peptide formulations against both chemical and physical degradation. By "polar aprotic solvent" we mean a polar solvent which does not contain acidic hydrogen and does not act as a hydrogen bond donor. Examples of polar aprotic solvents are dimethylsulfoxide (DMSO), dimethylformamide (DMF), hexamethylphosphorotriamide (HMPT), and n-methyl pyrrolidone.

By "deprotecting" we mean removing the protecting group using methods known to one of skill in the art.

By "optically pure" we mean that the composition contains at least 90% by weight of the L-DOPA and 10% by weight or less of the D-DOPA. In preferred embodiments, the composition comprises at least 95% L-DOPA, at least 99%, or at least 99.9% L-DOPA. By "D-DOPA" we mean the dextrodopa, which is similar to L-DOPA (levodopa, 3,4-dihydroxy-L-phenylalanine), but with opposite chirality. While L-DOPA is moderately effective against the loss of natural dopamine in Parkinson's disease, D-DOPA is biologically inactive.

The invention also provides optically pure acetonide-protected 3,4-dihydroxyphenylalanine (H-DOPA(acetonide)-OH) (6) prepared according to the method described above.

Fmoc-Protected DOPA.

As shown in FIG. 1, to prepare an Fmoc-protected DOPA, the amine and carboxyl protecting groups were removed and H-DOPA(acetonide)-OH (6) was reacted with Fmoc-OSu to yield Fmoc-DOPA(acetonide)-OH (7).

Accordingly, in one embodiment of the invention, a method for preparing Fmoc-protected 3,4-dihydroxyphenylalanine (Fmoc-DOPA(acetonide)-OH (7)) is provided. The method comprises protecting the amine group of L-DOPA with a phthaloyl group to yield Phth-DOPA-OH (2); protecting the carboxyl group of Phth-DOPA-OH (2) with a methyl ester to yield Phth-DOPA-OMe (3); converting Phth-DOPA-OMe (3) via acetonide cyclization to yield Phth-DOPA(acetonide)-OMe (4); deprotecting Phth-DOPA(acetonide)-OMe (4) to yield H-DOPA(acetonide)-OH (6); and reacting H-DOPA(acetonide)-OH (6) with Fmoc-OSu to yield optically pure Fmoc-DOPA(acetonide)-OH (7).

The invention also provides an optically pure acetonide-protected Fmoc-DOPA(acetonide)-OH prepared according to the method described above.

By "acetonide cyclization" we mean reacting the protected product with paratoluene sulfonic acid under polar aprotic conditions to yield the acetonide-protected product. Using acetonide protecting groups have been shown to be compatible with Fmov SPPS methods, see, for instance, Ogura, Tetrahedron Lett. 1971, 3151-3154 and Statz, et al. J. Am. Chem. Soc. 2005, 127, 7972-7973.

By "aprotic conditions" we mean conditions that stabilize peptide formulations against both chemical and physical degradation. By "polar aprotic solvent" we mean a polar solvent which does not contain acidic hydrogen and does not act as a hydrogen bond donor. Examples of polar aprotic solvents are dimethylsulfoxide (DMSO), dimethylformamide (DMF), hexamethylphosphorotriamide (HMPT), and n-methyl pyrrolidone.

By "optically pure" we mean that the composition contains at least 90% by weight of the L-DOPA and 10% by weight or less of the D-DOPA. In preferred embodiments, the composition comprises at least 95% L-DOPA, at least 99%, or at least 99.9% L-DOPA. By "D-DOPA" we mean the dextro-dopa, which is similar to L-DOPA (levodopa, 3,4-dihydroxy-L-phenylalanine), but with opposite chirality. While L-DOPA is moderately effective against the loss of natural dopamine in Parkinson's disease, D-DOPA is biologically inactive.

Intermediate Compositions.

The invention also provides novel compositions prepared during the synthesis of acetonide- and Fmoc-protected DOPA. In one embodiment, the invention describes intermediate useful in the synthesis of H-DOPA(acetonide)-OH (6) selected from Phth-DOPA(acetonide)-OMe (4) or H-DOPA(acetonide)-OMe (5a).

In an alternate embodiment the inventor provides intermediates useful in the synthesis of Fmoc-DOPA(acetonide)-OH selected from Phth-DOPA(acetonide)-OMe (4), H-DOPA(acetonide)-OMe (5a), or mixtures thereof. For instance, the novel intermediates provided in the present invention may facilitate synthesis of catechol containing compounds, such as by forming a peptide bond with a carboxyl group or an amine.

Alternate Protecting Groups.

In an alternate embodiment of the present invention, a method of synthesizing protected DOPA using protecting groups other than acetonide is also provided. In one embodiment, a benzylaldehyde (BA) or benzyl ester (Bzl) protecting group is used. By "BA" we mean a benzyl aldehyde used to protect the side-chain carboxyl group of a catechol-containing compound such as DOPA. By "Bzl" we mean a benzyl ester used to protect the side-chain carboxyl group of a catechol-containing compound such as DOPA. Bzl is easily cleaved with liquid HF or by Pd/$H_2$, and is stable to TFA. A Bzl protected-DOPA is especially useful in combination with Boc-protected compounds, because TFA cleaves the Boc group but not the Bzl ester. In contrast, Pd/$H_2$ can cleave the Bzl group but not the Boc group.

In an alternate embodiment, a cyclohexyl ester (Chex) protecting group is used. By "Chex" we mean a cyclohexyl ester used to protect the side-chain carboxyl group of a catechol-containing compound such as DOPA. Chex protecting groups are known to the art (see, for instance, Foye's Principles of Medicinal Chemistry, 5th Edition, incorporated by reference herein.)

Other carboxyl protecting groups known to the art may also be useful in the novel methods of the present invention.

Methods of Use.

To investigate the use of Fmoc-DOPA(acetonide)-OH (7) in Fmoc solid-phase peptide synthesis (SPPS), the synthesized Fmoc-DOPA(acetonide)-OH was incorporated into a short synthetic peptide derivative with satisfactory purity of the peptide product (see examples below).

Accordingly, in an alternate embodiment, the present invention provides a method of carrying out Fmoc-Solid Phase Peptide Synthesis (SPSS) to provide a DOPA-containing peptide product. The method comprises attaching a Fmoc-protected amino acid to a resin; deprotecting the amino acid to yield a deprotected amino acid; coupling another Fmoc-protected amino acid to the deprotected amino acid; and repeating the deprotecting and coupling steps to yield an elongating peptide. The method further includes the steps of incorporating Fmoc-DOPA(acetonide)-OH prepared according to the method described above at any point in the elongating peptide to yield a DOPA-containing peptide product.

In some embodiments the deprotecting and coupling steps are repeated at least twice. In alternate embodiments, the deprotecting and coupling steps are repeated at least 5-1,000 times, at least 10-500 times, at least 20-250 times, at least 50-100 times or at least 20-50 times.

The Fmoc-DOPA(acetonide)-OH may be incorporated into the elongated peptide at any position known to the art, including at either end of the peptide. In one embodiment, the Fmoc-DOPA(acetonide)-OH precedes or follows an amino acid with basic side chains such as lysine or arginine.

By "Fmoc Solid Phase Peptide Synthesis (SPSS)" we mean solid phase peptide synthesis using Fmoc (9-fluorenylmethyloxycarbonyl). SPPS has been the most efficient method for the preparation of peptides since its introduction in 1963 by Bruce Merrifield. The t-Boc amino acid derivatives had been used dominantly for the SPPS until the Fmoc chemistry was introduced to overcome the disadvantages associated with t-Boc chemistry problems, namely repetitive TFA treatment which might catalyze the side reactions and cleave the peptide chain prematurely. In Fmoc synthesis, the growing peptide is subjected to mild base treatment using piperidine to remove the Fmoc group, and TFA is required only for the final deprotection and cleavage from the resin. Fmoc synthesis is generally considered to be more reliable and tends to give the desired peptides in better purities By "resin" we mean any support known to one of skill in the art as useful in Fmoc SPPS, including but not limited to rink amide and trityl resins.

B. Dopamine.

Due to the utility of acetonide-protected dopamine in the synthesis of prodrugs, small molecules, and polymers and the current interest in the development of practical synthetic procedures, there is a great need for an acetonide-protected dopamine for use in solid phase protein synthesis (SPPS).

Conventional methods rely on selective acetylation of the catechol of 3,4-dihydroxyphenylalanine (DOPA) to facilitate protonation of the amine group with hydrogen chloride or bromide.[38] Unfortunately, this method is not likely to work for acetonide protection, because Pictet-Spengler reactions proceed via the initial formation of an iminium cation, usually employing a strong acid as a catalyst, followed by electrophilic substitution.[39] As expected, refluxing dopamine hydrochloride with acetone gives an isoquinoline (FIG. 2).[40]

Accordingly, as seen in FIG. 2, in one embodiment, the present invention describes a novel method of providing an acetonide-protected 4-(2-aminoethyl)benzene-1,2-diol (dopamine). The method comprises preprotecting the amine group of dopamine with a protecting group selected from the group consisting of a phthalimide, a carbamate and an amide to yield a protected dopamine product; converting the protected dopamine product of step (a) via acetonide cyclization to yield an acetonide-protected product; and deprotecting the amine group of the acetonide-protected product of step (b) to yield acetonide-protected dopamine. The acetonide cyclization is carried out in the presence of paratoluene sulfonic acid under polar aprotic conditions. Acetonide-protected dopamine products prepared according to this method are also provided.

By "protecting group" we mean any group known to one of skill in the art as useful in protecting a functional group during reactions. For instance, the protecting groups useful in the present invention include, but are not limited to those selected from the group consisting of a phthalimide, a carbamate and an amide. In one embodiment, the N-phthaloyl (Phth) protective group was introduced to dopamine by N-carbethoxyphthalimide in methanol. In other embodiments, the N-protecting groups include the carbamates Boc and Fmoc and the amide trifluoroacetyl (TFA), which remove only one of the two hydrogen atoms of the amine group.

In one embodiment, an acetonide-protected dopamine preparation is provided where the protecting group is phthalimide, and the resultant acetonide-protected product is Phth-dopamine(acetonide) (9). Where the protecting group is carbamate, the resultant acetonide-protected product is Fmoc-dopamine(acetonide) (10). Where the protecting group is an amide, and the acetonide-protected product is TFA-dopamine (acetonide) (13).

The invention also describes an acetonide-protected dopamine prepared according to the method described herein. In addition, intermediates useful in the synthesis of acetonide-protected dopamine(acetonide) selected from the group consisting of Phth-dopamine(acetonide) (9), Fmoc-dopamine(acetonide) (10) and TFA-dopamine(acetonide) (13) are provided.

C. DHCA.

The present invention also provides novel methods of synthesizing protected catechol-containing compositions such as 3-(3,4-Dihydroxyphenyl)propionic acid, also known as dihydrocaffeic acid (DHCA) (FIG. 11).

DHCA is a nonflavonoid catecholic compound present in many plants. DHCA is present in the diet as part of fruits, tea, coffee, and wine[54]. There is growing interest in the multiple biological and pharmacological properties of nonflavonoid catecholic compounds, such as DHCA. It has been reported that these catecholic acids have anti-inflammatory, antimutagenic, and anticarcinogenic activities. The focus of much of the current research is on their cancer chemoprevention and antioxidant properties [55] However, there is increased attention on the ability of DHCA to induce the production and secretion of nerve growth factor (NGF) in the local tissue of the brain.

DHCA is low-molecular weight compound having the ability to induce the production and secretion of NGF in specific tissues, and can be effective for the therapy of regressive disorders of the central nervous system. DHCA is known to be excellent in the production and secretion of NGF[56]. However, DHCA is hard to absorb, and DHCA concentrations are not retained in blood. These limitations limit the effectiveness of DHCA. Accordingly, a need exists for methods of protecting the carboxyl group of DHCA so that DHCA may be, for instance, coupled with other small molecules of interest to address these limitations.

The inventors also provide novel intermediates and compositions produced as a result of the novel methods of synthesis described herein. The inventors are the first to synthesize DHCA(acetonide)-OH, which can be activated by DCC, EDC, or other carbodiimide and then was coupled with an amine to form a peptide bond; and the first to convert DHCA (acetonide)-OH to its HOSu ester, which can react directly with an amine to form a peptide bond.

D. Catechol-Containing Compounds.

The present invention provides a novel method of preparing protected catechol-containing compounds and novel intermediates therein.

Acetonide-Protected Catechol Compounds.

In one embodiment, the present invention describes a method of providing an acetonide-protected catechol-containing molecule bearing at least one amine group. The method comprises preprotecting the amine group with a protecting group to yield a protected catechol-containing molecule; converting the protected molecule of step (a) via acetonide cyclization to yield an acetonide-protected molecule; and deprotecting the amine group of the acetonide-protected molecule of step (b) to yield an acetonide-protected catechol-containing molecule. In one embodiment, the protecting group is selected from the group consisting of a phthalimide, a carbamate and an amide, and the catechol-containing compound is selected from the group consisting of 3,4-dihydroxyphenylalanine (DOPA), 4-(2-aminoethyl)benzene-1,2-diol (dopamine), norepinephrine and epinephrine.

By "catechol-containing" we mean molecules or compounds including at least one catechol group at any position in the molecule. By "catechol" we mean 1,2-benzenediol, sometimes referred to as "pyrocatechol", which may be represented by the structure:

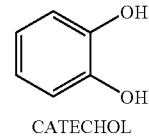

CATECHOL

As a distinct chemical group or moiety, catechol is a key component in a number of different molecules having pharmacological activity and consequently, usefulness as therapeutic agents.

Advantageously, the acetonide-protected catechol-containing molecules of the present invention, and their method of use in, for instance, SPPS, is useful for "designing" improved preparations with specific desired characteristics, such as thermal stability, tensile strength, moldability, elasticity, biodegradability (or lack thereof), compressive strength, or non-antigenicity. Based on the needs of the user, the specific acetonide-protected catechol-containing molecule of the present invention may be modified to achieve the desired characteristic(s).

In one embodiment, the catechol-containing molecule of the present invention bears at least one amine group that is protected prior to acetonide cyclization to yield the acetonide-protected catechol-containing molecule of the present invention. Synthetic chemistry transformations and protecting group methodologies (protection and deprotection) useful in synthesizing the acetonide-protected catechol-containing molecules described herein include, for example, those such as described in R. Larock, Comprehensive Organic Transformations, VCH Publishers (1989); T. W. Greene and P. G. M. Wuts, Protective Groups in Organic Synthesis, 2d. Ed., John Wiley and Sons (1991); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995), and subsequent editions thereof.

By "acetonide cyclization" we mean reacting the protected molecule in the presence of paratoluene sulfonic acid under polar aprotic conditions to yield the acetonide-protected molecule.

Alternate Protecting Groups.

In an alternate embodiment of the present invention, a novel method of synthesizing protected catechol-containing compounds using protecting groups other than acetonide is provided. For instance, in one embodiment the protecting group is benzyl aldehyde (BA) or benzyl ester (Bzl). By "BA" we mean a benzyl aldehyde used to protect the side-chain carboxyl group of DOPA. By "Bzl" we mean a benzyl ester used to protect the side-chain carboxyl group of DOPA. Bzl is easily cleaved with liquid HF or by $Pd/H_2$, and is stable to TFA. A Bzl protected-DOPA is especially useful in combination with Boc-protected compounds, because TFA cleaves the Boc group but not the Bzl ester. In contrast, $Pd/H_2$ can cleave the Bzl group but not the Boc group.

In an alternate embodiment, a cyclohexyl ester (Chex) protecting group is used. By "chex" we mean a cyclohexyl ester used to protect the side-chain carboxyl group. Chex protecting groups are known to the art (see, for instance, Foye's Principles of Medicinal Chemistry, 5th Edition, incorporated by reference herein.)

Other protecting groups known to the art may also be used in the methods of the present invention.

EXAMPLES

The following examples are, of course, offered for illustrative purposes only, and are not intended to limit the scope of the present invention in any way. Indeed, various modifications of the invention in addition to those shown and described herein will become apparent to those skilled in the art from the foregoing description and the following examples and fall within the scope of the appended claims.

Example 1

Acetonide-Protected DOPA

In this example, the inventors demonstrate the synthesis procedures of acetonide-protected DOPA of the present invention.

The starting material L-DOPA (1) was dissolved in borax buffer and the pH of the solution was adjusted to 9.5 by addition of sodium carbonate, which provides a temporary protection of the catechol group through the complexation between boric acid and the catechol group.[20] N-Carbethoxyphthalimide was added and the mixture was stirred overnight to give Phth-DOPA-OH (2). Phth-DOPA-OH (2) was reacted with $SOCl_2$/methanol to produce Phth-DOPA-OMe (3) (yield ca. 92% for two steps).[21] Phth-DOPA-OMe (3) was refluxed with DMP in anhydrous benzene in the presence of TsOH (4.5% molar ratio) as a catalyst. Since the acetonide cyclization is controlled by equilibria, it is necessary to remove the generated byproduct from the reaction system. For this purpose, the reaction flask was equipped with a Soxhlet extractor, the thimble of which was filled with anhydrous $CaCl_2$ to trap water and the methanol produced during the reaction.[18] The reaction was monitored by the $FeCl_3$ test and was usually completed in 1.5-3 h.

After removing the solvents and re-crystallization in dichloromethane (DCM)/hexane, Phth-DOPA(acetonide)-$OMe_2^3$ (4) was obtained as white crystals (yield 83%). 13C NMR spectrum of Phth-DOPA(acetonide)-$OMe_2^3$ (4) showed a signal at dppm 117.8, typical for the quaternary carbon of an acetonide-protecting group of catechol (Table 1).

TABLE 1

| NMR Data | | | |
|---|---|---|---|
| Compound | $\delta^a$ | Ferric Chloride Test | |
| 3 | N.A. | Positive[b] | N.A. |
| 4 | 117.8 | Negative[b] | Positive[c] |
| 5a | 117.8 | Negative[b] | Positive[c] |
| 7 | 118.2 | Negative[b] | Positive[c] |

[a]13C NMR chemical shift (ppm) of the quaternary C of the acetonide-protecting group.
[b]Tests were performed at room temperature.
[c]Tests were performed at 105° C. for 10 min.

Deprotecting the phthaloyl group using hydrazine[23] in MeOH/DCM (1:1) at 2° C. afforded H-DOPA(acetonide)-OMe (5a) (yield 56%). To produce a hydrochloride salt (5b) of H-DOPA(acetonide)-OMe (5a), the intermediate was dissolved in 0.1 N HCl solution and subjected to freeze drying. Alkaline hydrolysis of H-DOPA(acetonide)-OMe (5a) by lithium hydroxide[23] in THF/H2O (3:1) provided H-DOPA(acetonide)-OH, which was used without further purification. The mixture solution was neutralized with 1 N HCl to pH 7-8, followed by addition of sodium carbonate (2 equiv) and Fmoc-OSu (1 equiv) to provide Fmoc-DOPA(acetonide)-OH (7), which was further purified by silica-gel flash chromatography (DCM/EtOAc/MeOH) (two steps, 74%).[24]

Synthesis of Phth-DOPA(acetonide)-OMe (4).

As shown in FIG. 1, step c, borax (10 g, 50 mmol), water (250 mL), and a magnetic stirring bar were added to a 500 ml flask. The mixture was degassed with argon for 30 min. Then L-DOPA (19.7 g, 100 mmol) was added, followed by $Na_2CO_3$ (10.6 g, 100 mmol) and N-Carbethoxyphthalimide (26.6 g, 121 mmol) in 100 mL of THF. The mixture was stirred overnight at room temperature, and then was acidified to pH 1-2 with 1N HCl solution. THF was reduced by rotary evaporation and the mixture was extracted with EtOAc. The organic layer was washed with water, dried over $MgSO_4$, and evaporated to afford a yellow solid.

The above solid was dissolved in methanol (250 mL) in a 500 mL flask, which was cooled in an acetonitrile/dry ice bath. Thionyl chloride (14.6 mL, 200 mmol) was added dropwise in 5 min. The cooling bath was removed and the mixture was stirred overnight at room temperature. After the volatile materials were removed, the residue was dissolved in chloroform (100 mL), followed by addition of hexane (300 mL), and stored in a refrigerator overnight. The liquid was poured off and the residue was dried by vacuum to yield a light brown solid, 31.3 g (92%, impure).

To a two-necked 500 mL flask were added 17.1 g (50 mmol) of the above solid, 2,2-dimethoxypropane (25 mL, 200 mmol), and anhydrous benzene (350 mL). One neck of the flask was fitted with a Soxhlet extractor, the thimble of which was filled with granular anhydrous $CaCl_2$ (75 g) to trap MeOH and $H_2O$. The other neck of the flask was sealed with a septum for sampling. After the system was flushed with argon for 5 min and then heated to reflux for 5 min, p-toluenesulfonic acid monohydrate (430 mg, 4.5 mol %) was added. The reaction was monitored by the ferric chloride test. Once a negative test was achieved, usually 1.5 to 3 h, the reflux was stopped. After cooling to room temperature, the yellow solution was filtered through a short silica-gel column, which was washed with DCM/EtOAc. The combined filtrate and washings were evaporated to yield a yellow solid, which was re-crystallized in DCM/hexane to produce a white crystalline solid, 15.8 g (83%).

Spectral Data. $^1$H NMR (500 MHz, $CDCl_3$): δ 7.79 (m, 2H), 7.69 (m, 2H), 6.57-6.51 (m, 3H), 5.08 (dd, 1H), 3.77 (s, 3H), 3.47 (m, 2H), 1.59 (s, 3H), 1.55 (s, 3H). $^{13}$C NMR (125 MHz, $CDCl_3$): δ 169.5, 167.6 (2C), 147.6 (2C), 146.4, 134.2 (2C), 131.8, 129.8, 123.6 (2C), 121.5, 117.8,[1] 109.2, 108.2, 53.6, 53.0, 34.5, 25.87, 25.82. $^{13}$C NMR (125 MHz, $CDCl_3$) DEPT: CH3, 53.0, 25.87, 25.82; CH2, 34.5; CH, 134.2 (2C), 123.6 (2C), 121.5, 109.2, 108.2. GC-MS: m/z 381 (11.8%), 235 (14.1%), 234 (100%), 219 (47.1%), 163 (60%), 130 (10.7%), 123 (38.3%). Ferric Chloride Test: negative at room temperature, positive at 105° C. Anal. for $C_{21}H_{19}NO_6$: Calcd C, 66.13; H, 5.02; N, 3.67; Found C, 66.05; H, 5.06; N, 3.65. HRMS (ESI): $C_{21}H_{19}NO_6$, $MH^+$, Calcd 382.12851, Found 382.12851. mp 127-128° C. (FIGS. 21-23).

Synthesis of H-DOPA(acetonide)-OMe (5a)

The reaction was carried out in a refrigerated cabinet (a constant temperature of 2° C.). To a 500 mL round bottom flask were added Phth-DOPA(acetonide)-OMe (4) (3.8 g, 10 mmol), 120 mL MeOH and 120 mL DCM. After the solution was cooled to 2° C., hydrazine monohydrate (5 mL, 100 mmol) was added. The flask was sealed by a septum and the mixture was stirred overnight. The mixture was reduced to ca. 50 mL by rotary evaporation, followed by addition of 50 mL water, acidified with 1N HCl to pH 1-2. The mixture was stirred at 2° C. for another 3 h. The white precipitate was filtered off and the filtrate was washed with DCM, which was reverse-extracted by 0.1 N HCl. The combined aqueous solution was adjusted to pH 8 with $NaHCO_3$, and then extracted by EtOAc. The organic phase was washed with water, dried over $MgSO_4$, and concentrated to give an oil residue, 1.4 g (56%).

Spectral Data. $^1$H NMR (500 MHz, $CDCl_3$): δ 6.61-6.55 (m, 3H), 3.64 (s, 3H), 3.63 (s, 1H), 2.95 (m, 1H), 2.72 (m, 1H), 1.62 (s, 6H); $^{13}$C NMR (125 MHz, $CDCl_3$): δ 175.5, 147.6, 146.3, 130.1, 121.7, 117.8, 109.3, 108.1, 55.9, 52.0, 40.8, 25.9 (2C); $^{13}$C NMR (125 MHz, $CDCl_3$) DEPT: CH3, 52.0, 25.9; CH2, 40.8; CH, 121.7, 109.3, 108.1, 55.9. GC-MS: m/z 251 (7.6%), 192 (10.5%), 164 (18.3%), 163 (100%), 123 (41.2%), 121 (11.8%). Ferric Chloride Test: negative at room temperature, positive at 105° C. HRMS (ESI): $C_{13}H_{17}NO_4$, $MH^+$, Calcd. 252.12303, Found 252.12223; $MNa^+$, Calcd. 274.10498, Found 274.10524 (FIGS. 24-25).

Synthesis of the hydrochloride salt of H-DOPA(acetonide)-OMe (5b)

Phth-DOPA(acetonide)-OMe (4) (oil form, 0.40 g, 1.6 mmol) was dissolved in 16 mL 0.1 N HCl. A very small amount of insoluble solid was filtered off. The filtrate was lyophilized to produce a white solid, 0.44 g (96%).

Spectral Data. $^1$H NMR (500 MHz, $CD_3OD$): δ 6.70-6.65 (m, 3H), 4.26 (dd, 1H), 3.81 (s, 3H), 3.18-3.06 (m, 2H), 1.63 (s, 6H). $^{13}$C NMR (125 MHz, $CD_3OH$): δ 170.6, 149.6, 148.8, 128.2, 123.5, 119.6, 110.35 (d, 1C), 109.6, 55.45 (d, 1C), 53.74 (d, 1C), 37.2, 26.08(dd, 2C). $^{13}$C NMR (125 MHz, $CD_3OD$) DEPT: CH3, 53.74, 26.08; CH2, 37.2; CH, 123.5, 110.35, 109.6, 55.45. HMQC δH (δC): 1.63 (26.08, $^1J_{C-H}$), 3.18-3.06 (37.2, $^1J_{C-H}$), 3.81 (53.74, $^1J_{C-H}$), 4.26 (55.45, $^1J_{C-H}$). HMBC δH (δC): 1.63 (26.08, $^3J_{C-H}$; 119.6, $^2J_{C-H}$), 3.18-3.06 (55.45, $^2J_{C-H}$; 109.6, $^3J_{C-H}$, 110.35, $^3J_{C-H}$; 123.5, $^3J_{C-H}$; 128.2, $^2J_{C-H}$), 3.81 (170.6, $^3J_{C-H}$), 4.26 (37.2, $^2J_{C-H}$; 128.3, $^3J_{C-H}$; 170.6, $^2J_{C-H}$). mp 166-168° C., decompose (FIGS. 26-29).

Synthesis of H-DOPA(acetonide)-OH (6)

H-DOPA(acetonide)-OH (6) is an intermediate produced in the synthesis of Fmoc-DOPA(acetonide)-OH (7). Because H-DOPA(acetonide)-OH (6) is a free amino acid that is difficult to purify, it does not need to be isolated to produce Fmoc-DOPA(acetonide)-OH (7). However, the present invention provides methods of isolating H-DOPA(acetonide)-OH (6) and characterizing it according to chemistry reaction rules.

The novel methods of the present invention provides two ways to obtain H-DOPA(acetonide)-OH (6). In one embodiment, the deprotection of H-DOPA(acetonide)-OMe (5a) yielded Fmoc-DOPA(acetonide)-OH (7) following addition of Fmoc group. The synthesis is described below in the synthesis of Fmoc-DOPA(acetonide)-OH In an alternate embodiment, H-DOPA(acetonide)-OH (6) was obtained by deprotecting TFA-DOPA(acetondie)-OMe by LiOH in one step. H-DOPA(acetonide)-OH (6) was not isolated but was converted directly to Fmoc-DOPA(acetonide)-OH or Boc-DOPA(acetonide)-OH. In use, after cleavage of the protecting groups of the amino and carboxyl groups, TFA-DOPA(acetonide)-OMe (3.47 g, 10 mmol), THF (60 mL), and a magnetic stirring bar were added to a 250 ml flask. The flask was cooled in an ice bath. Lithium hydroxide (720 mg, 3 equiv) in water (20 mL) was added and the mixture was stirred for 2.5 h. The reaction was monitored by TLC, yielding H-DOPA(acetonide)-OH (6) (FIG. 30).

Synthesis of Fmoc-DOPA(acetonide)-OH (7)

The oil residue of H-DOPA(acetonide)-OMe (0.50 g, 2 mmol) was dissolved in 20 mL THF and cooled in an ice bath. Lithium hydroxide (0.96 g, 4 mmol) in cold water (7 mL) was added. The mixture was stirred at 0° C. for 2.5 h, treated with 1N HCl to a pH of 7-8, followed by addition of $Na_2CO_3$ (0.42 g, 4 mmol). Fmoc-OSu (0.68 g, 2 mmol) was added and the mixture was stirred at 0° C. for another 2 h. The mixture was then acidified with 1N HCl to a pH of 2-3. After THF was reduced by rotary evaporation, the mixture was extracted with EtOAc. The organic phase was washed with water, dried over $MgSO_4$, concentrated to minimum amount. To the residue was added hexane, and the white precipitate was collected and purified by silica-gel flash chromatography (washed with DCM, and then eluted with DCM/EtOAc/MeOH (67:30:3), yield, 0.66 g (74%).

Spectral Data. $^1$H NMR (500 MHz, $CDCl_3$): δ 11.15 (br, 1H), 7.81-7.28 (m, 8H), 6.71-6.54 (m, 3H), 5.41 (d, 1H), 4.72 (m, 1H), 4.52-4.24 (m, 3H), 3.18-3.06 (m, 2H), 1.67 (s, 6H). $^{13}$C NMR (125 MHz, $CDCl_3$): δ 176.5, 156.1, 147.8, 146.8, 143.92, 143.81, 141.4 (2C), 128.6, 127.9 (2C), 127.3 (2C), 125.28, 125.22, 122.1, 119.9 (2C), 118.2, 109.6, 108.4, 67.3, 54.9, 47.2, 37.6, 26.0 (2C). $^{13}$C NMR (125 MHz, CDCl$_3$) DEPT: CH3, 26.0; CH2, 67.3, 37.6; CH, 127.9, 127.3, 125.28, 125.22, 122.1, 119.9, 109.6, 108.4, 54.9, 47.2. Ferric Chloride Test: negative at room temperature, positive at 105° C. ESI-MS: MH$^+$, Calcd. 460.18. Found 459.85; M$_2$Na$^+$, Calcd. 941.33, Found 940.77. M$_3$Na$^+$, Calcd. 1400.49, Found 1400.49; M$_4$Na$^+$, Calcd. 1860.67, Found 1859.36. HRMS (ESI): C$_{27}$H$_{25}$NO$_6$, MH$^+$, Calcd. 460.17546, Found 460.17516 (FIG. 31).

Example 2

Synthesis of Fmoc-DOPA(acetonide)-OH (7)

In this example, the inventors provide novel methods of synthesis of acetonide-protected DOPA for Fmoc solid phase peptide synthesis (FIG. 2).

Synthesis of TFA-DOPA-OH (19)

As seen in FIG. 2, step a, TFA-DOPA-OH (19) is synthesized by adding L-DOPA (39.4 g, 200 mmol), anhydrous MeOH (300 mL), and a magnetic stirring bar to a 1000 ml flask. The mixture was degassed with argon for 30 min, followed by addition of methyl trifluoroacetate (60 mL, 600 mmol) and triethylamine (112 mL, 800 mmol). The mixture was stirred at room temperature overnight. The volatile solvents were reduced by rotary evaporation and the residue was treated with 1 N HCl to a pH of ca. 1 and extracted with EtOAc. The organic layer was washed with 1N HCl and water, dried over MgSO4, and evaporated to give an off-white solid, 51.5 g (95%).

Synthesis of TFA-DOPA-OMe (20)

As seen in FIG. 2, step b, TFA-DOPA-OH (19) (50 g, 170 mmol), DMF (300 mL), and a magnetic stirring bar were added to a 500 ml flask. The mixture was degassed with argon for 30 min, followed by addition of potassium bicarbonate (34 g, 340 mmol) and methyl iodide (21 mL, 340 mmol). The mixture was stirred overnight at room temperature. After DMF was removed by evaporation under high vacuum, the residue was treated with 1 N HCl to a pH of 2 and extracted with EtOAc. The organic layer was washed with 1N HCl and water, dried over MgSO$_4$, and evaporated to give a white solid, 49.6 g (95%).

Spectral Data. $^1$H NMR (500 MHz, DMSO-d$_6$): 9.85(d, 1H)), 8.79(s,1H), 8.76(s, 1H), (catecholic and amide protons), 6.62-6.59 (m, 2H), 6.46-6.44(m, 1H), 4.46 (m, 1H), 3.65 (s, 3H), 3.37 (s, water), 3.01-2.97 (m, 1H), 2.85-2.80 (m, 1H). $^{13}$C NMR (DMSO-d$_6$): δ ppm 170.6, 156.3 (q, $_2$J$_{CF}$=36.6 Hz, 1C), 145.1, 144.0, 127.5, 119.8, 116.3, 115.7 (q, $^1$J$_{CF}$=286.8 Hz, 1C), 115.4, 54.4, 52.4, 35.1.

Synthesis of TFA-DOPA(acetonide)-OMe (21)

As seen in FIG. 2, step c, TFA-DOPA-OMe (20) (11.4 g, 37 mmol), 2,2-dimethoxypropane (DMP) (19 mL, 150 mmol), and anhydrous benzene (350 mL) were added to a two-neck 500 ml flask. One neck of the flask was fitted with a Soxhlet extractor, the thimble of which was filled 28 g with granular anhydrous CaCl$_2$; and the other neck of the flask was sealed with a septum for sampling purpose. After the flask was flushed with argon for 5 min and then heated to reflux for 5 min, catalyst p-toluenesulfonic acid monohydrate (240 mg, 3.4 mol %) was added. The course of the reaction was monitored by ferric chloride test. Once a negative test was obtained, usually 1 to 2 h, the reflux was stopped. After cooled down, the light yellow solution was filtered through a short silica-gel column, which was washed with DCM/EtOAc. The combined filtrate and washings were evaporated to give a yellow solid, which was recrystallized in DCM/hexane to produce white crystals, 10.3 g (80%).

Spectral Data. $^1$H NMR (500 MHz, CDCl$_3$): δ ppm 6.91 (br, 1H), 6.64 (d, 1H), 6.48-6.45 (m, 2H), 4.816 (q, 1H), 3.79 (s, 3H), 3.14-3.11 (m, 1H), 3.08-3.04 (m, 1H), 1.65 (s, 6H). $^{13}$C NMR (CDCl$_3$): δ ppm 170.6, 156.5 (q, $^2$J$_{CF}$=37.8 Hz, 1C), 148.0, 147.1, 127.6, 121.9, 118.4, 115.8 (q, $^1$J$_{CF}$=285.7 Hz, 1C), 109.3, 108.5, 53.8, 53.0, 37.1, 25.9 (2C). $^{19}$F NMR (CDCl$_3$): δ ppm −76.368. GC-MS: m/z 347 (12.7%), 218.95 (8.1%), 164 (11.1%), 163 (100%), 123 (35.6%), 121 (10.0%), 69 (10.9%). HRMS (ESI): C$_{15}$H$_{16}$NO$_5$F$_3$, MH$^+$, Calcd 348.10533, Found 348.10502, Diff. 0.9 ppm. Anal. for C$_{15}$H$_{16}$NO$_5$F$_3$: Calcd C, 51.88; H, 4.64; N, 4.03; Found C, 51.92; H, 4.63; N, 4.01; (FIGS. 32-40).

Cleavage of the Protecting Groups of the Amino and Carboxyl Groups.

As seen in FIG. 2, step d, TFA-DOPA(acetonide)-OMe (21) (3.47 g, 10 mmol), THF (60 mL), and a magnetic stirring bar were added to a 250 ml flask. The flask was cooled in an ice bath. Lithium hydroxide (720 mg, 3 equiv) in water (20 mL) was added and the mixture was stirred for 2.5 h. The reaction was monitored by TLC.

Synthesis of Fmoc-DOPA(Acetonide)-OH (7)

As seen in FIG. 2, step e, the above mixture was neutralized with 1N HCl to a pH of 7-8, followed by addition of Na$_2$CO$_3$ (2.12 g, 2 equiv), Fmoc-OSu (3.37 g, 1 equiv). The mixture was stirred for another 2 h at 0° C. The mixture was acidified with 1N HCl to a pH of ca. 3, extracted with EtOAc, washed by water, dried over MgSO$_4$, and concentrated to minimum amount. The residue was added with hexane and stored in refrigerator for 2 h. The white solid was collected by filtration, 3.8 g (two steps, 85%).

Example 3

Protected-DOPA Using Other Protecting Groups

In this example, the inventors describe using alternate protecting groups to yield a protected DOPA suitable for Fmoc solid phase peptide synthesis (FIG. 3).

Synthesis of TFA-DOPA(Chex)-OMe (22)

As seen in FIG. 3), TFA-DOPA-OMe (20) (15.2 g, 50 mmol) was refluxed with DMCH (30.4 mL, 4 equiv) in benzene (400 mL) in the presence of TsOH (400 mg, 4.2 mol %). After purification by silica-gel flash chromatography (DCM/EtOAc), the resulting TFA-DOPA(Chex)-OMe was a colorless oil, 17.4 g (90%).

Spectral Data. $^1$H NMR (CDCl$_3$): δ ppm 7.0 (br, 1H), 6.64-6.62 (m, 1H), 6.46-6.45 (m, 2H), 4.80 (d, 1H), 3.78 (s, 3H), 3.13-3.09 (m, 1H), 3.06-3.02 (m, 1H), 1.87 (t, 4H), 1.70 (m, 4H), 1.48 (m, 2H). $^{13}$C NMR (CDCl$_3$): δ ppm 170.6, 156.73 (q, $^2$J$_{C-F}$=37.6 Hz), 148.1, 147.1, 127.4, 121.7, 119.1, 115.83 (q, $^1$J$_{C-F}$=286.5 Hz), 109.2, 108.4, 53.8, 52.9, 37.1, 35.2, 24.6, 23.2 (2C). DEPT: CH3, 52.9; CH2, 37.1, 35.2, 24.6, 23.2; CH, 121.7, 109.2, 108.4, 53.8. $^{19}$F NMR (CDCl$_3$): δ −76.380. GC-MS: m/z 387 (4.1%), 204 (14.9%), 203 (100%), 204 (14.9%), 123 (26.4%), 81 (26.4%), 79

(16.5%), 69 (13.9%). HRMS (ESI): $C_{18}H_{20}NO_5F_3$, $MH^+$, Calcd. 388.13663, Found 388.13653, Diff. 0.26 ppm.

Synthesis of Fmoc-DOPA(Chex)-OH (23)

As seen in FIG. 3), To a 250 mL flask were added TFA-DOPA(Chex)-OMe (22) (3.87 g, 10 mmol), THF (60 mL), and a magnetic stirring bar. The flask was cooled in an ice bath. Lithium hydroxide (720 mg, 3 equiv) in water (20 mL) was added and the mixture was stirred for ca. 2.5 h. The mixture was neutralized with 1N HCl to a pH of 7-8, followed by addition of $Na_2CO_3$ (2.12 g, 2 equiv) and Fmoc-OSu (3.37 g, 1 equiv). The mixture was stirred for another 2 h at 0° C. The mixture was carefully acidified with 1N HCl to a pH of ca. 3, extracted with EtOAc, washed with water, dried over $MgSO_4$, and concentrated to minimum amount. The residue was added with hexane and stored in refrigerator for 2 h. The white solid was collected by filtration, 4.1 g (two steps, 82%).

Spectral Data. $^1H$ NMR ($CDCl_3$): δ 11.48 (br, 1H), 7.81-7.35 (m, 8H), 6.72-6.59 (m, 3H), 5.46 (d, 1H), 4.74 (d, 1H), 4.51 (d, 1H), 4.32 (s, 1H), 4.17 (s, 1H), 3.16 (s, 1H), 3.10 (s, 1H), 1.92 (s, 4H), 1.75 (s, 4H), 1.53 (s, 2H). $^{13}C$ NMR ($CDCl_3$): δ 176.4, 156.0, 147.9, 146.8, 143.90, 143.78, 141.4 (2C), 128.4, 127.8 (2C), 127.2 (2C), 125.27, 125.21, 121.9, 120.1 (2C), 118.8, 109.5, 108.3, 67.3, 54.8, 47.2, 37.6, 35.3 (2C), 24.6, 23.3 (2C). DEPT: CH2, 67.3, 37.6, 35.3, 24.6, 23.3; CH, 127.8, 127.2, 125.27, 125.21, 121.9, 120.1, 109.5, 108.3, 54.8, 47.2. HRMS (ESI): $C_{30}H_{29}NO_6$, $MH^+$, Calcd 500.20676, Found 500.20583, Diff. 1.88 ppm (FIGS. 39-41).

Example 4

Synthesis of Boc-DOPA(acetonide)-OH (23)

In this example, the inventors provide novel methods of synthesizing Boc-protected, acetonide-protected DOPA (FIG. 4).

Synthesis of Boc-DOPA(acetonide)-OH (23)

As seen in FIG. 4, TFA-DOPA(acetonide)-OMe (21) (1.75 g, 5 mmol) was subjected to alkaline hydrolysis with LiOH (0.36 g, 3 equiv) in THF/$H_2O$ (40 mL, 3:1) at 0° C. for 2.5 h. After neutralization with 1N HCl to a pH of 7-8, the mixture was added with $Na_2CO_3$ (1.06 g, 2 equiv), followed by addition of $(Boc)_2O$ (1.31 g, 1.2 equiv). The reaction was monitored by ninhydrin test and was usually completed in 5 h. The mixture was acidified with 1N HCl to a pH of 3, extracted with EtOAc, washed with water, dried over $MgSO_4$, and then concentrated under reduced pressure to afford a colorless residue, which was further purified by silica-gel flash chromatography (washed with DCM, then eluted with DCM/EtOAc/MeOH (67:30:3) to produce a white solid, 1.35 g (80%).

Spectral Data. $^1H$ NMR ($CDCl_3$): δ 10.13 (br, 1H), 6.67-6.58 (m, 3H), 6.52 (s), 4.99 (d, 1H), 4.55 (d, 1H), 3.12 (m, 1H), 2.99 (m, 1H), 1.66 (s, 6H), (1.43, 1.33) (s, 9H). $^{13}C$ NMR ($CDCl_3$): (176.8, 176.2) (1C), (156.7, 156.6) (1C), 147.8 (1C), 146.8 (1C), (129.7, 128.9) (1C), (122.4, 122.1) (1C), 118.2 (1C), 109.7 (1C), 108.4 (1C), (81.6, 80.5) (1C), (56.4, 54.6) (1C), (39.3, 37.7) (1C), (28.5, 28.2) (3C), 26.1 (2C). HRMS (ESI): $C_{17}H_{23}NO_6$, $MH^+$, Calcd. 338.15981, Found 338.15982 (FIGS. 42-45).

Example 5

Synthesis of Boc-DOPA(Chex)-OH (24)

In this example, the inventors describe novel methods of preparing Boc-protected, Chex-protected DOPA (FIG. 5).

Synthesis of Boc-DOPA(Chex)-OH (24)

As seen in FIG. 5, TFA-DOPA(Chex)-OMe (3.82 g, 10 mmol) was subjected to alkaline hydrolysis by LiOH (3 equiv) in THF/$H_2O$ (80 mL, 3:1) for 2.5 h at 0° C. After neutralization with 1N HCl to a pH of 7-8, the mixture was added with $Na_2CO_3$ (2.12 g, 2 equiv), followed by addition of $(Boc)_2O$ (1.2 equiv). The reaction was monitored by ninhydrin test and was usually completed in 3-5 h. The mixture was acidified with 1N HCl to a pH of 3, extracted with EtOAc, washed with water, dried over $MgSO_4$, and concentrated under reduced pressure to afford a colorless residue, which was further purified by silica-gel flash chromatography (washed by DCM, then eluted with DCM/EtOAc/MeOH (67:30:3) to produce a white solid, 3.36 g (89%).

Spectral Data. $^1H$ NMR ($CDCl_3$): δ ppm 10.24 (br, 1H), 6.67-6.59 (m, 3H), 6.57 (s), 5.012(d, 1H), 4.56(d, 1H), 4.36(s, 1H), 3.11-3.07 (m, H), 3.01-2.97 (m), 2.82(m, 1H), 1.89(s, 4H), 1.72(s, 4H), 1.49 (s, 2H), 1.43, 1.32(s, 9H). $^{13}C$ NMR ($CDCl_3$): δ ppm (176.79, 176.14)(1C); (156.68, 155.60)(1C); (147.83, 147.72)(1C); (146.79, 146.69)(1C); 129.47 (1C); 128.71 (1C); (122.17, 121.95)(1C); (118.90, 118.82)(1C); (109.71, 109.62)(1C); (108.33, 108.21)(1C); (81.58, 80.44)(1C); (56.35, 54.58)(1C); (39.28, 37.71)(1C); (35.45, 35.36)(1C); (28.48, 28.21) (3C); 24.72 (2C); 23.33 (1C). DEPT: CH3, (28.48, 28.21)(3C); CH2, (39.28, 37.71)(1C), (35.45, 35.36)(2C), 24.72 (2C), 23.33 (1C); CH, (122.17, 121.95) (1C), (109.71, 109.62)(1C), (08.33, 108.21)(1C), (56.35, 54.58)(1C). HRMS (ESI): $C_{20}H_{27}NO_6$, $MH^+$, Calcd. 378.19111, Found 378.19098, Diff. 0.35 ppm; $MNa^+$, Calcd. 400.17306, Found 400.17327, Diff. −0.53 ppm.

Example 6

Synthesis of TFA-DOPA(BA)-OMe (25)

In this example, the inventors describe novel methods of synthesizing BA-protected DOPA (FIG. 6).

Synthesis of TFA-DOPA(BA)-OMe (25)

As seen in FIG. 6, 12.4 g (40 mmol) of TFA-DOPA-OMe (20), benzaldehyde dimethyl acetal (24.3 mL, 160 mmol), and anhydrous benzene (350 mL) were added to a two-neck 500 ml flask. One neck of the flask was fitted with a Soxhlet extractor, the thimble of which was filled with granular anhydrous $CaCl_2$ (28 g) to trap $H_2O$ and MeOH, and the other neck of the flask was sealed with a septum for sampling purpose. After the flask was flushed with argon for 5 min and then was heated to reflux for 5 min, catalyst p-toluenesulfonic acid monohydrate (346 mg, 4.5 mol %) was added. The reaction was monitored by ferric chloride test. Once a negative test was obtained, usually 1.5 to 2 h, the reflux was stopped. After cooled down, the light yellow solution was filtered through a short silica-gel column, which was washed with DCM/EtOAc. The combined filtrate and washings were evaporated to yield a yellow oil residue, which was purified by silica-gel chromatography (washed with DCM/Hexane, and then eluted with DCM/EtOAc). After removal of the volatile, the yellow solid residue was recrystallized in DCM/hexane to afford white powders, 12.4 g (79%).

Spectral Data. $^1$H NMR (CDCl$_3$): δ ppm 7.58-7.57 (m, 2H), 7.47-7.45 (m, 3H), 6.95 (s, 1H), 6.79 (d, 1H, J=7.5 Hz), 6.60 (s, 1H), 6.57 (d, 1H, J=7.5 Hz), 4.86 (q, 1H, J=7 Hz), 3.81 (s, 3H), 3.20-3.16 (m, 1H), 3.13-3.09 (m, 1H). $^{13}$C NMR (CDCl$_3$): δ ppm 170.6, 156.74 (q, $^2J_{C-F}$=37.6 Hz), 148.3, 147.4, 136.0, 130.5, 128.9 (2C), 128.4, 126.5 (2C), 122.6, 115.84 (q, $^1J_{C-F}$=286.5 Hz), 110.6, 109.4, 108.6, 53.8, 53.1, 37.1. DEPT: CH3, 53.1; CH2, 37.1; CH, 130.4, 128.9, 126.5, 122.6, 110.6, 109.4, 108.6, 53.8. $^{19}$F NMR (CDCl$_3$): δ −76.284. HRMS (ESI): C$_{19}$H$_{16}$NO$_5$F$_3$, MH$^+$, Calcd 396.10433, Found 396.10659, Diff. 3.2 ppm.

Example 7

Acetonide-protected DOPA Methods of Use

In this example, the inventors describe various methods of using the acetonide-protected DOPA compositions of the present invention.

Fmoc-DOPA(acetonide)-OH (7) in Fmoc Solid-Phase Peptide Synthesis

To investigate the use of Fmoc-DOPA(acetonide)-OH (7) in Fmoc solid-phase peptide synthesis, a short pentapeptide, Fmoc-DOPA-Gly-Gly-Lys-Lys-OH, derived from *Phragmatopoma californica* cement proteins Pc[1] and Pc[2,3] was synthesized. The solid-phase synthesis was carried out using 2-chloro trityl chloride resin (Peptide International, USA). The first amino acid, Fmoc-Lys (Boc)-OH, was attached to the resin by the standard method. Fmoc deprotection was performed twice with 20% (v/v) piperidine in N-methyl-2-pyrrolidinone (NMP) for 15 min. Coupling reactions were performed using two equivalents of the mixture Fmoc-amino acid/BOP/HOBt/DIPEA (1:1:1:1) in NMP, with a 10 min pre-activation step before coupling. The coupling reactions were carried out for 2 h and monitored by the ninhydrin test. The Fmoc-protecting group of DOPA was not removed in order to increase the hydrophobicity of the final peptide product.

The synthesized peptide derivative was cleaved from the resin by 2% trifluoroacetic acid (TFA) in DCM to give a white powder after neutralization with pyridine/MeOH, concentration at reduced pressure, and precipitation with water. An aliquot was measured, dried, and subjected to reverse phase HPLC (RP-HPLC) and to MALDI-TOF MS. The RP-HPLC chromatogram revealed one main peak and the MALDI-TOF MS spectrum (negative mode) revealed a monoisotopic molecular weight of m/z 1028.76 (M−1), corresponding to Fmoc-DOPA(acetonide)-Gly-Gly-Lys(Boc)-Lys(Boc)-OH (calcd. 1028.50), indicating that the acetonide-protecting group was stable to 2% TFA in DCM. The above white precipitate was further cleaved by TFA/TIS/H2O (95:2.5:2.5) for 30 min at room temperature.

MALDI-TOF MS spectrum (negative mode) revealed a monoisotopic molecular weight of m/z 788.59 (M−1) (calcd. 788.36), corresponding to Fmoc-DOPA-Gly-Gly-Lys-Lys-OH, which was also confirmed by ESI/MS analysis: m/z 788.30 (negative ion, M−1), 790.40 (positive ion, M+1, calcd. 790.38). Only a single peak appeared in the RP-HPLC chromatogram, suggesting the absence of the diastereomer peptide Fmoc-D-DOPA-Gly-Gly-Lys-Lys-OH, which is expected to have a different RP-HPLC retention time.[24,25] (FIGS. 46-48).

To unambiguously determine the chirality of the synthesized Fmoc-DOPA(acetonide)-OH, it was cleaved by 25% piperidine in DCM and TFA/TIS/H2O (95:2.5:2.5) to give a raw free DOPA product, which was subjected to chiral HPLC analysis (CHIROBIOTIC T, Aldrich) using commercially available L- and D/L-DOPA as reference.[26] The absence of the D-DOPA peak in the chromatogram confirmed the optical purity of the synthesized Fmoc-DOPA(acetonide)-OH and that L-DOPA retained its chirality under the conditions of refluxing with DMP in the presence of TsOH.[27]

Through protection of the amino and carboxyl groups with phthaloyl and methyl ester, respectively, the acetonide protection of the catechol of the L-DOPA was realized in the presence of TsOH. Followed by removal of the amino and the carboxy-protecting groups, the intermediate was easily converted to the product Fmoc-DOPA(acetonide)-OH in good yield. The optical integrity of the synthesized Fmoc-DOPA (acetonide)-OH was demonstrated by chiral HPLC. As a demonstration of its use as a building block for Fmoc SPPS, the synthesized Fmoc-DOPA(acetonide)-OH was incorporated into a short synthetic peptide derivative with satisfactory purity of the peptide product.

Intermediates Into Short Peptides.

To investigate the use of the novel intermediates provided using the methods of the present invention in Fmoc solid-phase peptide synthesis, a short tetrapeptide, H-Gly-Gly-Lys (Boc)-Lys(Boc)-OH, derived from *Phragmatopoma californica* cement proteins Pc1 and Pc2, was synthesized on 2-chloro trityl chloride resin (Peptide International, USA). The fifth amino acid, DOPA, was incorporated using synthesized Fmoc-DOPA(acetonide)-OH, Fmoc-DOPA(Chex)-OH, or Boc-DOPA(Chex)-OH. After cleavage from the resin using 1% TFA in DCM, three peptide derivatives were obtained: Fmoc-DOPA(acetonide)-Gly-Gly-Lys(Boc)-Lys (Boc)-OH, Fmocc-DOPA(Chex)-Gly-Gly-Lys(Boc)-Lys (Boc)-OH, and Boc-DOPA(Chex)-Gly-Gly-Lys(Boc)-Lys (Boc)-OH. The identities of these peptide derivatives were established by MALDI-TOF MS Spectra.

Example 8

Acetonide-Protected Dopamine (14)

In this example the inventors use the novel method of the present invention to synthesize acetonide-protected dopamine-containing compounds. In general, the N-phthaloyl (Phth) protective group was introduced to dopamine by N-carbethoxyphthalimide in methanol. The resulting Phth-dopamine (8) was then refluxed and volatile byproducts were removed from the reaction system by distillation. The condensed liquid was recycled using a Soxhlet extractor, the thimble of which was filled with anhydrous CaCl$_2$ to absorb water and methanol. In addition, anhydrous solvent and argon protection were used to prevent introduction of water from external sources, shortening the reaction time to ca. 1-2 h from the 24 h sometimes required for traditional methods.[43] The raw product was subjected to GC-MS analysis, which gave a major peak in the chromatogram and a molecular ion at 323 (calcd. 323.12) in the mass spectrum, indicating that full protection of the amine group results in acetonide cyclization rather than isoquinoline formation.

The identification of Phth-dopamine(acetonide) (9) was further confirmed by high resolution mass spectrometry (HRMS) and nuclear magnetic resonance (NMR) spectroscopy, with the latter showing a peak at δ ppm 117.8 for the quaternary carbon of the acetonide group. The introduction of a carbonyl group adjacent to the nitrogen atom followed by protonation of the amide nitrogen may form an N-acyliminium ion, which probably facilitates Pictet-Spengler type reactions due to increased eletrophilic reactivity.[39] However, acetonide cyclization may still be favored if the reaction is carried out in an aprotic solvent with only catalytic amount of acids.

Synthesis of Phth-dopamine (8)

As seen in FIG. 7, N-carbethoxyphthalimide (11.0 g, 50 mmol), methanol (300 mL), dopamine hydrochloride (9.0 g, 50 mmol), and a magnetic stirring bar were added to a 500 mL flask. The mixture was degassed with argon for 30 min, followed by addition of triethylamine (28 mL, 200 mmol). The mixture was stirred at room temperature overnight. After the volatile solvents were reduced by rotary evaporation, the residue was treated with 1N HCl and the mixture was extracted with ethyl acetate. The organic layer was washed with 1N HCl and water, dried over $MgSO_4$, and evaporated to give a yellow solid, which was recrystallized in EtOAc/hexane to give pale yellow crystals, 10.5 g (74%).

Spectral Data. $^1$NMR (DMSO-$d_6$): δ ppm 8.81, 8.71 (catecholic protons), 7.81 (m, 4H), 6.59 (m, 2H), 6.39 (m, 1H), 3.71 (t, 2H, J=7.4 Hz), 3.45 (water), 2.72 (t, 2H, J=7.4 Hz). $^{13}$C NMR (DMSO-$d_6$): 167.6 (2C), 145.1, 143.7, 134.3 (2C), 131.4 (2C), 128.9, 122.9 (2C), 119.2, 115.9, 115.5, 39.2, 33.1. LC-MS (ESI), $C_{16}H_{13}NO_4$, MNa$^+$, Calcd. 306.07, Found 306.10; (M–H)$^-$, Calcd. 282.08, Found 282.10 (FIGS. 49-50).

Synthesis of Phth-dopamine(acetonide) (9)

As seen in FIG. 7, Phth-dopamine (8) (5 g, 20 mmol), DMP (8.9 mL, 4 equiv), and anhydrous benzene (200 mL) were added to a two-neck 250 mL flask. One neck of the flask was fitted with a Soxhlet extractor, the thimble of which was filled with 28 g of granular anhydrous $CaCl_2$; the other neck of the flask was sealed with a septum for sampling purpose. After the system was degassed with argon for 5 min and then heated to reflux for another 5 min, p-toluenesulfonic acid monohydrate (134 mg, 4.0 mol %) was added. The reaction progress was monitored by $FeCl_3$ test. Once a negative test result was achieved, usually in 1-2 h, the reflux was stopped. After cooling, the mixture was filtered through a short silica-gel column, which was washed with DCM. The combined filtrate and washings were evaporated to produce a light yellow solid, which was recrystallized in DCM/hexane to give white crystals, 5.4 g (95%).

Spectral Data. $^1$H NMR (CDCl$_3$): δ ppm 7.82 (m, 2H), 7.70 (m, 2H), 6.65-6.61 (m, 3H), 3.86 (t, 2H, J=7.8 Hz), 2.87 (t, 2H, J=7.8 Hz), 1.64 (s, 6H). $^{13}$C NMR (CDCl$_3$): 168.3(2C), 147.7, 146.2, 133.9 (2C), 132.1 (2C), 131.2, 123.3 (2C), 121.2, 117.8, 109.1, 108.2, 39.7, 34.5, 25.9 (2C). HRMS: $C_{19}H_{17}NO_4$, MH$^+$, Calcd. 324.12303, Found 324.12272 (FIGS. 51-53).

Synthesis of Fmoc-dopamine(acetonide) (10)

As seen in FIG. 7, Fmoc-dopamine, synthesized according to literature,[28] was converted to Fmoc-dopamine(acetonide) using the above method. Fmoc-dopamine (5 g) was refluxed with DMP (6.7 mL) in the presence of p-toluenesulfonic acid monohydrate (101 mg) in anhydrous benzene for 45 min. The solid residue was recrystallized in EtOAc/hexane to give a white powder, 4.97 g (90%).

Spectral Data. $^1$H NMR (CDCl$_3$): δ ppm 7.79 (d, 2H), 7.60 (d, 2H), 7.42 (t, 2H), 7.34 (t, 2H), 6.69-6.58 (m, 3H), 4.86 (br, 1H), 4.43 (d, 2H), 4.24 (t, 1H), 3.42 (q, 1H), 2.73 (t, 1H), 1.69 (s, 6H). $^{13}$C NMR (CDCl$_3$): 156.5, 147.8 (2C), 146.2, 144.1 (2C), 141.5, 131.9, 127.8 (2C), 127.2 (2C), 125.2 (2C), 121.3, 120.2 (2C), 118.0, 109.1, 108.3, 66.7, 47.5, 42.6, 36.0, 26.1 (2C). DEPT: CH3, 26.1; CH2, 66.7, 42.6, 36.0; CH, 127.8, 127.2, 125.2, 121.3, 120.2, 109.1, 108.3. HRMS (ESI): $C_{26}H_{25}NO_4$, MH$^+$, Calcd. 416.18563, Found 416.18493 (FIGS. 54-55).

Reaction of Boc-dopamine and DMP

Boc-dopamine was synthesized according to literature.[10] To a two-neck 250 mL flask were added Boc-dopamine (6.3 g, 25 mmol), DMP (12.5 mL, 4 equiv), and anhydrous benzene (200 mL). One neck of the flask was fitted with a Soxhlet extractor, the thimble of which was filled with 28 g of granular anhydrous $CaCl_2$. The other neck of the flask was sealed with a septum for sampling purpose. After the system was degassed with argon for 5 min and then heated to reflux for another 5 min, p-toluenesulfonic acid monohydrate (210 mg, 4.5 mol %) was added. The reaction was monitored by $FeCl_3$ test. After 4 h, an aliquot was sampled and subjected to $FeCl_3$ test, which showed a dark black spot on the TLC plate. A second portion of p-toluenesulfonic acid monohydrate (4.8 g, 25 mmol) was added. One hour later, the mixture was cooled to room temperature and filtered though a fritted glass filter. A light yellow solid was collected, ca. 7 g. A portion of the solid (2 g) was dissolved in water, washed with DCM and azeotropically evaporated with toluene under reduced pressure. After addition of acetonide followed by toluene, a white precipitate was collected, dried under vacuum, (260 mg, ca. 10%), and characterized by NMR, LC-MS, and HRMS. The resultant 6,7-dihydroxy-1,1-dimethyl-1,2,3,4-tetrahydro-isoquinolinium 4-methylbenzenesulfonate is abbreviated as TsOH-DTTQ.

Spectral Data (TsOH-DDTQ). $^1$H NMR (DMSO-$d_6$): δ ppm 7.50 (m, 2H), 7.13 (m, 2H), 6.69(s, 1H), 6.50 (s, 1H), 3.33(s, 2H), 2.81 (t, 2H), 2.29 (s, 3H), 1.54(s, 6H). $^1$H NMR (DMSO-$d_6$)-COSY: 7.50 correlates with 7.13; 3.33 correlates with 2.81. $^{13}$C NMR (DMSO-$d_6$): 144.874, 144.834, 144.5, 138.1, 128.5, 128.2 (2C), 125.4 (2C), 120.9, 114.9, 112.0, 56.1, 36.8, 27.7, 24.5, 20.8 (2C). DEPT: CH3, 27.7, 20.8; CH2, 36.8, 24.5; CH 128.2, 125.4, 114.9, 112.0. LC-ESI: $C_7H_8SO_3$ (M–H)$^-$, Calcd. 171.01, Found 171.00; $C_{11}H_{16}NO_2$, MH$^+$, Calcd. 194.12, Found 194.10. HRMS: $C_7H_8SO_3$ (M–H)$^-$ Calcd. 171.01214, Found 171.01258; $C_{11}H_{16}NO_2$, MH$^+$, Calcd. 194.11756, Found 194.11715 (FIGS. 56-66).

Synthesis of TEA-dopamine (12)

As seen in FIG. 7, dopamine hydrochloride (21.3 g, 112.3 mmol), methanol (250 mL), and a magnetic stirring bar were added to a 500 mL flask. The mixture was degassed with argon for 30 min, followed by addition of methyl trifluoroacetate (23 mL, 230 mmol) and triethylamine (64 mL). The mixture was stirred at room temperature overnight. The volatile solvents were removed by rotary evaporation and the residue was treated with 1 N HCl to a pH of ca. 1 and extracted by ethyl acetate. The organic layer was washed with water, dried over $MgSO_4$, and evaporated to give a white solid, 27.7 g (98%).

Spectral Data. $^1$H NMR (DMSO-$d_6$): δ ppm 9.47, 8.76, 8.68 (catecholic and amide protons) 6.64 (d, 1H, J=4 Hz), 6.58 (d, 1H, J=1 Hz), 6.50 (dd, 1H, J=4 Hz, J=1 Hz), 3.39 (water), 3.32 (q, 2H, J=7.5 Hz), 2.61 (t, 2H, J=7.5 Hz). $^{13}$C NMR (DMSO-d$_6$): 156.13 (q, $^2J_{C-F}$=35.3 Hz), 145.1, 143.7, 139.4, 119.3, 116.0, 115.97 (q, $^1J_{C-F}$=287 Hz), 115.5, 41.0, 33.6 (FIGS. 67-68).

Synthesis of TFA-dopamine(acetonide) (13)

As seen in FIG. 7, TFA-dopamine (12) (5 g, 20 mmol), DMP (10 mL, 4 equiv), and anhydrous benzene (200 mL) were added to a two-neck 250 mL flask. One neck of the flask was fitted with a Soxhlet extractor, the thimble of which was filled with 28 g of granular anhydrous CaCl$_2$; the other neck of the flask was sealed with a septum for sampling purpose. After the system was degassed with argon for 5 min and then heated to reflux for another 5 min, p-toluenesulfonic acid monohydrate (172 mg, 4.5 mol %) was added. The reaction progress was monitored by FeCl$_3$ test. Once a negative test result was achieved, usually in 1-2 h, the reflux was stopped. After cooled down, the mixture was filtered through a short silica-gel column, which was washed with DCM. The combined filtrate and washings were evaporated to produce a light yellow solid, which was recrystallized in DCM/hexane to give white crystals, 4.7 g (89%).

Spectral Data. $^1$H NMR (CDCl$_3$): δ ppm 6.67 (d, 1H), 6.59-6.57 (m, 2H), 6.50 (br, 1H), 3.56 (q, 2H), 2.78 (t, 2H), 1.67 (s, 6H). $^{13}$C NMR (CDCl$_3$): 157.36 (q, $^2J_{C-F}$=36.6 Hz), 148.1, 146.6, 130.7, 121.2, 118.2, 115.99 (q, $^1J_{C-F}$=286 Hz), 108.8, 108.5, 41.4, 34.9, 26.0 (2C). $^{19}$F NMR (CDCl$_3$): δ −76.438. DEPT: CH3, 26; CH2, 41.4, 34.9; CH, 121.2, 108.8, 108.5. HRMS (ESI): C$_{13}$H$_{14}$NO$_3$F$_3$, MH$^+$, Calcd. 290.09985, Found 290.10030. Anal. for C$_{13}$H$_{14}$NO$_3$F$_3$: Calcd C, 53.98; H, 4.88; N, 4.84; Found C, 53.95; H, 4.88; N, 4.79 (FIGS. 69-71).

Synthesis of Dopamine(acetonide) (14)

Method A. To a 250 mL flask were added Phth-dopamine (acetonide) (9) (1.62 g,), methanol (50 mL), DCM (50 mL), and hydrazine hydrate (2.5 mL, 10 equiv). The mixture was stirred at room temperature for 3 days. The white precipitate was removed by filtration and washed with DCM. The combined filtrate was concentrated under reduced pressure. After addition of another portion of DCM (50 mL), the mixture was stirred for another day. White precipitates were filtered off and the combined precipitate was dried and measured (ca. 0.85 g). The filtrate was concentrated and dried under vacuum to produce a light yellow oil, 0.93 g (97%).

Method B. To a 100 mL flask were added TFA-dopamine (acetonide) (13) (1.5 g, 5.2 mmol) and THF (30 mL), followed by addition of lithium hydroxide (0.25 g, 10.3 mmol) in 10 mL water. The mixture was stirred at room temperature for 4 h. After the organic solvents were reduced by rotary evaporation, the mixture was treated carefully with 1N HCl to a pH of 2-3, washed with DCM, adjusted to a pH of 8 with NaHCO$_3$, and extracted with EtOAc. The organic layer was washed with water, dried over MgSO4, and evaporated to give a light yellow oil, 0.87 g (87%).

Spectral Data. $^1$H NMR (CDCl$_3$): δ ppm 6.66-6.59 (m, 3H), 2.92 (t, 2H), 2.66 (t, 2H), 1.91 (br, 2H), 1.67 (s, 6H). $^{13}$C NMR (CDCl$_3$): 147.6, 145.9, 132.1, 121.1, 117.6, 108.9, 108.0, 42.8, 38.0, 25.8 (2C). DEPT: CH3, 25.8; CH2, 42.8, 38.0; CH, 121.1, 108.9, 108.0. GC-MS: m/z 193 (17%), 164 (80.6%), 163 (32.4%), 149 (100%), 124 (18.1%), 123 (75%), 121 (18.1%), 106 (23.6%). HRMS (ESI): C$_{11}$H$_{15}$NO$_2$, MH$^+$, Calcd 194.11756, Found 194.11757 (FIGS. 72-75).

Synthesis of DHA-dopamine(acetonide) (15)

As illustrated in FIG. 8, DHA-dopamine(acetonide) (15) is synthesized by drying 1 g 4Z,7Z,10Z,13Z,16Z,19Z-docosa-4,7,10,13,16,19-hexaenoic acid in 4 mL ethanol was with toluene by rotary evaporation. The oil residue was dissolved in 20 mL degassed dry toluene/chloroform (1:1). After addition of N-hydroxysuccinimide (0.57 g) and 1,3-dicyclohexylcarbodiimide (0.62 g), the mixture was stirred under argon protection for 5 h. The precipitate was removed by filtration and the filtrate was stirred with dopamine(acetonide) (0.58 g) under argon for 2 days. The volatile solvents were removed under vacuum and the residue was purified by silica-gel flash chromatography (chloroform/ethyl acetate, 5:1) to give a light yellow oil, 1.05 g (68%).

Spectral Data. $^1$H NMR (500 MHz, CDCl$_3$): δ ppm 6.65-6.56 (m, 3H), 5.37-5.32 (m, 12H), 3.44 (q, 2H, J=6.5 Hz), 2.84-2.81(m, 10H), 2.69 (t, 2H, J=6.4 Hz), 2.38 (q, 2H, J=7 Hz), 2.18 (t, 2H, J=7.5 Hz). 2.07 (m, 2H, J=7 Hz). 1.65 (s, 6H), 0.97 (t, 3H, J=7 Hz). $^{13}$C NMR (125 MHz, CDCl$_3$): δ 172.4, 147.8, 146.2, 132.15, 132.06, 129.4, 128.7, 128.40 (m,) 128.23, 128.20, 127.99, 127.1, 121.1, 117.9, 108.9, 108.2, 40.9, 36.6, 35.6, 25.98, 25.76 (m, 5C), 23.5, 20.7, 14.4. $^{13}$C NMR (125 MHz, CDCl$_3$) DEPT: CH3, 25.98, 14.4; CH2, 40.9, 36.6, 35.6, 25.76 (m, 5C), 23.5, 20.7; CH, 132.15, 129.4, 128.7, 128.40 (m, 5C) 128.23, 128.20, 127.99, 127.1, 121.1, 108.9, 108.2. LC-ESI: MH$^+$, Calcd. 504.35, Found 504.30; (2M+H)$^+$, Calcd. 1007.69, Found 1007.60. HRMS: C$_{33}$H$_{45}$NO$_3$, MH$^+$, Calcd. 504.34722, Found 504.34608 (FIGS. 76-80).

Synthesis of DHA-dopamine (16)

As illustrated in FIG. 8, DHA-dopamine (16) is synthesized by adding 7.4 mL degassed chloroform, 2.5 mL TFA, and 0.1 mL water to a 50 ml flask sealed with a septum. After the flask was flushed with argon for 2 min, DHA-dopamine (acetonide) (200 mg) was added with a syringe. The mixture was stirred for 3 h at room temperature. The volatile solvents were removed under vacuum and a light brown residue was obtained, which was re-dissolved in ethanol and stored in freezer, yield 100%.

Spectral Data. $^1$H NMR (500 MHz, CDCl$_3$): δ ppm 6.79-6.52 (m, 3H), 5.99 (s, catecholic proton), 5.40-5.28 (m, 12H), 3.42 (m, 2H), 2.95-2.78(m, 10H), 2.64 (t, 2H, J=6.8 Hz), 2.36 (q, 2H, J=6.8 Hz), 2.21 (t, 2H, J=6.8 Hz). 2.06 (m, 2H, J=7.3 Hz). 0.96 (t, 3H, J=7.3 Hz). $^{13}$C NMR (125 MHz, CDCl$_3$): δ 174.2, 144.1, 142.8, 131.8, 130.1, 129.6, 128.3, 128.18, 128.10 (2C), 127.77 (2C), 127.59, 127.54, 127.17, 126.7, 120.3, 115.3, 115.2, 41.2, 36.3, 34.7, 25.6 (4C), 25.5, 23.4, 20.6, 14.3. $^{13}$C NMR (125 MHz, CDCl$_3$) DEPT: CH3, 14.3; CH2, 41.2, 36.3, 34.7, 25.6 (4C), 25.5, 23.4, 20.6; CH, 131.8, 130.1, 128.3, 128.18, 128.10, 127.77, 127.59, 127.54, 127.17, 126.7, 120.3, 115.3, 115.2. LC-MS: MH$^+$, Calcd. 464.31. Found 464.30; (2M+H)$^+$, Calcd. 927.63, Found 927.60. HRMS: C$_{30}$H$_{41}$NO$_3$, MH$^+$, Calcd. 464.31592, Found 464.31560 (FIGS. 81-85).

Synthesis of MA-dopamine(acetonide) (17)

As illustrated in FIG. 9, MA-dopamine(acetonide) (17) is synthesized by adding dopamine(acetonide) (0.75 g, 3.88 mmol), DCM (35 mL), DIPEA (2.7 mL, 4 equiv) and methacrylate anhydride (1.25 mL, 2 equiv) to a 100 ml flask. The mixture was stirred for 2-4 h at room temperature. The reaction was monitored by ninhydrin test. The mixture solution was treated with 1M citric acid solution, extracted with DCM, washed by water, dried over MgSO$_4$, and concentrated to give an oil residue, which was further purified by silica-gel chromatography (washed by DCM and then eluted by DCM/EtOAc (3:1) to give a light yellow oil, 0.95 g (93%).

Spectral Data. $^1$H NMR (CDCl$_3$): δ 6.59-6.52 (m, 3H), 6.35 (br, 1H), 5.59 (s, 1H), 5.23 (s, 1H), 3.43 (q, 2H, J=6.7 Hz), 2.69 (t, J=6.7 Hz) 1.87 (s, 3H), 1.59 (s, 6H). $^{13}$C NMR (CDCl$_3$): 168.5, 147.6, 146.0, 140.0, 132.0, 120.9, 119.4, 117.7, 108.8, 108.0, 41.1, 35.3, 25.8, 18.608, 18.599. DEPT: CH3, 26.1, 18.608, 18.599; CH2, 119.4, 41.4, 35.6; CH, 120.9, 108.8, 108.0. GC-MS: m/z 262 (1.7%), 261 (10.9%), 177 (12.5%), 176 (100%), 163 (21.6%), 162 (8.8%), 161 (79.8%), 136 (10%), 123 (28.9%). HRMS (ESI): C$_{15}$H$_{19}$NO$_3$, MH$^+$, Calcd. 262.14377, Found 262.14432 (FIGS. 86-88).

Analysis. $^1$H and $^{13}$C NMR spectra were collected on a Varian Inova (500 MHz) spectrometer using TMS or the deuterated solvent residue as the internal standard. $^{19}$F NMR spectra were collected on a Varian Mercury (400 MHz) spectrometer using CFCl$_3$ as an external standard. GC-MS analysis was performed on Hewlett Packard 6890 GC/MSD instrument using capillary column and electron impact (EI) ionization. LC-MS analysis was performed on Agilent MSD1100 instrument using methanol or combinatory solvents as eluant.

Results and Discussion. Fmoc- and Boc-protected dopamine behaved quite differently when refluxed with DMP and TsOH. Fmoc-dopamine, synthesized by reacting dopamine with fluorenylmethyloxycarbonyl chloride,[41] readily underwent acetonide cyclization to form Fmoc-dopamine(acetonide) (10).

The course of the reaction was conveniently monitored by the ferric chloride (FeCl$_3$) test on a TLC plate, which produces a black spot for free catechols at room temperature. After acetonide protection, the spot was indistinguishable from yellow background, but turned black after heating to 105° C.

In the case of Boc-dopamine,[42] even after a 4 h reflux with 5.5% TsOH and DMP, ferric chloride test still produced a dark black dot on the TLC plate, indicating the presence of a significant amount of unprotected catechol. A second portion of TsOH (1 equiv) was added and the reaction mixture was stirred for another 1 h to give a precipitate, which was collected, purified, and subjected to intensive characterization. Positive mode LC-MS data revealed a monoisotopic molecular ion of m/z 194.10, corresponding to C$_{11}$H$_{16}$NO$_2$ (MH$^+$), suggesting the addition of a C$_2$H$_6$C group to dopamine. Negative mode LC-MS data showed a peak at 171.00, indicating the presence of p-toluenesulfonate anions ((M−H)$^-$, Calcd. 171.01). In addition with the HRMS and NMR data, the product was identified as a sulfonic salt of a tetrahydroisoquinoline (11). The result is not entirely unexpected because the acid-labile Boc protective group is readily removed when heated in the presence of TsOH, releasing dopamine that subsequently undergoes a Pictet-Spengler condensation.[45]

In contrast with the Boc protective group, TFA is stable to acids, and it is smaller in size than the Fmoc group. TFA-dopamine (12) was isolated in low yield (19%) from the Bischler-Napieralski reaction of TFA and methyl ether protected dopamine in the presence of BBr$_3$.[46]

An improved procedure was developed by treating dopamine hydrochloride with methyl trifluoroacetate in methanol in the presence of triethylamine, giving an almost quantitative yield. The acetonide protection of TFA-dopamine (12) ran smoothly and was completed in 1.5 h with a yield of ca. 89%. It is necessary to stop the reaction once it is completed, as prolonged refluxing time will result in a reduced yield. Overnight refluxing reduced the yields for both the acetonide product of TFA- and Phth-dopamine, however the TFA-product was reduced significantly more than the Phth-product. This suggests that the partial protection by TFA was less stable than the full protection by phthalimide. The advantage of using the TFA protective group is that alkaline hydrolysis of TFA and methyl ester protective groups can be accomplished in one step, which may facilitate the synthesis of Fmoc-DOPA(acetonide)-OH (7).

The free amino form of acetonide-protected dopamine (14) was obtained either by deprotection of the phthaloyl group of Phth-dopamine (acetonide) (9) with hydrazine in DCM or by hydrolysis of TFA-dopamine(acetonide) (13) in lithium hydroxide solution. Dopamine (acetonide) (14) is a light yellow oil with a $^{13}$C NMR signal at δ ppm 117. 6 from the quaternary acetonide carbon.

Example 9

Acetonide-protected Dopamine Methods of Use

To demonstrate the utility of dopamine (acetonide), DHA-dopamine (16) was synthesized (FIG. 8). Commercially available DHA was activated with dicyclohexylcarbodiimide (DCC) and converted to an N-hydroxysuccinimide (NHS) ester, which was then stirred with dopamine(acetonide) in toluene and chloroform. Since the catechol is protected, the resulting DHA-dopamine(acetonide) (15) was readily purified by flash chromatography (hexane/EtOAc) to give a light yellow oil. The molecular formula of this intermediate was established by HRMS: C$_{33}$H$_{45}$NO$_3$, MH$^+$, Calcd 504.34722, Found 504.34608. Acetonide-protected dopamine (14) was subjected to deprotection in chloroform solution with 25% trifluoroacetic acid to quantitatively produce DHA-dopamine (16, 100%), which gave the correct mass (HRMS): MH$^+$, Calcd. 464.31592, Found 464.31560, and acetone as a byproduct, which can be easily removed by evaporation.

Dopamine(acetonide) (14) could also be utilized for the synthesis of catechol-containing monomers. A high concentration of unprotected catechols retards free radical polymerizations, due to degradative chain transfer with the polymer radicals.[47] Therefore, catechol-containing copolymers are generally synthesized in a protected form followed by removal of the catechol protecting group.[48] Methyl methacrylate is used for the production of poly(methyl methacrylate) acrylic plastics and methyl methacrylate-butadiene-styrene resin. A combination of these two moieties was realized by reacting dopamine(acetonide) with methacrylate anhydride in the presence of diisopropylethylamine (DIPEA) to give N-(2-(2,2-dimethylbenzo[1,3]dioxol-5-yl)ethyl)methacrylamide (FIG. 9, 17). N-(2-(2,2-dimethylbenzo[1,3]dioxol-5-yl) ethyl)methacrylamide may be polymerized individually or copolymerized with such monomers as styrene, followed by deprotection, to produce catechol containing polymers.

Example 10

Chex-Protected DHCA

In this example, the inventors provide novel methods of synthesizing Chex-protected DHCA (FIG. 10).

Synthesis of DHCA-OMe (26)

As shown in FIG. 10, step a, DHCA (18.2 g, 100 mmol), methanol (250 mL), and a magnetic stirring bar were added to a 500 ml flask. The flask was cooled in an acetonitrile/dry ice bath. Thionyl chloride (14.6 mL, 200 mmol) was added. After stirring for 30 min, the cooling bath was removed and the mixture was stirred overnight at room temperature. The volatile materials were removed by rotary evaporation and the resulting yellow residue was dried under vacuum to yield a brown oil, which solidified several days later to produce a dark brown solid (100%).

Synthesis of DHCA(Chex)-Ome (27)

As shown in FIG. 10, step b, DHCA-OMe (26) (9.8 g, 50 mmol) was refluxed with DMCH (30 mL, 4 equiv) in anhydrous benzene (ca. 180 mL) in the presence of p-toluenesulfonic acid monohydrate (475 mg, 5 mol %). After filtered through a short silica-gel column, the yellow solution was concentrated under reduce pressure to afford an oil residue, which was further purified by silica-gel flash chromatography (washed by DCM/Hexane, then eluted with DCM/EtOAc) to yeild a colorless oil, 12.6 g (91%).

Spectral Data. $^1$H NMR (CDCl$_3$): δ 6.65-6.58 (m, 3H), 3.68 (s, 3H), 2.85 (t, 2H, J=4 Hz), 2.59 (t, 2H, J=4 Hz), 1.89 (t, 4H, J=4.5 Hz), 1.73 (m, 4H), 1.50 (m, 2H). $^{13}$C NMR (CDCl$_3$): δ 173.6, 147.7, 146.1, 133.6, 120.4, 118.6, 108.7, 108.2, 51.8, 36.3, 35.4 (2C), 30.9, 24.8, 23.3 (2C) (FIGS. 89-90).

Synthesis of DHCA(Chex)-OH (28)

As shown in FIG. 10, step c, DHCA(Chex)-OMe (27) (5.32, 1.93 mmol), THF (60 mL), and lithium hydroxide (0.93 g, 2 equiv) solution (20 mL) were added to a 250 ml flask. The mixture was stirred for 6 h at room temperaturre. The mixture was concentrated under reduced pressure, treated with 1M citric acid to a pH of 5, extracted with EtOAc, washed with water, dried over MgSO$_4$, and concentrated again under reduced presure. The resulting solid was recrystalized in DCM/Hexane to afford white crystals, 4.4 g (88%).

Spectral Data. $^1$H NMR (CDCl$_3$): δ 10.47 (br, 1H), 6.67-6.60 (m, 3H), 2.87 (t, 3H, J=7 Hz), 2.66 (t, 3H, J=7 Hz), 1.91 (t, 4H, J=6 Hz), 1.74 (m, 4H), 1.51 (m, 2H). $^{13}$C NMR (CDCl$_3$): δ 179.5, 147.7, 146.1, 133.3, 120.5, 118.7, 108.7, 108.2, 36.2, 35.3 (2C), 30.6, 24.7, 23.4 (2C). HRMS (ESI): C$_{15}$H$_{18}$O$_4$, MH$^+$, Calcd 263.12779, Found 263.12743 (FIGS. 91-92).

Synthesis of DHCA(Chex)-OSu (29)

As shown in FIG. 10, step d, DHCA(Chex)-OH (28) (5.2 g, 20 mmol), HOSu (2.5 g, 1.2 equiv), DCM (150 mL), and a magnetic stirring bar were added to a 250 ml flask. After all solids were dissolved, DCC (2.06 g, 1 equiv) was added. The flask was sealed with a septum and the mixture was stirred for 3-5 h at room temperature. The flask was stored in refrigerator overnight. The white precipitate was filtered off and the filtrate, which contains DHCA(Chex)-OSu (29) and can be used directly to couple with amines, was concentrated by rotary evaporation, followed by recrystallization in DCM/IPA to yield a white solid, 5.8 g (81%).

Spectral Data. $^1$H NMR (CDCl$_3$): δ 6.67-6.62 (m, 3H), 2.97-2.93 (m, 2H), 2.88-2.83 (m, 6H), 1.90 (t, 4H, J=5.5 Hz), 1.73 (m, 4H), 1.50 (m, 2H). $^{13}$C NMR (CDCl$_3$): δ 169.3 (2C), 168.1, 147.9, 146.4, 132.2, 120.6, 118.9, 108.7, 108.3, 35.4 (2C), 33.3, 30.5, 25.8 (2C), 24.8, 23.4 (2C). HRMS (ESI): C$_{19}$H$_{21}$NO$_6$, MH$^+$, Calcd. 360.14416, Found 360.14400, Diff. 0.45 ppm; MNa$^+$, Calcd. 382.12611, Found 382.12739 (FIGS. 93-94).

Example 11

Acetonide-Protected DHCA

In this example the inventors provide a novel method of synthesizing acetonide-protected 3-(3,4-Dihydroxyphenyl) propionic acid, also known as dihydrocaffeic acid (DHCA) (FIG. 11).

Synthesis of DHCA(acetonide)-OSu (31)

The synthesis started with DHCA-OMe (26) (9.8 g, 50 mmol), which as refluxed with DMP (25 mL, 4 equiv) in benzene in the presence of TsOH. The obtained oil residue was purified by silica-gel flash chromatography to yield DHCA(acetonide)-OMe (31), a colorless oil, 10.2 g (86%). The resulting oil was subject to alkaline hydrolysis with LiOH in THF/water, followed by recrystallization in DCM/Hexane to afford DHCA(acetonide)-OH (30), white crystals, 83%. DHCA(acetonide)-OH (30) (4.4 g) was further reacted with DCC/HOSu (4.12 g/2.5 g) in DCM to produce DHCA (acetonide)-Osu, which was recystalized in DCM/IPA to yield a white solid, 4.87 g (76%).

Spectral Data for DHCA(acetonide)-OH (30). $^1$H NMR (DMSO-d$_6$): δ 12.12 (br, 1H), 6.71-6.61 (m, 3H), 2.72 (t, 2H, J=6.5 Hz), 2.48 (t, 2H, J=6.5 Hz), 1.60 (s, 6H). $^{13}$C NMR (DMSO-d$_6$): δ 173.9, 146.8, 145.1, 134.1, 120.5, 117.5, 108.5, 107.8, 35.7, 30.2, 25.6 (2C). HRMS (ESI): C$_{12}$H$_{15}$O$_4$, MH$^+$, Calcd. 223.09649, Found 223.09631.

Spectral Data for DHCA(acetonide)-NHS. $^1$H NMR (CDCl$_3$): δ 6.66-6.62 (m, 3H), 2.97-2.93 (m, 2H), 2.88-2.81 (m, 6H), 1.66 (s, 6H). $^{13}$C NMR (CDCl$_3$): δ 169.3 (2C), 168.1, 147.8, 146.3, 132.4, 120.8, 117.9, 108.7, 108.2, 33.2, 30.4, 26.0 (2C), 25.8 (2C). GC-MS: m/z 263 (7.5%), 262 (45.2%), 220 (13.7%), 219 (100%), 203 (8.5%), 81 (12.3%). HRMS (ESI): C$_{16}$H$_{17}$NO$_6$, MH$^+$, Calcd. 320.11286, Found 320.11198, Diff. 2.76 ppm

Example 12

Methods and Materials

Ferric Chloride Test. As seen in FIG. 12, the analyte in solution was introduced onto a TLC plate by a glass capillary (1 µL). After drying, the TLC plate was briefly dipped in 1% ferric chloride ethanol solution. A positive result is indicated by a black spot, whereas a negative result is indicated by the yellow-brown color of ferric chloride. For tests performed at high temperature, the ferric chloride soaked TLC plate was put in an oven (105° C.) for 10 min. The analytes were loaded on TLC plates. The plates were dipped into ferric chloride solution for 1 sec at room temperature. Plate 2 was then heated at 105° C. for 10 min.

Reverse Phase High Performance Liquid Chromatography (RP-HPLC).

The analysis was performed on a Vydac C18 reversed-phase column with a linear gradient of 2% CH$_3$CN in 0.1% TFA (Solvent A) and 90% CH$_3$CN in 0.1% TFA (Solvent B). UV detection was performed at both 215 nm and 280 nm (FIGS. 13-16).

Chiral High Performance Liquid Chromatography (Chiral HPLC).

The synthesized Fmoc-DOPA(acetonide)-OH (50 mg) was cleaved by 25% piperidine in DCM, dried under vacuum, and then cleaved by TFA/TIS/H$_2$O (95:2.5:2.5), dried under vacuum. The obtained solid was taken by water, filtered, and subjected to chiral HPLC analysis. Commercially available L-DOPA and D/L-DOPA (Aldrich) were used as reference. The analysis was performed on a CHIROBIOTIC T (25 cm×4.6 mm, Aldrich) chiral column, eluted by MeOH/H$_2$O (6:4) at a flow rate of 0.5 mL/min.[4] UV detection was performed at both 215 nm and 280 nm (FIGS. 17-19).

Rate of Acetonide Deprotection.

Acetonide deprotection was performed using various concentrations of trifluoroacetic acid in deuterated solvents in capped NMR tubes. TFA-dopamine(acetonide) was selected as a model. The deprotection process was monitored by NMR array experiments at 22.5° C. The intensities of the methyl groups of the acetonide were used to quantitatively measure the remaining amounts of acetonide protected-dopamine. The data were fitted with first order decay model (FIG. 20A-B).

TABLE 2

Solvents: 2.5% TIS and 2.5% $H_2O$ in DMSO-$d_6$.

| Trifluoroacetic Acid | Acetonide Half Life |
|---|---|
| 80% | complete in 1.5 min |
| 75% | 60 sec |
| 70% | 20.4 min |
| 60% | 361 min |
| 50% | >14 days |

TABLE 3

Solvents: 2.5% TIS and 0.6% $H_2O$ in $CDCl_3$.

| Trifluoroacetic Acid | Acetonide Half Life |
|---|---|
| 20% | 5.8 min |
| 10% | 14.3 min |

Example 13

Comparative Example

Soloshonok v. Okumura Methods

The complexity of synthesizing acetonide-protected catechol-containing compounds can be seen by comparing methods known to the art as attempting to synthesize the protected products of the present invention. For instance, Soloshonok et al. (*Synthesis* (2008, p693-695)) reported that by protecting the amino group of DOPA through protonation of the amino group with hydrochloride and the carboxyl group as a methyl ester, acetonide-protected DOPA was efficiently synthesized. According to the early literature, a similar strategy was taken by Okumura et al.,[17] who described the synthesis of methyl 6,7-dihydroxy-1,2,3,4-tetrahydroisoquinoline-3-carboxylate by cyclization of the hydrochloride salt of DOPA methyl ester with 2,2-dimethoxypropane in the presence of TsOH. In Okumura, the product is a result of a Pictet-Spengler reaction, not the acetonide-protected DOPA as claimed by Soloshonok. Several other reports on the Pictet-Spengler reactions of phenylanaline-like amino acids also indicated the formation of the isoquinoline products.[49-53]

In view of the apparent discrepancy between previous reports and the recent account by Soloshonok, we revisited this strategy by following the method reported by Soloshonok and comprehensively characterized the obtained product. Specifically, we carried out one of the reactions, entry 2 in Table 2, of the Soloshonok reference.

Synthesis of hydrochloride Salt of (S)-methyl 6,7-dihydroxy-1,1-dimethyl-1,2,3,4-tetrahydroisoquinoline-3-carboxylate To a 500 flask were added L-DOPA (19.7 g, 100 mmol), methanol (250 mL), and a magnetic stirring bar. The flask was cooled in an acetonitrile/dry ice bath, after which thionyl chloride (14.6 mL, 200 mmol) was added. After stirring for 30 min, the bath was removed and the mixture was stirred overnight at room temperature. The volatile materials were removed by rotary evaporation and the resulting yellow residue was dried under high vacuum to yield a light yellow solid, which was not purified and used directly in the next step.

To a two-necked 250 mL flask were added the above methyl ester (6.2 g, 25 mmol), acetone (100 mL), and isopropyl alcohol (100 mL). One neck of the flask was fitted with a Dean-Stark apparatus and the other neck was sealed with a septum for sampling. After the system was flushed with argon for 5 min and then heated to reflux for another 5 min, catalyst TsOH (0.475 g, 2.5 mmol) was added. A white precipitate appeared after 3 h. The mixture was refluxed overnight. The white precipitate was collected by filtration and the filtrate discarded, yield, 5.4 g (76%).

Spectral Data. $^1$H NMR (500 MHz, $CD_3OD$): δ 6.70 (s, 1H), 6.58 (s, 1H), 4.55 (dd, 1H), 3.88 (s, 1H), 3.24-3.05 (m, 2H), 1.75 (s, 3H), 1.62 (s, 3H). $^{13}$C NMR (125 MHz, $CD_3OD$): 170.5, 146.8, 146.6, 129.6, 121.0, 116.05 (d, 1C), 112.64 (d, 1C), 60.3, 54.0, 52.3, 29.8, 28.8, 28.0. DEPT: CH3, 54.0, 28.8, 28.0; CH2, 29.8; CH, 116.05, 112.64, 52.3. HMQC δH (δC): 1.62 (28.8, $^1J_{C-H}$), 1.75 (28.0, $^1J_{C-H}$) 3.24-3.05 (29.8, $^1J_{C-H}$), 3.88 (54.0, $^1J_{C-H}$), 4.55 (52.3, $^1J_{C-H}$), 6.58 (116.05, $^1J_{C-H}$), 6.70 (112.64, $^1J_{C-H}$). HMBC δH (δC): 1.62 (28.0, $^3J_{C-H}$; 60.3, $^2J_{C-H}$; 129.6, $^3J_{C-H}$), 1.75 (28.8, $^3J_{C-H}$; 60.3, $^2J_{C-H}$; 129.6, $^3J_{C-H}$) 3.24-3.05 (52.3, $^2J_{C-H}$; 121.0, $^2J_{C-H}$), 3.88 (170.5, $^3J_{C-H}$), 4.55 (29.8, $^2J_{C-H}$; 170.5 $^2J_{C-H}$), 6.58 (29.8, $^3J_{C-H}$; 129.6, $^2J_{C-H}$; 149.6, $^2J_{C-H}$), 6.70 (60.3, $^3J_{C-H}$; 121.0, $^2J_{C-H}$; 146.6, $^2J_{C-H}$). MS (ESI): $C_{13}H_{17}NO_4$, MH+, 252.10. HRMS (ESI): $C_{13}H_{17}NO_4$, MH+, Calcd. 252.12303, Found 252.12270. mp 250-254° C., decomposed (FIGS. 63-66).

Analysis and Discussion. Following the Soloshonok method, a white solid product was obtained with a yield more than 76%. Ferric chloride test of the white solid gave a positive result, indicating the phenolic hydroxyl groups of the catechol were free and not protected. $^1$H NMR spectrum showed two singlet peaks, δ ppm 1.75 and 1.62 with a chemical shift difference of ca. 0.13, indicating the two methyl groups were in different chemical environments. The $^{13}$C NMR spectrum had only 7 peaks with δ ppm>100 (one from the carbonyl C and six from the phenyl C).

This data indicates that the method of the Soloshonok reference, consistent with the prior art in this field, does not yield acetonide-protected DOPA. This is because the quarternary carbon of the acetonide protecting group of the catechol usually has a chemical shift around δ ppm 117. DEPT NMR data indicated there are only two phenyl protons. Combined with the NMR data from HMQC, $^1$J coupling between H and its adjacent carbon, and HMBC, $^2$J, $^3$J, and $^4$J coupling of H and its neighbor carbons, it can be concluded that the product of this reaction was not the acetonide-protected DOPA. The product is methyl 6,7-dihydroxy-1,2,3,4-tetrahydroisoquinoline-3-carboxylate, as earlier reported by Okumura et al.[17]

It should be noted that the above description, attached figures and their descriptions are intended to be illustrative and not limiting of this invention. Many themes and variations of this invention will be suggested to one skilled in this and, in light of the disclosure. All such themes and variations are within the contemplation hereof. For instance, while this invention has been described in conjunction with the various exemplary embodiments outlined above, various alternatives, modifications, variations, improvements, and/or substantial equivalents, whether known or that rare or may be presently unforeseen, may become apparent to those having at least ordinary skill in the art. Various changes may be made without departing from the spirit and scope of the invention.

Therefore, the invention is intended to embrace all known or later-developed alternatives, modifications, variations, improvements, and/or substantial equivalents of these exemplary embodiments.

REFERENCES

1. Fant, et al. *Biomacromolecules* 2002, 3, 732-741.
2. Papov, et al. *J. Biol. Chem.* 1995, 270, 20183-20192.
3. Zhao et al *J. Biol. Chem.* 2005, 280, 42938-42944.
4. Miserez et al. *Science* 2008, 319, 1816-1819.
5. Rice-Ficht et al. *Mol. Biochem. Parasitol.* 1992, 54, 129-141.
6. Waite et al. *Mol. Biochem. Parasitol.* 1992, 54, 143-151.
7. Lee et al. *Proc. Natl. Acad. Sci. U. S. A.* 2006, 103, 12999-13003.
8. Yu et al. *Macromolecules* 1998, 31, 4739-4745.
9. Messersmith, P. B. *Science* 2008, 319, 1767-1768.
10. Mendis et al. *Can. J. Neurol. Sci.* 1999, 26, 89-103.
11. Hu et al. *Tetrahedron Lett.* 2000, 41, 5795-5798.
12. Sever et al. *Tetrahedron* 2001, 57, 6139-6146.
13. Ogura et al. *Tetrahedron Lett.* 1971, 3151-3154.
14. Soloshonok et al. *Synthesis* 2008, 693-695.
15. Statz et al. *J. Am. Chem. Soc.* 2005, 127, 7972-7973.
16. Hasegawa, T.; Usui, T. *Kagaku to Kyoiku* 1991, 39, 686-7.
17. Okumura et al. U.S. Pat. No. DE 2,342,474, U.S. Pat. No. 3,846,573, 1974.
18. Lee et al. *Synthesis* 2001, 2247-2254.
19. Kolasa et al., *J. Org. Chem.* 1990, 55, 1711-1721.
20. Yoshino *Bull. Chem. Soc. Jpn.* 1979, 52, 3005-9.
21. Griesbeck et al. *Tetrahedron* 1994, 50, 701-714.
22. Henz et al. *J. Inf. Rec.* 1994, 21, 567-569.
23. Wen, S.-J.; Yao, Z.-J. *Org. Lett.* 2004, 6, 2721-2724.
24. Kondejewski et al. *J. Biol. Chem.* 1999, 274, 13181-92.
25. Cluzeau et al. *Org. Biomol. Chem.* 2007, 5, 1915-1923.
26. Ishihara et al. *Org. Lett.* 2006, 8, 1921-1924.
27. Berthod et al. *J. Chromatogr. A* 1996, 731, 123-137.
28. Benes, F. M. *Trends Pharmacol. Sci.* 2001, 22, (1), 46-47.
29. Shashoua et al. W. *Life Sci.* 1996, 58, (16), 1347-57.
30. Fan *J. Am. Chem. Soc.* 2005, 127, (45), 15843-7; Xu et al. *J. Am. Chem. Soc.* 2004, 126, (32), 9938-9939; Lee et al. *Adv. Mater.* 2008, 20, 4154-4157; Lee et al. *Adv. Mater.* 2008, 20, 1916-1923.
31. Li et al. *Biomaterials* 2008, 29, (35), 4592-4597.
32. LaVoie et al. *J. Neurosci.* 1999, 19, (4), 1484-1491.
33. Garcia-Alvarez et al. *Chem Med Chem* 2007, 2, (4), 496-504.
34. Ikeuchi et al. *Heterocycles* 2005, 65, (12), 2925-2935.
35. Meltzer et al. *Bioorg. Med. Chem. Lett.* 2003, 13, (22), 4133-4137.
36. Nichols et al. *J. Med. Chem.* 1979, 22, (10), 1264-7.
37. Zhu et al. *Huaxue Xuebao* 2007, 65, (1), 37-42; Okano et al. *J. Am. Chem. Soc.* 2006, 128, (22), 7136-7137; Bojarski et al. *Bioorg. Med. Chem.* 2001, 10, (1), 87-95; Shen et al. *J. Biol. Chem.* 1982, 257, (13), 7294-7.
38. Harwood et al. *Biopolymers* 1978, 17, (12), 2939-43.
39. Maryanoff *Chem. Rev.* 2004, 104, (3), 1431-1628.
40. Morita et al. *Agric. Biol. Chem.* 1975, 39, (2), 547-9.
41. Felder Flesch et al. PCT Int. Pub. WO2008043911, 2008.
42. Cai et al. *J. Am. Chem. Soc.* 2004, 126, (46), 15030-15031.
43. Cole et al. *Aust. J. Chem.* 1980, 33, (3), 675-80.
44. Liu et al. *Tetrahedron Lett.* 2008, 49, (38), 5519-5521.
45. Babu, et al. *Synth. Commun.* 2005, 35, (13), 1795-1802.
46. Niederstein, Y.; Peter, M. G. *Liebigs Ann. Chem.* 1989, (12), 1189-93.
47. Godsay et al. *J. Polym. Mater.* 1991, 8, (3), 207-11.
48. Yu et al *Macromolecules* 2007, 40, (11), 3960-3964.
49. Backer et al. Patent WO 2002059107, 2002.
50. Backer et al. Patent WO 2003061660, 2003.
51. Shi et al. *Bioorg. Med. Chem. Lett.* 2006, 16, 2341-2346.
52. Tanaka et al. Patent JP 48022473, 1973.
53. Morita et al. *Agric. Biol. Chem.* 1975, 39, 547-9.

We claim:

1. A method of providing optically pure acetonide-protected 3,4-dihydroxyphenylalanine (H-DOPA(acetonide)-OH), comprising:
    a. protecting the amine group of L-DOPA with a phthaloyl group to yield Phth-DOPA-OH, the Phth-DOPA-OH comprising a carboxyl group;
    b. protecting the carboxyl group of Phth-DOPA-OH with a methyl ester to yield Phth-DOPA-OMe;
    c. converting Phth-DOPA-OMe via acetonide cyclization to yield Phth-DOPA(acetonide)-OMe; and
    d. deprotecting Phth-DOPA(acetonide)-OMe to yield optically pure H-DOPA(acetonide)-OH.

2. The method of claim 1 wherein the step of protecting the amine group of the L-DOPA comprises reacting the L-DOPA with N-carbethoxyphthalimide to yield Phth-DOPA-OH.

3. The method of claim 1 wherein the step of protecting the carboxyl group of Phth-DOPA-OH comprises reacting Phth-DOPA-OH with thionyl chloride in methanol to yield Phth-DOPA(acetonide)-OMe.

4. The method of claim 1 wherein the acetonide cyclization is carried out in the presence of paratoluene sulfonic acid under polar aprotic conditions.

5. The method of claim 1 wherein the step of deprotecting Phth-DOPA(acetonide)-OMe comprises reacting Phth-DOPA(acetonide)-OMe with hydrazine in methyl alcohol in dichloromethane.

6. The method of claim 5 wherein the step of deprotecting Phth-DOPA(acetonide)-OMe further comprises alkaline hydrolysis of Phth-DOPA(acetonide)-OMe by lithium hydroxide in tetrahydrofuran and water.

7. A method of providing optically pure Fmoc-protected 3,4-dihydroxyphenylalanine (Fmoc-DOPA(acetonide)-OH) comprising:
    a. protecting the amine group of L-DOPA with a phthaloyl group to yield Phth-DOPA-OH, the Phth-DOPA-OH comprising a carboxyl group;
    b. protecting the carboxyl group of Phth-DOPA-OH with a methyl ester to yield Phth-DOPA-OMe;
    c. converting Phth-DOPA-OMe via acetonide cyclization to yield Phth-DOPA(acetonide)-OMe;
    d. deprotecting Phth-DOPA(acetonide)-OMe to yield H-DOPA(acetonide)-OH; and
    e. reacting H-DOPA(acetonide)-OH with Fmoc-OSu to yield optically pure Fmoc-DOPA(acetonide)-OH.

8. The method of claim 7 wherein the acetonide cyclization is carried out in the presence paratoluene sulfonic acid under polar aprotic conditions.

9. A method of carrying out Fmoc-Solid Phase Peptide Synthesis to provide a DOPA-containing peptide product, the method comprising:
    a. attaching an Fmoc-protected amino acid to a resin;
    b. deprotecting the amino acid to yield a deprotected amino acid;
    c. coupling another Fmoc-protected amino acid to the deprotected amino acid;
    d. repeating steps (b) and (c) to yield an elongating peptide, wherein said method comprises the steps of incorporating an Fmoc-DOPA(acetonide)-OH prepared according to the method of claim 7 in the elongating peptide to yield a DOPA-containing peptide product.

10. A method of providing acetonide-protected 4-(2-aminoethyl)benzene-1,2-diol (dopamine) comprising:
   a. preprotecting the amino group of dopamine with a protecting group selected from the group consisting of a phthalimide, a carbamate and an amide to yield a protected dopamine product;
   b. converting the protected dopamine product of step (a) via acetonide cyclization to yield an acetonide-protected product;
   c. deprotecting the amine group of the acetonide-protected product of step (b) to yield acetonide-protected dopamine.

11. The method of claim 10 wherein the acetonide cyclization is carried out in the presence of paratoluene sulfonic acid under polar aprotic conditions.

12. The method of claim 10 wherein the protecting group is phthalimide, and the acetonide-protected product of step (b) has the structure:

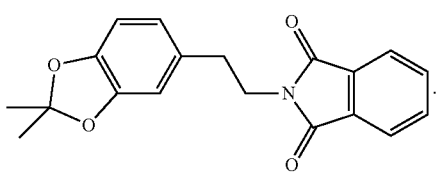

13. The method of claim 10 wherein the protecting group is carbamate, and the acetonide-protected product of step (b) has the structure:

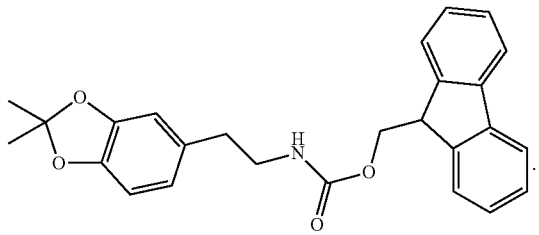

14. The method of claim 10 wherein the protecting group is an amide, and the acetonide-protected product of step (b) has the structure:

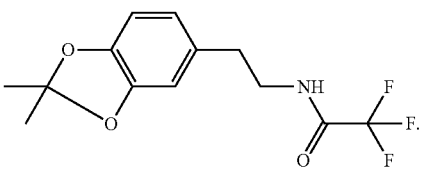

15. A method of providing an acetonide-protected catechol-containing molecule bearing at least one amine group, the method comprising:
   a. preprotecting the amine group of the catechol-containing molecule bearing the amine group with a protecting group to yield a protected catechol-containing molecule, wherein the catechol-containing molecule is selected from the group consisting of 3,4 dihydroxyphenylalanine (DOPA), 4-(2-aminoethyl)benzene-1,2-diol (dopamine), norepinephrine and epinephrine;
   b. converting the protected catechol-containing molecule of step (a) via acetonide cyclization to yield an acetonide-protected molecule;
   c. deprotecting the amine group of the acetonide-protected molecule of step (b) to yield an acetonide-protected catechol-containing molecule bearing at least one amine group.

16. The method of claim 15 wherein the protecting group is selected from the group consisting of a phthalimide, a carbamate and an amide.

17. The method of claim 15 wherein the acetonide cyclization is carried out in the presence of paratoluene sulfonic acid under polar aprotic conditions.

* * * * *

UNITED STATES PATENT AND TRADEMARK OFFICE
CERTIFICATE OF CORRECTION

PATENT NO. : 8,227,628 B2
APPLICATION NO. : 12/500398
DATED : July 24, 2012
INVENTOR(S) : Messersmith et al.

It is certified that error appears in the above-identified patent and that said Letters Patent is hereby corrected as shown below:

IN THE SPECIFICATIONS:

Column 1, lines 17-20 "The present invention was made with government support from National Institutes of Health Grant No. R37 DE014193. The United States Government has certain rights in this invention." should read -- This invention was made with government support under R37 DE014193 awarded by the National Institutes of Health. The government has certain rights in the invention. --

Column 10, line 19 "Meson" should read -- Mesoc --

Column 17, line 18 "DCMlhexane" should read -- DCM/hexane --

Column 18, line 5 "$CD_3OH$" should read -- $CD_3OD$ --

Column 23, line 14 "396.10433" should read -- 396.10533 --

Column 25, line 22 "$^1$NMR" should read -- $^1$H NMR --

Column 26, line 51 "TEA-dopamine" should read -- TFA-dopamine --

Signed and Sealed this
Twentieth Day of November, 2012

David J. Kappos
*Director of the United States Patent and Trademark Office*